(12) United States Patent
Oberboersch et al.

(10) Patent No.: US 8,541,573 B2
(45) Date of Patent: Sep. 24, 2013

(54) SUBSTITUTED SULFONAMIDE COMPOUNDS

(75) Inventors: Stefan Oberboersch, Aachen (DE); Ruth Jostock, Stolberg (DE); Klaus Schiene, Juechen (DE); Jean De Vry, Stolberg (DE); Tieno Germann, Aachen (DE); Sabine Hees, Aachen (DE); Stefan Schunk, Aachen (DE); Melanie Reich, Aachen (DE)

(73) Assignee: Gruenenthal GmbH, Aachen (DE)

( * ) Notice: Subject to any disclaimer, the term of this patent is extended or adjusted under 35 U.S.C. 154(b) by 686 days.

(21) Appl. No.: 12/397,771

(22) Filed: Mar. 4, 2009

(65) Prior Publication Data

US 2009/0298812 A1 Dec. 3, 2009

Related U.S. Application Data

(60) Provisional application No. 61/033,987, filed on Mar. 5, 2008.

(30) Foreign Application Priority Data

Mar. 5, 2008 (EP) .................................. 08004073

(51) Int. Cl.
 A61K 31/538 (2006.01)
 A61K 31/496 (2006.01)
 C07D 401/14 (2006.01)
 C07D 498/04 (2006.01)

(52) U.S. Cl.
 USPC ........... 544/105; 544/360; 544/363; 544/364; 514/230.8; 514/253.01; 514/253.07

(58) Field of Classification Search
 None
 See application file for complete search history.

(56) References Cited

FOREIGN PATENT DOCUMENTS

WO WO 2007/101007 A2 9/2007

OTHER PUBLICATIONS

R. Hayashi et al., "Bradykinin Stimulates IL-6 and IL-8 Production by Human Lung Fibroblasts Through ERK- and p38 MAPK-dependent Mechanisms", European Respiratory Journal, 2000, pp. 452-458, vol. 16, ISSN: 0903-1936.
Bichoy H. Gabra et al., "*The Kinin System Mediates Hyperalgesia* through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Joao B. Calixto et al., "Kinin $B_1$ Receptors: Key G-protein-coupled Receptors and their Role in Inflammatory and Painful Processes", British Journal of Pharmacology, 2004, pp. 803-818, vol. 143, 2004 Nature Publishing Group.
Sara H. Bengtson et al., "Kinin Receptor Expression During *Staphylococcus aureus* Infection", Blood, Sep. 15, 2006, pp. 2065-2063, vol. 108, No. 6, The American Society of Hematology.
Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol, Mar. 31, 2005, pp. G361-G366, vol. 289, American Physiological Society.
Joao B. Pesquero et al., "Genetically Altered Animal Models in the Kallikrein-Kinin System", Biol. Chem., Feb. 2006, pp. 119-126, vol. 387.
A. Prat et al., "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology, ISSN: 0028-3878.
J. Fred Hess et al., "Generation and characterization of a humanized bradykinin B1 receptor mouse", Biol. Chem., vol. 387, pp. 195-201, Feb. 2006.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.
Giselle F. Passos, et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847.
European Search Report dated Aug. 21, 2008 (Four (4) pages).
International Search Report with partial translation dated Jun. 15, 2009 (Three (3) pages).
PCT/ISA/237 (Five (5) pages), Jun. 15, 2009.
PCT/ISA/220 (Three (3) pages), Jun. 15, 2009.

(Continued)

*Primary Examiner* — Laura L. Stockton
(74) *Attorney, Agent, or Firm* — Crowell & Moring LLP

(57) ABSTRACT

Substituted sulfonamide compounds corresponding to the formula I

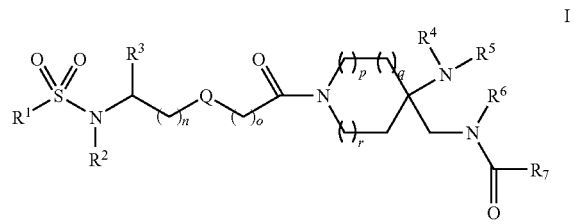

processes for the preparation thereof, pharmaceutical compositions containing these compounds and the use of substituted sulfonamide compounds for the preparation of pharmaceutical compositions for treating pain and other conditions at least partly mediated via the bradykinin 1 receptor.

22 Claims, No Drawings

(56) References Cited

OTHER PUBLICATIONS

"The involvement of kallikrein—kinin system in diabetes type I (insulitis)", A. Zuccolio et al., Immunopharmacology 45 (1999) pp. 69-74.
"Comparison of kinin $B_1$ and $B_2$ receptor expression in neutrophils of asthmatic and non-asthmatic subjects", C. Betram et al., International Immunopharmacology 7 (2007) pp. 1862-1868.
"Mechanism of cigarette smoke-induced kinin $B_1$ receptor expression", J. Chi-Jen Lin, et al., Peptides 31 (2010) pp. 1940-1945, available online Jul. 15, 2010.
"Bradykinin $B_1$ receptor antagonist R954 inhibits eosinophil activation/proliferation/migration and increases TGF-β and VEGF in a murine model of asthma", L. Vasquez-Pinto et al., Neuropeptides 44 (2010) pp. 107-113, available online Dec. 3, 2009.
"IL-1β-Induced Transcriptional Up-Regulation of Bradykinin $B_1$ and $B_2$ Receptors in Murine Airways", Y. Zhang et al., American Journal of Respiratory Cell and Molecular Biology, vol. 36, 2007, pp. 697-705.
"The relevance of kinin $B_1$ receptor upregulation in a mouse of colitis", DB Hara et al., British Journal of Pharmacology (2008), pp. 1-11, advance online publication Jun. 9, 2008.
"Therapeutic options in inflammatory bowel disease: experimental evidence of beneficial effect of kinin $B_1$ receptor blockade", F. Marceau et al., British Journal of Pharmacology (2008), pp. 1-3, advance online publication Jun. 9, 2008.
"Blockade of kinin receptor $B_1$ protects from autoimmune CNS disease by reducing leukocyte trafficking", K. Göbel et al., Journal of Autoimmunity (2010), pp. 1-9, doi:10.1016/j-jaut.2010.11.004.
"Targeting Kinin Receptors for the Treatment of Neurological Diseases", D. Rodi et al., Current Pharmaceutical Design, 2005, 11, pp. 1313-1326.
"The role of kinin $B_1$ and $B_2$ receptors in the scratching behavior induced by proteinase-activated receptor-2 agonists in mice", R. Costa et al., British Journal of Pharmacology (2010), 159, pp. 888-897, published online Jan. 8, 2010.
"The non-peptide kinin receptor antagonists FR 173657 and SSR 240612: Preclinical evidence for the treatment of skin inflammation", E. F. Pietrovski et al., Regulatory Peptides (2008), doi:10.1016/j.regpep.2008.10.005.
"Kallikreins, kniniogens and kinin receptors on circulating and synovial fluid neutrophils: role in kinin generation in rheumatoid arthritis", B. Cassim et al., Rheumatology 2009; 48, pp. 490-496, advance access publication Mar. 1, 2009.
"Overexpression of Kinin $B_1$ Receptors Induces Hypertensive Response to Des-$Arg^9$-bradykinin and Susceptibility to Inflammation", A. Ni et al., The Journal of Biological Chemistry, vol. 278, No. 1, Issue of Jan. 3, pp. 219-226, 2003, published JBC Papers in Press Oct. 30, 2002.
"Endothelial Kinin $B_1$-receptors are induced by myocardial ischaemia-reperfusion in the rabbit", C. Mazenot et al., Journal of Physiology (2001), 530.1, pp. 69-78.
"Role of Bradykinin B23 and B1 Receptors in the Local, Remote, and Systemic Inflammatory Responses that Follow Intestinal Ischemia and Reperfusion Injury", D. Souza et al., Journal of Immunology 2004; 172; pp. 2542-2548.
"Kinin $B_1$ Receptor Deficiency Leads to Leptin Hypersensitivity and Resistance to Obesity", M. Mori et al., Diabetes, vol. 57, Jun. 2008, pp. 1491-1500, published ahead of print Mar. 10, 2008.
Regulation of Angiogenesis by the Kallikrein-Kinin System, Robert W. Coleman, Current Pharmaceutical Design, 2006, vol. 12, No. 21, pp. 2599-2607.
"The bradykinin/B1 receptor promotes angiogenesis by up-regulation of endogenous FGF-2 in endothelium via the nitric oxide synthase pathway", A. Parenti et al., The *FASEB Journal*, published online Apr. 27, 2001.

SUBSTITUTED SULFONAMIDE COMPOUNDS

CROSS REFERENCE TO RELATED APPLICATIONS

This application claims priority from U.S. provisional patent application No. 61/033,987, and from European patent application no. EP 08004073.6, both filed Mar. 5, 2008.

BACKGROUND OF THE INVENTION

The present invention relates to substituted sulfonamide compounds, processes for the preparation thereof, pharmaceutical compositions containing these compounds and the use of substituted sulfonamide compounds for the preparation of pharmaceutical compositions.

In contrast to the constitutive expression of the bradykinin 2 receptor (B2R), in most tissues the bradykinin 1 receptor (B1R) is not expressed or expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of B1R (Passos et al. J. Immunol. 2004, 172, 1839-1847). After activation with specific ligands, B1R-expressing cells then themselves can secrete inflammation-promoting cytokines such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol. Rev. 2005, 57, 27-77 und Pesquero et al., Biol. Chem. 2006, 387, 119-126). On humans too, an enhanced expression of B1R, e.g. on enterocytes and macrophages, in the affected tissue of patients with inflammatory intestinal diseases (Stadnicki et al., Am. J. Physiol. Gastrointest. Liver Physiol. 2005, 289, G361-366) or on T lymphocytes of patients with multiple sclerosis (Prat et al., Neurology. 1999; 53, 2087-2092) or an activation of the bradykinin B2R-B1R system in the course of infections with Staphylococcus aureus (Bengtson et al., Blood 2006, 108, 2055-2063) is found. Infections with Staphylococcus aureus are responsible for syndromes such as superficial infections of the skin up to septic shock.

Based on the pathophysiological relationships described, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin (receptor) system is moreover also involved in regulation of angiogenesis (potential as an angiogenesis inhibitor in cancer cases and macular degeneration on the eye), and B1R knockout mice are protected from induction of obesity by a particularly fat-rich diet (Pesquero et al., Biol. Chem. 2006, 387, 119-126). B1R antagonists are therefore also suitable for treatment of obesity.

B1R antagonists are suitable in particular for treatment of pain, in particular inflammation pain and neuropathic pain (Calixto et al., Br. J. Pharmacol. 2004, 1-16), and here in particular diabetic neuropathy (Gabra et al., Biol. Chem. 2006, 387, 127-143). They are furthermore suitable for treatment of migraine.

In the development of B1R modulators, however, there is the problem that the human and the rat B1R receptor differ so widely that many compounds which are good B1R modulators on the human receptor have only a poor or no affinity for the rat receptor. This makes pharmacological studies on animals considerably difficult, since many studies are usually conducted on the rat. However, if no activity exists on the rat receptor, neither the action nor side effects can be investigated on the rat. This has already led to transgenic animals with human B1 receptors being produced for pharmacological studies on animals (Hess et al., Biol. Chem. 2006; 387(2): 195-201). Working with transgenic animals, however, is more expensive than working with the unmodified animals. Since in the development of pharmaceutical compositions, however, precisely long-term toxicity studies on the rat belong to the standard studies, but this is inappropriate in the event of an absence of activity on the receptor, an important established instrument for checking safety is lacking for the development of such compounds. There is therefore a need for novel B1R modulators, B1R modulators which bind both to the rat receptor and to the human receptor offering particular advantages.

SUMMARY OF THE INVENTION

One object of the present invention was therefore to provide novel compounds which are suitable in particular as pharmacological active compounds in pharmaceutical compositions.

Another object of the invention was to provide new compounds and pharmaceutical compositions for treatment of disorders or diseases which are at least partly mediated by B1R receptors.

These and other objects have been achieved by providing the substituted sulfonamide compounds according to the invention.

Accordingly, the present invention provides substituted sulfonamide compounds corresponding to formula I

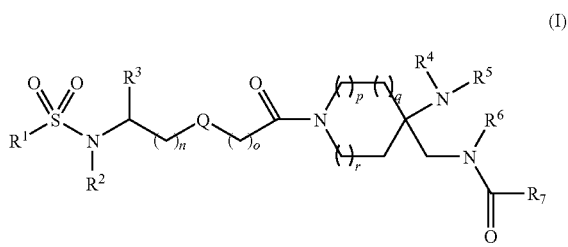

(I)

wherein
n represents 0, 1 or 2;
o represents 1, 2 or 3;
p represents 1 or 2;
q represents 0 or 1;
r represents 0 or 1;

Q represents a single bond, —O— or —CH$_2$—;

R$^1$ represents aryl or heteroaryl or denotes an aryl or heteroaryl bonded via a C$_{1-3}$-alkylene group;

R$^2$ and R$^3$ are defined as described under (i) or (ii):

(i) R$^2$ represents H, C$_{1-6}$-alkyl, C$_{3-8}$cycloalkyl, aryl or heteroaryl; or denotes a C$_{3-8}$-cycloalkyl, aryl or heteroaryl bonded via a C$_{1-6}$-alkylene group, C$_{2-6}$-alkenylene group or C$_{2-6}$-alkynylene group; and R$^3$ represents H, C$_{1-6}$-alkyl, aryl or heteroaryl; or denotes an aryl or heteroaryl bonded via a C$_{1-6}$-alkylene group, C$_{2-6}$-alkenylene group or C$_{2-6}$-alkynylene group; or (ii) R$^2$ and R$^3$ together form a heterocyclic ring, which can be fused with an aryl or heteroaryl group, wherein the heterocyclic ring is saturated or at least monounsaturated, but not aromatic, is 4-, 5-, 6- or 7-membered, can contain, in addition to the N hetero atom to which the radical R$^2$ is bonded, at least one further hetero atom or a hetero atom group selected from the group consisting of N, NR$^{12}$, O, S, S=O or S(=O)$_2$, and can be condensed with at least one aryl or heteroaryl;

wherein the radical R$^{12}$ represents H, C$_{1-6}$-alkyl, —C(=O)—R$^{13}$, C$_{3-8}$-cycloalkyl, aryl, heteroaryl or a C$_{3-8}$-cycloalkyl, aryl or heteroaryl bonded via a C$_{1-3}$-alkylene group, and R$^{13}$ denotes C$_{1-6}$-alkyl, C$_{3-8}$-cycloalkyl, aryl, heteroaryl or a C$_{3-8}$-cycloalkyl, aryl or heteroaryl bonded via a C$_{1-3}$-alkylene group, R$^4$ and R$^5$ independently of one another represent H, C$_{1-6}$-alkyl, C$_{2-6}$-alkenyl, C$_{2-6}$-alkynyl, C$_{3-8}$-cycloalkyl, 3- to 8-membered heterocycloalkyl, aryl or heteroaryl or a C$_{3-8}$-cycloalkyl, 3- to 8-membered heterocycloalkyl, aryl or heteroaryl bonded via a C$_{1-3}$-alkylene group;

or

R$^4$ and R$^5$ together form an unsubstituted or mono- or polysubstituted heterocyclic ring, which can be fused with a saturated, at least monounsaturated or aromatic, unsubstituted or mono- or polysubstituted ring system, wherein the heterocyclic ring is saturated, at least monounsaturated, but not aromatic, is 4-, 5-, 6- or 7-membered, can contain, in addition to the N hetero atom to which the radicals R$^4$ and R$^5$ are bonded, at least one hetero atom or a hetero atom group selected from the group consisting of N, NR$^8$, O, S, S=O and S(=O)$_2$, the ring system is 4-, 5-, 6- or 7-membered, can contain at least one hetero atom or a hetero atom group selected from the group consisting of N, NR$^{17}$, O, S, S=O and S(=O)$_2$, R$^8$ represents a radical selected from the group consisting of H, C$_{1-6}$-alkyl, C$_{3-8}$-cycloalkyl, aryl, heteroaryl or an aryl, heteroaryl or C$_{3-8}$-cycloalkyl bonded via a C$_{1-3}$-alkylene group and R$^{17}$ represents a radical selected from the group consisting of H, C$_{1-6}$-alkyl, C$_{3-8}$-cycloalkyl, aryl, heteroaryl or an aryl, heteroaryl or C$_{3-8}$-cycloalkyl bonded via a C$_{1-3}$-alkylene group;

R$^6$ represents H, C$_{1-6}$-alkyl, or a C$_{3-8}$-cycloalkyl bonded via a C$_{1-3}$-alkylene group, an aryl bonded via a C$_{1-3}$-alkylene group or a heteroaryl bonded via a C$_{1-3}$-alkylene group, and R$^7$ represents C$_{1-6}$-alkyl, C$_{2-6}$-alkenyl or C$_{2-6}$-alkynyl, C$_{3-8}$cycloalkyl, aryl or heteroaryl; or denotes a C$_{3-8}$-cycloalkyl, aryl or heteroaryl bonded via a C$_{1-6}$-alkylene group, or R$^6$ and R$^7$, with inclusion of the —N—C(=O) group, form a ring of the type

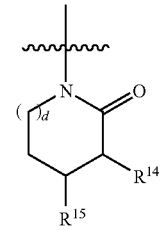

wherein d represents 0 or 1 and R$^{14}$ and R$^{15}$ together represent an annellated unsubstituted or substituted aryl or heteroaryl radical;

wherein the abovementioned radicals C$_{1-6}$-alkyl, C$_{1-6}$-alkylene, C$_{2-6}$-alkenylene, C$_{2-6}$-alkynylene, C$_{3-8}$-cycloalkyl, heterocycloalkyl, aryl and heteroaryl can in each case be unsubstituted or substituted once or several times by identical or different substituents and the abovementioned radicals C$_{1-6}$-alkyl, C$_{1-6}$-alkylene, C$_{2-6}$-alkenylene and C$_{2-6}$-alkynylene can in each case be branched or unbranched;

in the form of an individual enantiomer or of an individual diastereomer, of the racemate, of the enantiomers, of the diastereomers, mixtures of the enantiomers and/or diastereomers, and in each case in the form of their bases and/or physiologically acceptable salts.

In selected embodiments of the substituted sulfonamide compounds according to the present invention, n represents 0 or 1.

In the context of the present invention, the term "halogen" preferably represents F, Cl, Br and I, particularly preferably F, Cl and Br.

In the context of this invention, the expression "C$_{1-6}$-alkyl" includes acyclic saturated hydrocarbon groups having 1, 2, 3, 4, 5 or 6 carbon atoms, which can be branched- or straight-chain (unbranched) and unsubstituted or substituted once or several times, for example 2, 3, 4 or 5 times, by identical or different substituents. The alkyl radicals can preferably be selected from the group consisting of methyl, ethyl, n-propyl, iso-propyl, n-butyl, iso-butyl, sec-butyl, tert-butyl, n-pentyl, iso-pentyl, neo-pentyl and hexyl. Particularly preferred alkyl radicals can be selected from the group consisting of methyl, ethyl, n-propyl, iso-propyl, n-butyl, sec-butyl, iso-butyl and tert-butyl.

In the context of this invention, the expression "C$_{2-6}$-alkenyl" includes acyclic unsaturated hydrocarbon radicals having 2, 3, 4, 5 or 6 carbon atoms, which can be branched or straight-chain (unbranched) and unsubstituted or substituted once or several times, for example 2, 3, 4 or 5 times, by identical or different substituents. In this context, the alkenyl radicals contain at least one C=C double bond. Alkenyl radicals can preferably be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl radicals can be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl and but-1-en-2-yl.

In the context of this invention, the expression "C$_{3-8}$-cycloalkyl" denotes cyclic saturated hydrocarbon radicals having 3, 4, 5, 6, 7 or 8 carbon atoms, which can be unsubstituted or substituted once or several times, for example by 2, 3, 4 or 5 identical or different radicals, on one or more ring members. $C_{3-8}$-Cycloalkyl can preferably be selected from the group consisting of cyclopropyl, cyclobutyl, cyclopentyl, cyclohexyl, cycloheptyl and cyclooctyl.

The expression "3- to 8-membered heterocycloalkyl" designates saturated heterocyclic rings which can contain as ring members, chosen independently of one another, 1, 2, 3, 4 or 5 identical or different hetero atoms, preferably from the group N, O or S. In the case where the heterocycloalkyl is bonded to a hetero atom, for example N, bonding to the heterocycloalkyl is preferably via one of the carbon ring members of the heterocycloalkyl. 3- to 8-membered heterocycloalkyls can be, in particular, 4-, 5- or 6-membered. Examples of 3- to 8-membered heterocycloalkyls are azetidinyl, pyrrolidinyl, piperidinyl, piperazinyl, morpholinyl, tetrahydropyranyl, dioxanyl and dioxolanyl, which can optionally be substituted as explained below.

In the context of this invention, the expression "aryl" denotes aromatic hydrocarbons, in particular phenyls and naphthyls. The aryl radicals can also be condensed with further saturated, (partially) unsaturated or aromatic ring systems. Each aryl radical can be unsubstituted or substituted once or several times, for example 2, 3, 4 or 5 times, wherein the substituents on the aryl can be identical or different and can be in any desired and possible position of the aryl. Aryl can advantageously be selected from the group consisting of phenyl, 1-naphthyl and 2-naphthyl, which can in each case be unsubstituted or substituted once or several times, for example by 2, 3, 4 or 5 substituents.

In the context of the present invention, the expression "heteroaryl" represents a 5-, 6- or 7-membered cyclic aromatic group which contains at least 1, if appropriate also 2, 3, 4 or 5 hetero atoms, wherein the hetero atoms can be identical or different and the heteroaryl can be unsubstituted or substituted once or several times, for example 2, 3, 4 or 5 times, by identical or different substituents. The substituents can be bonded in any desired and possible position of the heteroaryl. The heterocyclic ring can also be part of a bi- or polycyclic, in particular a mono-, bi- or tricyclic system, which can then be more than 7-membered in total, preferably up to 14-membered. Preferred hetero atoms are selected from the group consisting of N, O and S. The heteroaryl group can preferably be selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzoxazolyl, benzoxadiazolyl, imidazothiazolyl, dibenzofuranyl, dibenzothienyl, phthalazinyl, pyrazolyl, imidazolyl, thiazolyl, oxadiazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, wherein bonding to the general structure I can be via any desired and possible ring member of the heteroaryl radical. The heteroaryl group can be particularly preferably selected from the group consisting of furyl, thienyl and pyridinyl.

In the context of the present invention, the expression "$C_{1-6}$-alkylene group" includes acyclic saturated hydrocarbon groups having 1, 2, 3, 4, 5 or 6 carbon atoms, which can be branched- or straight-chain (unbranched) and unsubstituted or substituted once or several times, for example 2, 3, 4 or 5 times, by identical or different substituents and which link a corresponding group to the main general structure. The alkylene groups can preferably be selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. The alkylene group can be particularly preferably selected from the group consisting of —CH$_2$—, —CH$_2$—CH$_2$— and —CH$_2$—CH$_2$—CH$_2$—.

In the context of the present invention, the expression "$C_{2-6}$-alkenylene group" includes acyclic hydrocarbon radicals having 2, 3, 4, 5 or 6 Carbon atoms, which are unsaturated once or several times, for example 2, 3 or 4 times, and can be branched- or straight-chain (unbranched) and unsubstituted or substituted once or several times, for example 2, 3, 4 or 5 times, by identical or different substituents and which link a corresponding group to the main general structure. In this context, the alkenylene groups contain at least one C=C double bond. The alkenylene groups can preferably be selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —CH=CH—CH$_2$—CH$_2$—CH$_2$—, —CH$_2$—CH=CH—CH$_2$—CH$_2$—, —CH=CH—CH—CH$_2$—CH$_2$— and —CH=CH$_2$—CH—CH=CH$_2$—.

In the context of the invention, the expression "$C_{2-6}$-alkynylene group" includes acyclic hydrocarbon groups having 2, 3, 4, 5 or 6 carbon atoms, which are unsaturated once or several times, for example 2, 3 or 4 times, and can be branched- or straight-chain (unbranched) and unsubstituted or substituted once or several times, for example 2, 3, 4 or 5 times, by identical or different substituents and which link a corresponding group to the main general structure. In this context, the alkynylene groups contain at least one C=C triple bond. The alkynylene groups can preferably be selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

In the context of the present invention, the expression "aryl or heteroaryl bonded via a $C_{1-6}$-alkylene group, $C_{2-6}$-alkenylene group or $C_{2-6}$-alkynylene group" means that the $C_{1-6}$-alkylene groups, $C_{2-6}$-alkenylene groups, $C_{2-8}$-alkynylene groups and aryl or heteroaryl have the meanings defined above and the aryl or heteroaryl is bonded to the main general structure via a $C_{1-6}$-alkylene group, $C_{2-6}$-alkenylene group or $C_{2-6}$-alkynylene group. Examples include benzyl, phenethyl and phenylpropyl.

In the context of the present invention, the expression "$C_{3-8}$-cycloalkyl and heterocyclyl bonded via a $C_{1-6}$-alkylene group, $C_{2-6}$-alkenylene group or $C_{2-6}$-alkynylene group" means that the $C_{1-6}$-alkylene group, $C_{2-6}$-alkenylene group, $C_{2-8}$-alkynylene group, $C_{3-8}$-cycloalkyl and heterocyclyl have the meanings defined above and $C_{3-8}$-cycloalkyl and heterocyclyl are bonded to the main general structure via a $C_{1-6}$-alkylene group, $C_{2-6}$-alkenylene group or $C_{2-6}$-alkynylene group.

In connection with "alkyl", "alkenyl", "alkylene", "alkenylene", "alkynylene" and "cycloalkyl", in the context of this invention the term "substituted" is understood as meaning replacement of a hydrogen atom by F, Cl, Br, I, CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl, where groups substituted several times are to be understood as meaning those groups which are substituted several times, for example two or three times, either on different or on the same atoms, for example three times on the same C atom, as in the case of $CF_3$ or $CH_2CF_3$, or at different places, as in the case of CH(Cl)—CH=CH—$CHCl_2$. Substitution several times can be by identical or different substituents, such as, for example, in the case of CH(OH)—CH=CH—$CHCl_2$.

With respect to "aryl" and "heteroaryl", in the context of this invention "substituted" is understood as meaning replacement once or several times, for example 2, 3, 4 or 5 times, of one or more hydrogen atoms of the corresponding ring system by F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl$^1$, N(aryl$^1$)$_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C(CH$_3$)$_2$—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, furyl, wherein aryl$^1$ represents phenyl, furyl, thienyl or pyridinyl, on one or different atoms, wherein the abovementioned substituents—unless stated otherwise—can optionally be substituted in their turn by the substituents mentioned. Substitution of aryl and heteroaryl several times can be by identical or different substituents. Preferred substituents for aryl and heteroaryl can be selected from the group consisting of —O—$C_{1-3}$-alkyl, unsubstituted $C_{1-6}$-alkyl, F, Cl, Br, I, $CF_3$, $OCF_3$, OH, SH, phenyl, naphthyl, furyl, thienyl and pyridinyl, in particular from the group consisting of F, Cl, Br, $CF_3$, $CH_3$ and $OCH_3$.

In connection with "3- to 8-membered heterocycloalkyl", the term "substituted" is understood as meaning replacement of a hydrogen on one or more ring members by F, Cl, Br, I, —CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl. Substitution several times can be by identical or different substituents. A hydrogen bonded to an N ring member can be replaced by a $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group, wherein these alkyl, cycloalkyl, alkylene and aryl and heteroaryl groups can be unsubstituted or substituted as defined above. Examples of substituted 3- to 8-membered heterocycloalkyl groups include 1-methylpiperidin-4-yl, 1-phenylpiperidin-4-yl, 1-benzylpiperidin-4-yl, 1-methylpyrrolidin-3-yl, 1-phenylpyrrolidin-3-yl, 1-benzylpyrrolidin-3-yl, 1-methylazetidin-3-yl, 1-phenyl-azetidin-3-yl or 1-benzylazetidin-3-yl.

In connection with "heterocyclic ring", in the context of this invention the term "substituted" means replacement of a hydrogen bonded to a carbon ring atom by F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl. If a heterocyclic group is substituted several times, the substituents can be on one and/or more carbon ring atoms. In preferred embodiments, one or more hydrogens on one or more carbon ring atoms are exchanged for F.

In connection with the "saturated or at least partly unsaturated ring system", which is fused with the heterocyclic ring formed by $R^4$ and $R^5$, in the context of this invention the term "substituted" is understood as meaning replacement of a hydrogen bonded to a carbon ring atom by F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl. If the ring system is substituted several times, the substituents can be on one and/or more carbon ring atoms. In connection with the "aromatic ring system", which is fused with the heterocyclic ring formed by $R^4$ and $R^5$, in the context of this invention the term "substituted" is understood as meaning the corresponding substitution as defined for aryl and heteroaryl.

In the context of the present description, the symbol

used in formulas designates a linking of a corresponding group to the particular main general structure.

In the context of this invention, the term "physiologically acceptable salt" is understood as meaning preferably salts of the compounds according to the invention with inorganic or organic acids, which are physiologically acceptable—in particular when used on humans and/or mammals. Examples of suitable acids are hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. The salts of hydrochloric acid (hydrochlorides) and of citric acid (citrates) are particularly preferred.

In a preferred embodiment of the present invention, in the substituted sulfonamide compounds according to the invention the group $R^1$ represents phenyl, naphthyl, Indolyl, benzofuranyl, benzothiophenyl (benzothienyl); benzoxazolyl, benzoxadiazolyl, pyrrolyl, furanyl, thienyl, pyridinyl, pyridazinyl, pyrimidinyl, pyrazinyl, imidazothiazolyl, carbazolyl, dibenzofuranyl or dibenzothiophenyl (dibenzothienyl), benzyl or phenethyl, preferably phenyl, naphthyl, benzothiophenyl, benzoxadiazolyl, thiophenyl, pyridinyl, imidazothiazolyl or dibenzofuranyl, particularly preferably phenyl or naphthyl, in each case unsubstituted or substituted once or several times by identical or different substituents, the substituents preferably being selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl.

In a further preferred embodiment of the present invention, in the substituted sulfonamide compounds according to the invention the group $R^1$ represents phenyl or naphthyl, wherein the phenyl or naphthyl is unsubstituted or substituted once or several times, for example 2, 3, 4 or 5 times, by identical or different substituents selected from the group consisting of methyl, methoxy, $CF_3$, $OCF_3$, F, Cl and Br.

In a further preferred embodiment, the group $R^1$ in the sulfonamide compounds according to the invention is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 2-chloro-6-(trifluoromethyl)phenyl, 2,6-dichloro-4-methoxyphenyl, 2-methylnaphthyl, 2-chloronaphthyl, 2-fluoronaphthyl, 2-chloro-4-(trifluoromethoxy)phenyl, 4-chloro-2,5-dimethylphenyl, 2,3-dichlorophenyl, 3,4-dichlorophenyl, 2-(trifluoromethyl)phenyl, 3-(trifluoromethyl)phenyl, 4-(trifluoromethyl)phenyl, 1-naphthyl and 2-naphthyl.

In a further preferred embodiment, the group $R^1$ in the sulfonamide compounds according to the invention is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 4-chloro-2,5-dimethylphenyl, 2,3-dichlorophenyl, 3,4-dichlorophenyl, 2-(trifluoromethyl)phenyl, 3-(trifluoromethyl)phenyl, 4-(trifluoromethyl)phenyl, 1-naphthyl and 2-naphthyl.

In a further preferred embodiment, the group $R^1$ in the sulfonamide compounds according to the invention is 4-methoxy-2,6-dimethylphenyl, 3,4-dichlorophenyl, 4-chloro-2,5-methylphenyl or 2,4,6-trimethylphenyl, preferably 4-methoxy-2,6-dimethylphenyl.

In a preferred embodiment of the substituted sulfonamide compounds according to the invention, p, q and r represent 1.

In a further preferred embodiment of the compounds according to the invention, Q represents a single bond, $CH_2$ or —O—, preferably a single bond or —O—, n represents 0 or 1 and o represents 1.

In a further preferred embodiment of the substituted sulfonamide compounds according to the invention, $R^4$ and $R^5$ independently of one another represent H, substituted or unsubstituted $C_{1-6}$-alkyl, in particular methyl, ethyl, n-propyl, iso-propyl, n-butyl, sec-butyl, iso-butyl or t-butyl.

In a further preferred embodiment of the substituted sulfonamide compounds according to the invention, the group —$NR^4R^5$ represents a ring of the type according to the general formula IIa

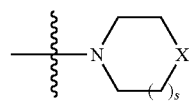

IIa wherein X represents O, S, $NR^8$ or C(halogen)$_2$. In this context, $R^8$ represents H, $C_{1-6}$-alkyl, in particular methyl, ethyl, n-propyl, iso-propyl, n-butyl, iso-butyl, sec-butyl, tert-butyl; or $R^8$ denotes aryl, preferably phenyl or naphthyl; or $R^8$ represents heteroaryl, preferably a 5- to 6-membered heteroaryl having 1 or 2 N hetero atoms, in particular 2-, 3- or 4-pyridinyl; or $R^8$ represents an aryl, preferably phenyl or naphthyl, bonded via a $C_{1-3}$-alkylene group; or a heteroaryl, preferably a 5- to 6-membered heteroaryl having 1 or 2 N hetero atoms, in particular 2-, 3- or 4-pyridinyl, bonded via a $C_{1-3}$-alkylene group. In the group C(halogen)$_2$, halogen represents F, Cl, Br or I, preferably F. In the structure according to the general formula IIa, s represents 0, 1 or 2, preferably 1, wherein s is not 0 if X represents $NR^8$. The radicals $C_{1-6}$-alkyl, aryl and heteroaryl mentioned above in connection with $R^8$ can in each case be unsubstituted or substituted once or several times by identical or different substituents. For example, the aryl or heteroaryl can in each case be unsubstituted or substituted once or several times, for example 2, 3, 4 or 5 times, by identical or different substituents selected from the group consisting of O—$C_{1-3}$-alkyl, unsubstituted $C_{1-6}$-alkyl, F, Cl, Br, I, $CF_3$, $OCF_3$, OH and SH.

In particular, the ring according to the general formula IIa can represent one of the following groups:

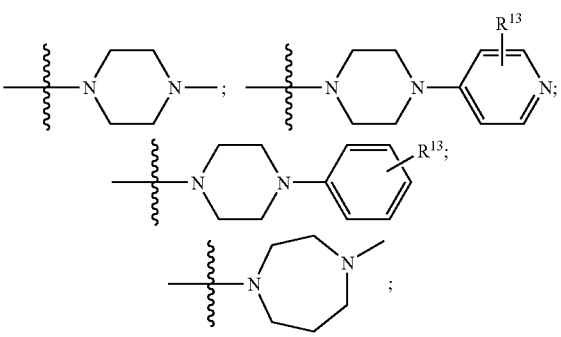

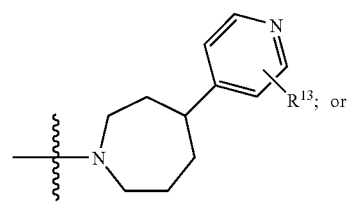

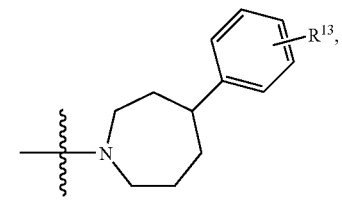

wherein $R^{13}$ represents one or, independently of one another, more substituents from the group H, F or Cl.

In a further preferred embodiment of the substituted sulfonamide compounds according to the invention, the group —$NR^4R^5$ represents a ring of the type according to the general formula IIb:

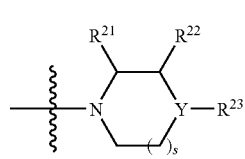

IIb wherein s can be 0 or 1, Y represents CH or N, under the condition that if s=0, Y is not N, and two adjacent radicals $R^{21}$, $R^{22}$ and $R^{23}$ together form an annellated group of the type

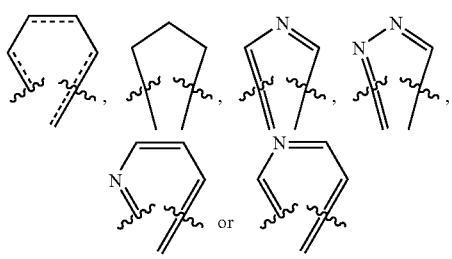

and the particular third radical from $R^{21}$, $R^{22}$ and $R^{23}$ denotes H and ===== denotes a single or double bond.

Persons skilled in the art understand that if two adjacent radicals from $R^{21}$, $R^{22}$ and $R^{23}$ form an annellated ring which is aromatic, the two carbon atoms to which these two adjacent radicals are bonded can no longer carry a hydrogen.

For example, —$NR^4R^5$ can represent one of the following groups:

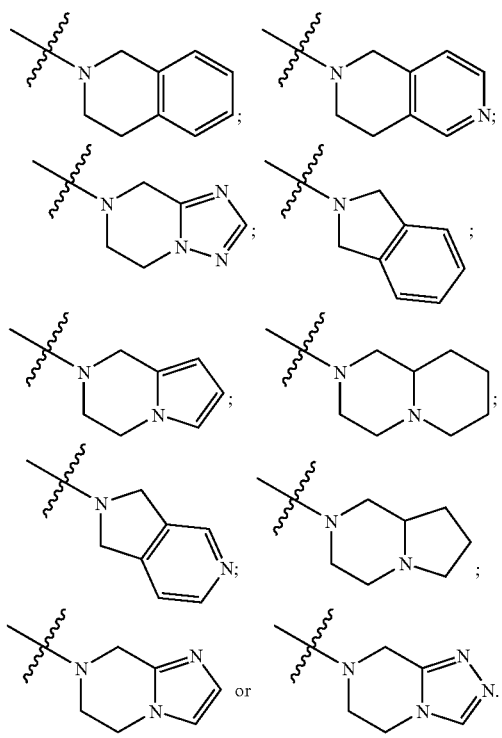

In a further preferred embodiment of the substituted sulfonamide compounds according to the invention, the group $R^6$ represents H, or $C_{1-6}$-alkyl; or $R^6$ represents an aryl, preferably phenyl, bonded via a $C_{1-3}$-alkylene group. In this context, the groups $C_{1-6}$-alkyl, $C_{1-3}$-alkylene and aryl mentioned above in connection with $R^6$ can in each case be unsubstituted or substituted once or several times by identical or different substituents. For example, the aryl can in each case be unsubstituted or substituted once or several times, for example 2, 3, 4 or 5 times, by identical or different substituents selected from the group consisting of O—$C_{1-3}$-alkyl, unsubstituted $C_{1-6}$-alkyl, F, Cl, Br, I, $CF_3$, $OCF_3$, OH and SH.

In a further preferred embodiment of the substituted sulfonamide compounds according to the invention, the group $R^7$ represents $C_{1-6}$-alkyl, in particular methyl, ethyl, propyl and iso-propyl, n-butyl, sec-butyl, iso-butyl or t-butyl; or $R^7$ represents $C_{4-7}$-cycloalkyl, in particular cyclopentyl and cyclohexyl; or $R^7$ denotes aryl, in particular phenyl or naphthyl, or represents a 5- to 6-membered heteroaryl containing 1 to 3 hetero atoms selected from the group consisting of N, O, S, in particular 2-, 3- or 4-pyridinyl; or $R^7$ represents a $C_{4-6}$-cycloalkyl, in particular cyclopentyl and cyclohexyl, bonded via a $C_{1-3}$-alkylene group, an aryl, in particular phenyl or naphthyl, bonded via a $C_{1-3}$-alkylene group, or a 5- to 6-membered heteroaryl containing 1 to 3 hetero atoms selected from the group consisting of N, O, S, in particular 2-, 3- or 4-pyridinyl, bonded via a $C_{1-3}$-alkylene group, wherein all the abovementioned $C_{1-6}$-alkyl, $C_{4-7}$-cycloalkyl, aryl or heteroaryl groups can in each case be unsubstituted or substituted once or several times by identical or different substituents. For example, the aryl or heteroaryl can in each case be unsubstituted or substituted once or several times, for example 2, 3, 4 or 5 times, by identical or different substituents selected from the group consisting of O—$C_{1-3}$-alkyl, unsubstituted $C_{1-6}$-alkyl, F, Cl, Br, I, $CF_3$, $OCF_3$, OH and SH.

In a further preferred embodiment of the substituted sulfonamide compounds according to the invention, the groups $R^6$ and $R^7$, with inclusion of the N—C(=O) group, form a ring of the type

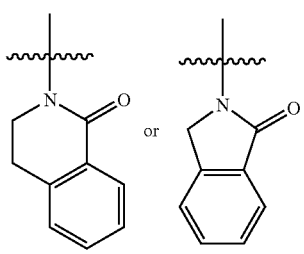

wherein the annellated benzo group can in each case be unsubstituted or substituted at least once by substituents which, independently of one another, are selected from the group consisting of $C_{1-6}$-alkyl, $C_{1-6}$-alkyl-O—, F, Cl, Br, I, $CF_3$, $OCF_3$, OH and SH.

In a further preferred embodiment of the substituted sulfonamide compounds according to the invention, $R^2$ represents H, $C_{1-6}$-alkyl; $C_{3-8}$-cycloalkyl, in particularly $C_{3-6}$-cycloalkyl, or $R^2$ represents aryl or heteroaryl; or $R^2$ represents a $C_{3-6}$-cycloalkyl, aryl or heteroaryl bonded via a $C_{1-6}$-alkylene group, $C_{2-6}$-alkenylene group or $C_{2-6}$-alkynylene group. In this context, the radicals $C_{1-6}$-alkyl, $C_{3-6}$-cycloalkyl, $C_{2-6}$-alkylene, $C_{2-6}$-alkenylene, $C_{2-6}$-alkynylene, aryl and heteroaryl mentioned above in connection with $R^2$ can in each case be unsubstituted or substituted once or several times by identical or different substituents. In particular, the aryl or heteroaryl can in each case be unsubstituted or substituted once or several times by identical or different substituents, wherein the radicals are chosen, for example, from the group consisting of $C_{1-6}$-alkyl, $C_{1-6}$-alkyl-O—, F, Cl, Br, I, $CF_3$, $OCF_3$, OH and SH.

In particular, $R^2$ represents H, methyl, ethyl, propyl and iso-propyl; n-butyl, sec-butyl, iso-butyl, t-butyl or cyclopropyl; or $R^2$ denotes phenyl or 2-, 3- or 4-pyridinyl; or a cyclopropyl, phenyl or 2-, 3- or 4-pyridinyl bonded via a $C_{1-6}$-alkylene group, wherein the phenyl or 2-, 3- or 4-pyridinyl is each case unsubstituted or substituted once or several times by identical or different substituents and the radicals are selected from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH.

In a further preferred embodiment of the sulfonamide compounds according to the invention, $R^3$ represents H, $C_{1-6}$-alkyl, in particular methyl, ethyl, n-propyl, iso-propyl, n-butyl, iso-butyl, sec-butyl, tert-butyl; or $R^3$ represents aryl or heteroaryl or an aryl or heteroaryl bonded via a $C_{1-6}$-alkylene group, $C_{2-6}$-alkenylene group or $C_{2-6}$-alkynylene group. In this context, the radicals $C_{1-6}$-alkyl, $C_{3-6}$-cycloalkyl, $C_{2-6}$-alkylene, $C_{2-6}$-alkenylene, $C_{2-6}$-alkynylene, aryl and heteroaryl mentioned above in connection with $R^3$ can in each case be unsubstituted or substituted once or several times by identical or different substituents. In particular, the aryl or heteroaryl can in each case be unsubstituted or substituted once or several times by identical or different substituents, wherein the radicals are selected from the group consisting of $C_{1-6}$-alkyl, $C_{1-6}$-alkyl-O—, F, Cl, Br, I, $CF_3$, $OCF_3$, OH and SH. In particular, $R^3$ represents H, phenyl or 2-, 3- or 4-pyridinyl, wherein the phenyl or 2-, 3- or 4-pyridinyl is each case unsubstituted or substituted once or several times by identical or different substituents, wherein the radicals are selected from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH.

In a further preferred embodiment of the compounds according to the invention, $R^2$ represents H or methyl and $R^3$ represents H or phenyl, wherein phenyl is in each case unsubstituted or substituted once or several times by identical or different substituents, and the radicals are selected from the group consisting of methyl, methoxy, F, Cl, Br, I, $CF_3$, $OCF_3$ and OH.

In a further preferred embodiment, the heterocyclic ring formed by $R^2$ and $R^3$ is a saturated 4-, 5-, 6- or 7-membered heterocyclic ring which can be fused with an aryl or heteroaryl radical and, apart from the N atom to which $R^2$ is bonded, contains no further hetero atom.

In a further preferred embodiment, the sulfonamide compounds according to the invention are compounds corresponding to formula Ia:

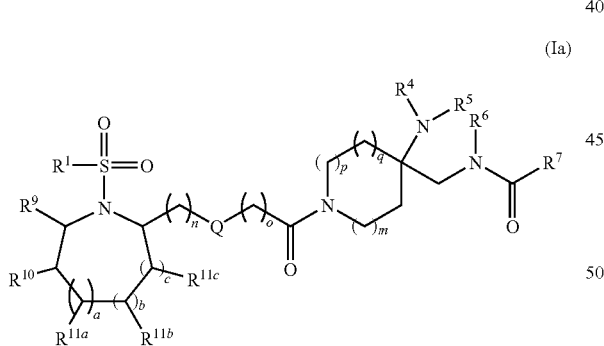

(Ia)

wherein a, b and c each independently represent 0 or 1;

$R^9$, $R^{10}$, $R^{11a}$, $R^{11b}$ and $R^{11c}$ each independently represent H or two vicinal groups from $R^9$, $R^{10}$, $R^{11a}$, $R^{11b}$ and $R^{11c}$ form a 5- or 6-membered annellated aryl or heteroaryl group, which can be unsubstituted or substituted once or several times by identical or different substituents. In this context, the groups $R^1$, $R^4$, $R^5$, $R^6$ and $R^7$ as well as Q, n, o, p, q and r defined in the general formula Ia can likewise assume the particular specific meanings described above in connection with the preferred embodiments of the substituted sulfonamide compounds according to the invention. Preferably, two of the vicinal radicals from $R^9$, $R^{10}$, $R^{11a}$, $R^{11b}$ and $R^{11c}$ form an annellated benzene ring, which is unsubstituted or substituted once or several times, wherein the substituents are preferably selected from the group consisting of methyl, methoxy, $CF_3$, F, Cl and Br.

Those skilled in the art understand that the following partial structures of formula Ia

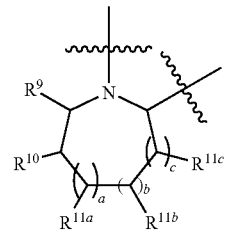

can assume the following forms when a b and c have the values 0 and/or 1:

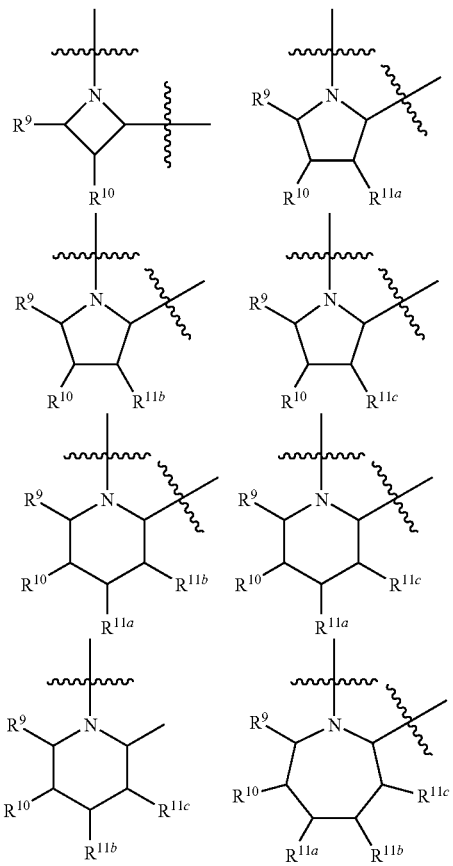

Persons skilled in the art furthermore understand that if two vicinal (adjacent) radicals from $R^9$, $R^{10}$, $R^{11a}$, $R^{11b}$ and $R^{11c}$ form an annellated ring which is aromatic or is unsaturated on one or both of the carbon atoms linked with the vicinal radicals, this/these carbon atom(s) can no longer carry a hydrogen atom.

For example, the following form thus results for a partial structure in which one of the indices a, b or c=0 and the other two each=1 and the adjacent radicals $R^9$ and $R^{10}$ form an annellated benzene ring:

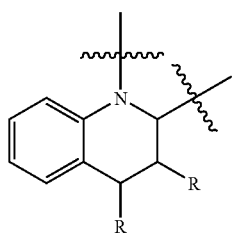

wherein R represents the corresponding radical from $R^{11a}$, $R^{11b}$ and $R^{11c}$.

The following form results for a part structure in which one of the indices a, b or c=0 and the other two are each=1 and the adjacent radicals $R^{10}$ and $R^{11a}$ or $R^{11b}$ form an annellated benzene ring:

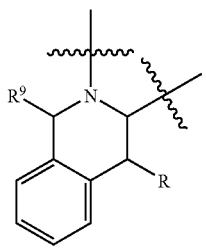

wherein R represents the corresponding radical from $R^{11b}$ or $R^{11c}$.

The following form results for a part structure in which one of the indices a, b or c=0 and the other two each=1 and two adjacent radicals from $R^{11a}$, $R^{11b}$ and/or $R^{11c}$ form an annellated benzene ring:

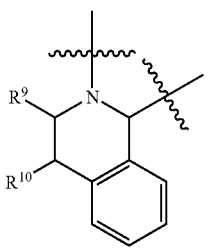

If the ring size of the part structures described above allow, i.e. for compounds in which a+b+c=2 or 3, in each case two pairs of adjacent radicals can also form an annellated ring, for example:

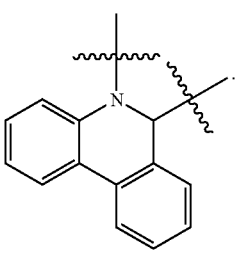 [SMILES: *C1c2ccccc2-c2ccccc2N1*]

In a further preferred embodiment, the substituted sulfonamide compounds according to the invention are compounds of formula Ib

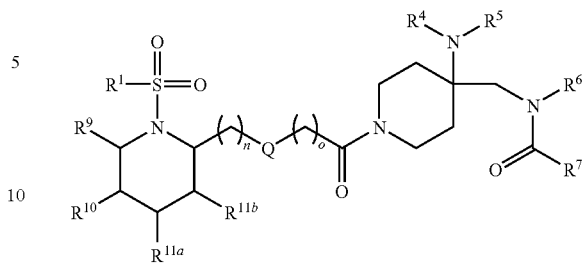

(Ib)

wherein $R^9$, $R^{10}$, $R^{11a}$ and $R^{11b}$ each independently represent H or two vicinal radicals from $R^9$, $R^{10}$, $R^{11a}$ or $R^{11b}$ form a 5- or 6-membered annellated aryl or heteroaryl radical, preferably an annellated benzene ring, which is unsubstituted or substituted once or several times, wherein the substituents are selected from the group consisting of methyl, methoxy, $CF_3$, F, Cl and Br. In this context, the radicals $R^1$, $R^4$, $R^5$, $R^6$ and $R^7$ as well as Q, n and o defined in the general formula Ib can likewise assume the particular specific meanings described above in connection with the preferred embodiments of the substituted sulfonamide compounds according to the invention.

In a further preferred embodiment of the present invention, the substituted sulfonamide compounds have the general formula Ic

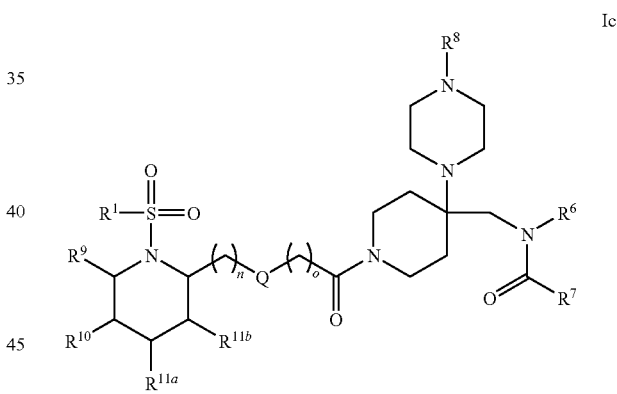

Ic wherein n represents 0, 1 or 2; preferably 0 or 1;

o represents 1, 2 or 3, preferably 1;

Q represents a single bond, —$CH_2$— or —O—, preferably a single bond, or —O—;

$R^1$ represents aryl or heteroaryl or denotes an aryl or heteroaryl bonded via a $C_{1-3}$-alkylene group;

$R^6$ represents H, $C_{1-6}$-alkyl, or a $C_{3-8}$cycloalkyl bonded via a $C_{1-3}$-alkylene group, an aryl bonded via a $C_{1-3}$-alkylene group or a heteroaryl bonded via a $C_{1-3}$-alkylene group, $R^7$ represents $C_{1-6}$-alkyl, $C_{2-6}$-alkenyl or $C_{2-6}$-alkynyl, $C_{3-8}$cycloalkyl, aryl or heteroaryl; or denotes a $C_{3-8}$-cycloalkyl, aryl or heteroaryl bonded via a $C_{1-6}$-alkylene group, or $R^6$ and $R^7$ together with the —N—C(=O) group, form a ring of the type

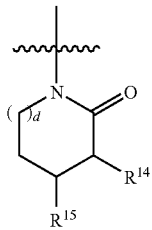

wherein d represents 0 or 1 and $R^{14}$ and $R^{15}$ together represent an annellated unsubstituted or substituted aryl or heteroaryl radical;

$R^8$ represents H, $C_{1-6}$-alkyl, $C_{3-8}$cycloalkyl, aryl, heteroaryl or represents a $C_{3-8}$-cycloalkyl, aryl or heteroaryl bonded via a $C_{1-6}$-alkylene group;

$R^9$, $R^{10}$, $R^{11a}$ and $R^{11b}$ each independently represent H or two vicinal groups selected from $R^9$, $R^{10}$, $R^{11a}$ and $R^{11b}$ form a 5- or 6-membered annellated aryl or heteroaryl radical, which can be unsubstituted or substituted once or several times by identical or different substituents;

wherein the abovementioned groups $C_{1-6}$-alkyl, $C_{1-6}$-alkylene, $C_{2-6}$-alkenylene, $C_{2-6}$-alkynylene, $C_{3-8}$-cycloalkyl, aryl and heteroaryl can in each case be unsubstituted or substituted once or several times by identical or different substituents and the abovementioned groups $C_{1-6}$-alkyl, $C_{1-6}$-alkylene, $C_{2-6}$-alkenylene and $C_{2-6}$-alkynylene can in each case be branched or unbranched; in the form of an individual enantiomer or of an individual diastereomer, of the racemate, of the enantiomers, of the diastereomers, mixtures of the enantiomers and/or diastereomers, and in each case in the form of their bases and/or physiologically acceptable salts; and wherein a substituted alkyl, alkenyl, alkylene, alkenylene, alkynylene or cycloalkyl is substituted once or several times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl, and a substituted aryl or heteroaryl is substituted once or several times by identical or different substituents selected from the group consisting of F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—, unsubstituted $C_{1-6}$-alkyl, pyrrolidinyl, imidazolyl, piperidinyl, benzyloxy, phenoxy, phenyl, pyridinyl, —$C_{1-3}$-alkylene-aryl$^1$, benzyl, thienyl and furyl, wherein aryl$^1$ represents phenyl, furyl, thienyl or pyridinyl.

In this context, in further embodiments the radicals defined in the general formula Ic, that is to say $R^1$, $R^6$, $R^7$, $R^8$, $R^9$, $R^{10}$, $R^{11a}$ and $R^{11b}$, and n and o in further embodiments can likewise assume the particular specific meanings described above in connection with the embodiments of the substituted sulfonamide compounds according to the invention.

In a further preferred embodiment of the present invention, the substituted sulfonamide compounds have the general formula Id

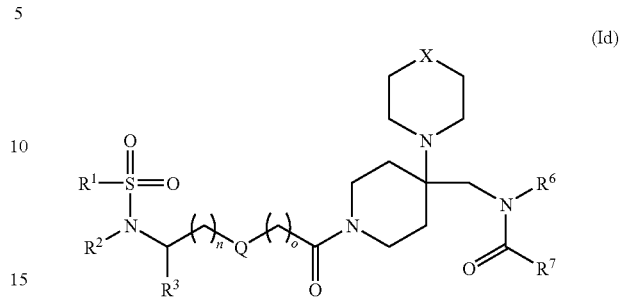

wherein
n represents 0, 1 or 2, preferably 0 or 1, particularly 1;
o represents 1, 2 or 3, preferably 1;
Q represents a single bond, —O— or —$CH_2$—, preferably a single bond or —O—;
X represents $NR^8$ or C(halogen)$_2$;
$R^1$ represents aryl or heteroaryl or denotes an aryl or heteroaryl bonded via a $C_{1-3}$-alkylene group;
$R^2$ represents H, $C_{1-6}$-alkyl, $C_{3-8}$cycloalkyl, aryl or heteroaryl; or denotes a $C_{3-8}$-cycloalkyl, aryl or heteroaryl bonded via a $C_{1-6}$-alkylene group, $C_{2-6}$-alkenylene group or $C_{2-6}$-alkynylene group;
$R^3$ represents H, $C_{1-6}$-alkyl, aryl or heteroaryl; or denotes an aryl or heteroaryl bonded via a $C_{1-6}$-alkylene group, $C_{2-6}$-alkenylene group or $C_{2-6}$-alkynylene group;
$R^6$ represents H, $C_{1-6}$-alkyl or a $C_{3-8}$cycloalkyl bonded via a $C_{1-3}$-alkylene group, an aryl bonded via a $C_{1-3}$-alkylene group or a heteroaryl bonded via a $C_{1-3}$-alkylene group,
$R^7$ represents $C_{1-6}$-alkyl, $C_{2-6}$-alkenyl or $C_{2-6}$-alkynyl, $C_{3-8}$cycloalkyl, aryl or heteroaryl; or denotes a $C_{3-8}$-cycloalkyl, aryl or heteroaryl bonded via a $C_{1-6}$-alkylene group, or
$R^6$ and $R^7$ together with —N—C(=O) group, form a ring of the type

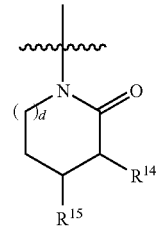

wherein d represents 0 or 1 and $R^{14}$ and $R^{15}$ together represent an annellated unsubstituted or substituted aryl or heteroaryl group;

$R^8$ represents H, $C_{1-6}$-alkyl, $C_{3-8}$-cycloalkyl, aryl, heteroaryl; or represents a $C_{3-8}$-cycloalkyl, aryl or heteroaryl bonded via a $C_{1-6}$-alkylene group;

wherein the abovementioned groups $C_{1-6}$-alkyl, $C_{1-6}$-alkylene, $C_{2-6}$-alkenylene, $C_{2-6}$-alkynylene, $C_{3-8}$-cycloalkyl, aryl and heteroaryl can in each case be unsubstituted or substituted once or several times by identical or different substituents and the abovementioned radicals $C_{1-6}$-alkyl, $C_{1-6}$-alkylene, $C_{2-6}$-alkenylene and $C_{2-6}$-alkynylene can in each case be branched or unbranched; in the form of an individual enantiomer or of an individual diastereomer, of the racemate, of the enantiomers, of the diastereomers, mixtures of the enantiomers and/or diastereomers, and in each case in the form of their bases and/or physiologically acceptable salts;

A substituted alkyl, alkenyl, alkylene, alkenylene, alkynylene or cycloalkyl is substituted once or several times by identical or different substituents selected from the group consisting of F, Cl, Br, I, CN, $NH_2$, $NH$—$C_{1-6}$-alkyl, $NH$—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl and benzyl. Substituted aryl or heteroaryl is substituted once or several times by identical or different substituents selected from the group consisting of F, Cl, Br, I, CN, $NH_2$, $NH$—$C_{1-6}$-alkyl, $NH$—$C_{1-6}$-alkylene-OH, $N(C_{1-6}$-alkyl$)_2$, $N(C_{1-6}$-alkylene-OH$)_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl, pyrrolidinyl, imidazolyl, piperidinyl, benzyloxy, phenoxy, phenyl, pyridinyl, —$C_{1-3}$-alkylene-aryl$^1$, benzyl, thienyl and furyl, wherein aryl$^1$ represents phenyl, furyl, thienyl or pyridinyl.

In this context, in further embodiments the groups defined in the general formula Id, that is to say $R^1$, $R^2$, $R^3$, $R^6$, $R^7$ and $R^8$, and n and o in further embodiments can likewise assume the particular specific meanings described above in connection with the embodiments of the substituted sulfonamide compounds according to the invention.

In further preferred embodiments of the sulfonamide compounds of the invention, these are compounds of the general formulas Ie, If, Ig, Ih and Ii:

(Ie)

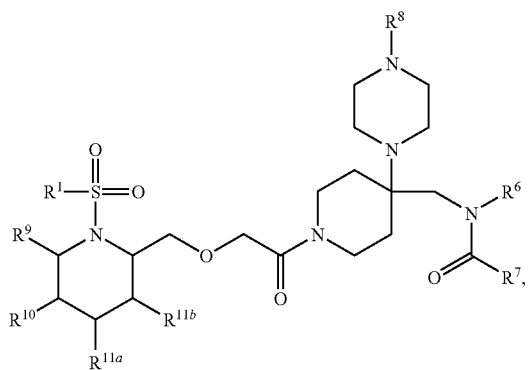

(If)

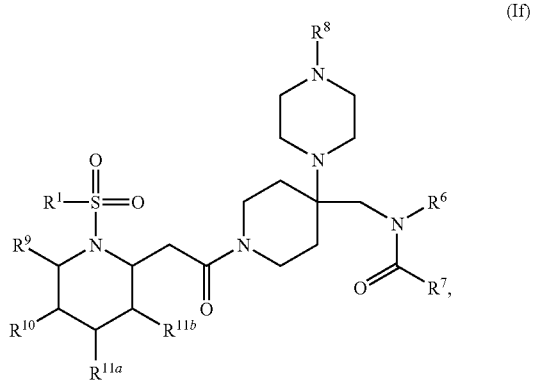

(Ig)

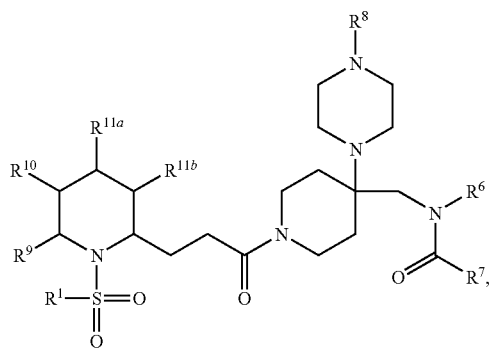

(Ih)

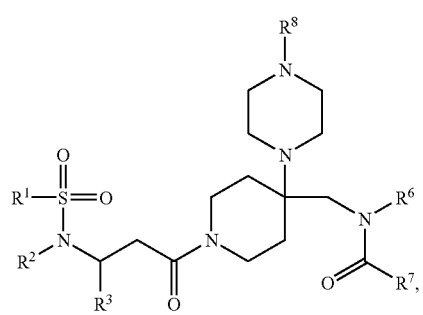

(Ii)

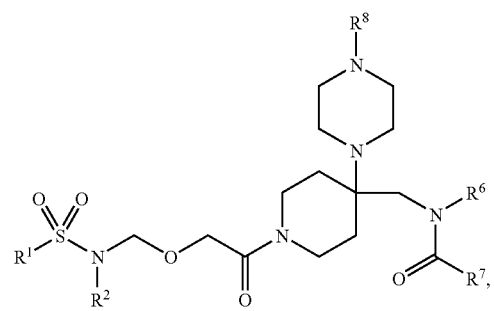

wherein the groups defined in the formulas Ie, If, Ig, Ih and Ii, that is to say $R^1$, $R^2$, $R^3$, $R^6$, $R^7$, $R^8$, $R^9$, $R^{10}$, $R^{11a}$ and $R^{11b}$, can likewise assume the particular specific meanings described above in connection with the embodiments of the substituted sulfonamide compounds according to the invention.

In further preferred embodiments of the substituted sulfonamide compounds of the invention, in the compounds of formulas Ie, If, Ig, Ih and Ii:

$R^1$ represents phenyl or naphthyl, wherein the phenyl or naphthyl is unsubstituted or substituted once or several times, for example 2, 3, 4 or 5 times, by identical or different substituents selected from the group consisting of methyl, methoxy, $CF_3$, $OCF_3$, F, Cl and Br; in particular $R^1$ represents 4-methoxy-2,6-dimethylphenyl, 3,4-dichlorophenyl, 4-chloro-2,5-methylphenyl or 2,4,6-trimethylphenyl, preferably 4-methoxy-2,6-dimethylphenyl;

$R^2$ represents H or methyl;

$R^3$ represents H or phenyl, wherein phenyl is in each case unsubstituted or substituted once or several times by identical or different substituents, and the radicals are selected from the group consisting of methyl, methoxy, F, Cl, Br, I, $CF_3$, $OCF_3$ and OH;

$R^6$ represents H, $C_{1-6}$-alkyl, in particular methyl, ethyl, n-propyl, iso-propyl, n-butyl, iso-butyl, sec-butyl or tert-butyl;

$R^7$ represents $C_{1-6}$-alkyl, in particular methyl, ethyl, propyl and iso-propyl, n-butyl, iso-butyl, sec-butyl, tert-butyl, phenyl, naphthyl, 2-, 3- or 4-pyridinyl, benzyl or phenylethyl, wherein the aromatic or heteroaromatic groups can in each case be unsubstituted or substituted once or several times, for example 2, 3, 4 or 5 times, by identical or different substituents selected from the group consisting of O—$C_{1-3}$-alkyl, unsubstituted $C_{1-6}$-alkyl, F, Cl, Br, I, $CF_3$, $OCF_3$, OH and SH;

$R^8$ represents H, $C_{1-6}$-alkyl, in particular methyl, ethyl, n-propyl, iso-propyl, n-butyl, iso-butyl, sec-butyl, tert-butyl; or $R^8$ represents phenyl, naphthyl, 2-, 3- or 4-pyridinyl; represents an aryl, preferably benzyl or phenylethyl, bonded via a $C_{1-3}$-alkylene group; or represents a heteroaryl, preferably 2-, 3- or 4-pyridinyl, bonded via a $C_{1-3}$-alkylene group; wherein the aryl or heteroaryl can in each case be unsubstituted or substituted once or several times, for example 2, 3, 4 or 5 times, by identical or different substituents selected from the group consisting of O—$C_{1-3}$-alkyl, unsubstituted $C_{1-6}$-alkyl, F, Cl, Br, I, $CF_3$, $OCF_3$, OH and SH; and $R^9$, $R^{10}$, $R^{11a}$ and $R^{11b}$ each independently represent H or two vicinal radicals from $R^9$, $R^{10}$, $R^{11a}$ and $R^{11b}$, preferably $R^9$ and $R^{10}$, form a benzo group, which can be unsubstituted or substituted once or several times, wherein the substituents are selected from the group consisting of methyl, methoxy, $CF_3$, F, Cl and Br.

In a further preferred embodiment of the present invention, the sulfonamide compounds according to the invention are selected from the group consisting of:

(1) N-((1-(2-(2-(4-methoxy-N,2,6-trimethylphenylsulfonamido)ethoxy)acetyl)-4-(4-methylpiperazin-1-yl)piperidin-4-yl)methyl)isonicotinamide;
(2) N-((1-(3-(1-(4-chloro-2,5-dimethylphenylsulfonyl)piperidin-2-yl)propanoyl)-4-(4-methylpiperazin-1-yl)piperidin-4-yl)methyl)acetamide;
(3) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)-2-phenylacetamide;
(4) N-((4-(4-methylpiperazin-1-yl)-1-(2-(1-(3-(trifluoromethyl)phenylsulfonyl)piperidin-2-yl)acetyl)piperidin-4-yl)methyl)-2-phenylacetamide;
(5) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)benzamide;
(6) N-((1-(3-(1-(4-chloro-2,5-dimethylphenylsulfonyl)piperidin-2-yl)propanoyl)-4-(4-methylpiperazin-1-yl)piperidin-4-yl)methyl)benzamide;
(7) N-((1-(2-(((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)acetamide;
(8) N-((4-(4-methylpiperazin-1-yl)-1-(3-(naphthalene-2-sulfonamido)-3-phenylpropanoyl)piperidin-4-yl)methyl)-2-phenylacetamide;
(9) N-((1-(3-(1-(4-chloro-2,5-dimethylphenylsulfonyl)piperidin-2-yl)propanoyl)-4-(4-methylpiperazin-1-yl)piperidin-4-yl)methyl)picolinamide;
(10) N-((1-(3-(1-(4-chloro-2,5-dimethylphenylsulfonyl)piperidin-2-yl)propanoyl)-4-(4-methylpiperazin-1-yl)piperidin-4-yl)methyl)-2-phenylacetamide;
(11) N-((1-(3-(1-(4-chloro-2,5-dimethylphenylsulfonyl)piperidin-2-yl)propanoyl)-4-(4-(pyridin-4-yl)piperazin-1-yl)piperidin-4-yl)methyl)acetamide;
(12) N-((4-(4-methylpiperazin-1-yl)-1-(2-(1-(3-(trifluoromethyl)phenylsulfonyl)-piperidin-2-yl)acetyl)piperidin-4-yl)methyl)acetamide;
(13) N-((1-(2-(((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)-2-phenylacetamide;
(14) N-((1-(3-(naphthalene-2-sulfonamido)-3-phenylpropanoyl)-4-(4-(pyridin-4-yl)piperazin-1-yl)piperidin-4-yl)methyl)acetamide;
(15) N-((1-(2-(2-(4-methoxy-N,2,6-trimethylphenylsulfonamido)ethoxy)acetyl)-4-(4-methylpiperazin-1-yl)piperidin-4-yl)methyl)-2-phenylacetamide;
(16) N-((4-(4-methylpiperazin-1-yl)-1-(3-(naphthalene-2-sulfonamido)-3-phenylpropanoyl)piperidin-4-yl)methyl)benzamide;
(17) N-((1-(2-(((1-(3,4-dichlorophenylsulfonyl)-1,2,3,4-tetrahydroquinolin-2-yl)methoxy)acetyl)-4-(4-(pyridin-4-yl)piperazin-1-yl)piperidin-4-yl)methyl)acetamide;
(18) N-((4-(4-methylpiperazin-1-yl)-1-(2-(1-(3-(trifluoromethyl)phenylsulfonyl)-piperidin-2-yl)acetyl)piperidin-4-yl)methyl)picolinamide;
(19) N-((4-(4-methylpiperazin-1-yl)-1-(3-(naphthalene-2-sulfonamido)-3-phenylpropanoyl)piperidin-4-yl)methyl)picolinamide;
(20) N-((1-(2-(((1-(3,4-dichlorophenylsulfonyl)-1,2,3,4-tetrahydroquinolin-2-yl)-methoxy)acetyl)-4-(4-methylpiperazin-1-yl)piperidin-4-yl)methyl)picolinamide;
(21) N-((1-(2-(((1-(4-methoxy-2,6-dimethylphenylsulfonyl)piperidin-2-yl)methoxy)acetyl)-4-(4-methylpiperazin-1-yl)piperidin-4-yl)methyl)picolinamide;
(22) N-((1-(2-((1-(4-methoxy-2,6-dimethylphenylsulfonyl)piperidin-2-yl)methoxy)acetyl)-4-(4-(pyridin-4-yl)piperazin-1-yl)piperidin-4-yl)methyl)acetamide;
(23) N-((1-(2-(((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)benzamide;
(24) N-((1-(2-(2-(4-methoxy-N,2,6-trimethylphenylsulfonamido)ethoxy)acetyl)-4-(4-methylpiperazin-1-yl)piperidin-4-yl)methyl)benzamide;
(25) N-((1-(2-(2-(4-methoxy-N,2,6-trimethylphenylsulfonamido)ethoxy)acetyl)-4-(4-methylpiperazin-1-yl)piperidin-4-yl)methyl)picolinamide;
(26) N-((1-(3-(1-(4-chloro-2,5-dimethylphenylsulfonyl)piperidin-2-yl)propanoyl)-4-(4-methylpiperazin-1-yl)piperidin-4-yl)methyl)isonicotinamide;
(27) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)acetamide;
(28) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)-isonicotinamide;
(29) N-((4-(4-methylpiperazin-1-yl)-1-(2-(1-(3-(trifluoromethyl)phenylsulfonyl)-piperidin-2-yl)acetyl)piperidin-4-yl)methyl)isonicotinamide;
(30) N-((1-(2-(((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)-isonicotinamide;
(31) N-((1-(2-(2-(4-methoxy-N,2,6-trimethylphenylsulfonamido)ethoxy)acetyl)-4-(4-methylpiperazin-1-yl)piperidin-4-yl)methyl)acetamide;
(32) N-((1-(2-(2-(4-methoxy-N,2,6-trimethylphenylsulfonamido)ethoxy)acetyl)-4-(4-methylpiperazin-1-yl)piperidin-4-yl)methyl)nicotinamide;
(33) N-((1-(3-(1-(4-chloro-2,5-dimethylphenylsulfonyl)piperidin-2-yl)propanoyl)-4-(4-methylpiperazin-1-yl)piperidin-4-yl)methyl)nicotinamide;
(34) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)nicotinamide;
(35) N-((4-(4-methylpiperazin-1-yl)-1-(3-(naphthalene-2-sulfonamido)-3-phenylpropanoyl)piperidin-4-yl)methyl)acetamide;

(36) N-((4-(4-(pyridin-4-yl)piperazin-1-yl)-1-(2-(1-(3-(trifluoromethyl)phenyl-sulfonyl)piperidin-2-yl)acetyl)piperidin-4-yl)methyl)acetamide;
(37) N-((4-(4-methylpiperazin-1-yl)-1-(3-(naphthalene-2-sulfonamido)-3-phenylpropanoyl)piperidin-4-yl)methyl) isonicotinamide;
(38) N-((4-(4-methylpiperazin-1-yl)-1-(3-(naphthalene-2-sulfonamido)-3-phenylpropanoyl)piperidin-4-yl)methyl) nicotinamide;
(39) N-((4-(4-methylpiperazin-1-yl)-1-(2-(1-(3-(trifluoromethyl)phenylsulfonyl)-piperidin-2-yl)acetyl)piperidin-4-yl)methyl)nicotinamide;
(40) N-((1-(2-((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)nicotinamide;
(41) N-((1-(2-(2-(4-methoxy-N,2,6-trimethylphenylsulfonamido)ethoxy)acetyl)-4-(4-(pyridin-4-yl)piperazin-1-yl) piperidin-4-yl)methyl)acetamide;
(42) N-Cyclopropyl-N-(2-(2-(4-(4-cyclopropylpiperazin-1-yl)-4-((1-oxoisoindolin-2-yl)methyl)piperidin-1-yl)-2-oxoethoxy)ethyl)-4-methoxy-2,6-dimethylbenzene-sulfonamide;
(43) N-((1-(2-(2-(2-Chloro-N-cyclopropyl-6-methylphenylsulfonamido)ethoxy)-acetyl)-4-(4-cyclopropylpiperazin-1-yl)piperidin-4-yl)methyl)-isonicotinamide;
(44) N-((1-(2-(2-(N-Cyclopropyl-4-methoxy-2,6-dimethylphenylsulfonamido)ethoxy)acetyl)-4-(4-cyclopropylpiperazin-1-yl)piperidin-4-yl)methyl)isonicotinamide;
(45) (S)—N-((4-(4-Cyclopropylpiperazin-1-yl)-1-(2-((1-(4-methoxy-2,6-dimethylphenylsulfonyl)indolin-2-yl)methoxy)acetyl)piperidin-4-yl)methyl)isonicotinamide;
(46) N-((1-(2-(2-(N-Cyclopropyl-4-methoxy-2,6-dimethylphenylsulfonamido)ethoxy)acetyl)-4-(4-(pyridin-4-yl) piperazin-1-yl)piperidin-4-yl)methyl)acetamide;
(47) N-((1-(2-(2-(N-Cyclopropyl-2-(trifluoromethyl)phenylsulfonamido)ethoxy)acetyl)-4-(4-cyclopropylpiperazin-1-yl)piperidin-4-yl)methyl)isonicotinamide;
(48) N-((1-(2-(2-(4-Methoxy-N,2,6-trimethylphenylsulfonamido)ethoxy)acetyl)-4-(4-methylpiperazin-1-yl)piperidin-4-yl)methyl)isonicotinamide hydrochloride;
(49) N-((1-(2-((4-(4-Methoxy-2,6-dimethylphenylsulfonyl)-3,4-dihydro-2H-benzo[b][1,4]oxazin-3-yl)methoxy) acetyl)-4-(4-methylpiperazin-1-yl)piperidin-4-yl)methyl) isonicotinamide
(50) N-((1-(2-((4-(2-Chloro-6-methylphenylsulfonyl)-3,4-dihydro-2H-benzo[b][1,4]oxazin-3-yl)methoxy)acetyl)-4-(4-methylpiperazin-1-yl)piperidin-4-yl)methyl)isonicotinamide
(51) N-((1-(2-(2-(4-Methoxy-N,2,3,6-tetramethylphenylsulfonamido)ethoxy)acetyl)-4-(4-methylpiperazin-1-yl)piperidin-4-yl)methyl)isonicotinamide
(52) N-((1-(3-((1-(4-Methoxy-2,6-dimethylphenylsulfonyl) piperidin-2-yl)methoxy)propanoyl)-4-(4-methylpiperazin-1-yl)piperidin-4-yl)methyl)isonicotinamide
(53) N-((1-(2-(2-(1-(4-Methoxy-2,6-dimethylphenylsulfonyl)piperidin-2-yl)ethoxy)acetyl)-4-(4-methylpiperazin-1-yl)piperidin-4-yl)methyl)isonicotinamide
(54) N-((1-(4-(N-Methyl-3-(trifluoromethyl)phenylsulfonamido)butanoyl)-4-(4-methylpiperazin-1-yl)piperidin-4-yl)methyl)isonicotinamide in the form of an individual enantiomer or of an individual diastereomer, of the racemate, of the enantiomers, of the diastereomers, of the mixtures of the enantiomers and/or diastereomers, of the bases and/or salts of physiologically acceptable acids.

The numbering of the individual embodiments of the compounds according to the invention used above is retained in the following explanations of the present invention, in particular in the description of the examples.

The compounds according to the invention preferably have an antagonistic action on the human B1R receptor or the B1R receptor of the rat. In a preferred embodiment of the invention, the compounds according to the invention have an antagonistic action both on the human B1R receptor (hB1R) and on the B1R receptor of the rat (rB1R). Compounds which show an inhibition of at least 15%, 25%, 50%, 70%, 80% or 90% on the human B1R receptor and/or on the B1R receptor of the rat in the FLIPR assay at a concentration of 10 µm are particularly preferred. Compounds which show an inhibition on the human B1R receptor and on the B1R receptor of the rat of at least 70%, in particular of at least 80% and particularly preferably of at least 90% at a concentration of 10 µm are very particularly preferred.

The agonistic or antagonistic action of substances can be quantified on the bradykinin 1 receptor (B1R) of the human and rat species with ectopically expressing cell lines (CHO K1 cells) and with the aid of a $Ca^{2+}$-sensitive dyestuff (Fluo-4) in a fluorescent imaging plate reader (FLIPR). The figure in % activation is based on the $Ca^{2+}$ signal after addition of Lys-Des-Arg$^9$-bradykinin (0.5 nM) or Des-Arg$^9$-bradykinin (100 nM). Antagonists lead to a suppression of the $Ca^{2+}$ inflow after addition of the agonist. % inhibition compared with the maximum achievable inhibition is stated.

The substances according to the invention can act, for example, on the B1R relevant in connection with various diseases, so that they are suitable as a pharmaceutical active compound in pharmaceutical compositions. The invention therefore also provides pharmaceutical compositions containing at least one substituted sulfonamide compound according to the invention and optionally suitable additives and/or auxiliary substances and/or optionally further active compounds. The pharmaceutical compositions according to the invention optionally contain, in addition to at least one substituted sulfonamide compound according to the invention, suitable additives and/or auxiliary substances, that is to say also carrier materials, fillers, solvents, diluents, dyestuffs and/or binders, and can be administered as liquid pharmaceutical composition forms in the form of injection solutions, drops or juices or as semi-solid pharmaceutical composition forms in the form of granules, tablets, pellets, patches, capsules, plasters/spray-on plasters or aerosols. The choice of auxiliary substances etc. and the amounts thereof to be employed depend on whether the pharmaceutical composition is to be administered orally, perorally, parenterally, intravenously, intraperitoneally, intradermally, intramuscularly, nasally, buccally, rectally or topically, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Sulfonamide compounds according to the invention in a depot, in dissolved form or in a plaster, optionally with the addition of agents which promote penetration through the skin, are suitable formulations for percutaneous administration. Formulation forms which can be used orally or percutaneously can release the substituted sulfonamide compounds according to the invention in a delayed manner. The substituted sulfonamide compounds according to the invention can also be used in parenteral long-term depot forms, such as e.g. implants or implanted pumps. In principle, other further active compounds known to persons skilled in the art can be added to the pharmaceutical compositions according to the invention.

The amount of active compound to be administered to patients varies as a function of the weight of the patient, the mode of administration, the indication and the severity of the disease. 0.00005 to 50 mg/kg, preferably 0.01 to 5 mg/kg of at least one substituted sulfonamide compound according to the invention are conventionally administered.

In a preferred form of the pharmaceutical composition, a substituted sulfonamide compound according to the invention contained therein is present as the pure diastereomer and/or enantiomer, as a racemate or as a non-equimolar or equimolar mixture of the diastereomers and/or enantiomers.

B1R is involved in particular in the pain event. The substituted sulfonamide compounds according to the invention can accordingly be used for the preparation of a pharmaceutical composition for treatment of pain, in particular acute, visceral, neuropathic or chronic pain.

The invention therefore also provides the use of a substituted sulfonamide compound according to the invention for the preparation of a pharmaceutical composition for treatment of pain, in particular acute, visceral, neuropathic or chronic pain. Furthermore, the invention provides the use of a substituted sulfonamide compound according to the invention for the preparation of a pharmaceutical composition for the treatment of inflammatory pain.

The invention also provides a method of using a substituted sulfonamide compound according to the invention for the preparation of a pharmaceutical composition for treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiogenesis inhibitor. In this context, in one of the above uses it may be preferable for a substituted sulfonamide compound which is used to be present as the pure diastereomer and/or enantiomer, as a racemate or as a non-equimolar or equimolar mixture of the diastereomers and/or enantiomers.

The invention also provides a method for the treatment, in particular in one of the abovementioned indications, of a non-human mammal or a human requiring treatment of pain, in particular chronic pain, by administration of a therapeutically active dose of a substituted sulfonamide compound according to the invention, or of a pharmaceutical composition according to the invention.

The invention also provides a process for the preparation of the substituted sulfonamide compounds according to the invention as described in the following description, examples and claims.

In one aspect of the present invention, the substituted sulfonamide compounds according to the invention are prepared by the process described in the following (Method I)

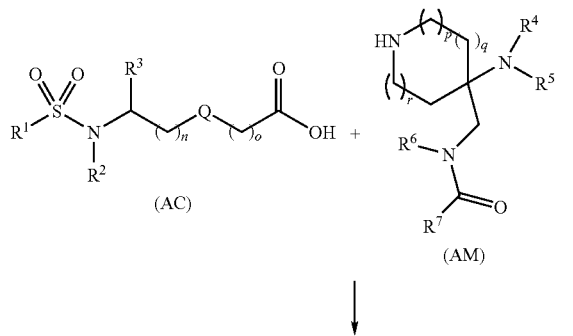

(AC)

(AM)

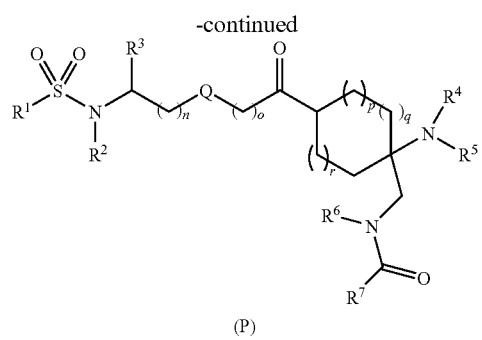

(P)

wherein the free amines (AM) and the carboxylic acids (AC) are reacted in an amide formation in the presence at least of an dehydrating agent and an organic base in an organic solvent to give the compounds (P) according to the invention.

Dehydrating agents which may be used include, for example, sodium sulfate or magnesium sulfate, phosphorus oxide or reagents such as, for example, CDI, DCC (optionally polymer-bonded), TBTU, EDCI, PyBOP or PFPTFA, also in the presence of HOAt or HOBt. Organic bases which can be used are, for example, triethylamine, DIPEA or pyridine, and organic solvents which can be used are THF, methylene chloride, diethyl ether, dioxane, DMF or acetonitrile. The temperature in the amide formation step (1) is preferably between 0 and 50° C.

In a further aspect of the present invention, the substituted sulfonamide compounds according to the invention are prepared by the process described in the following (Method II)

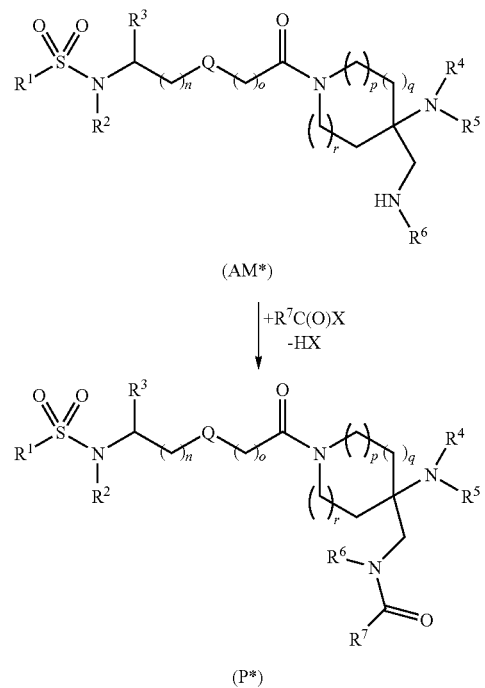

(AM*)

+R⁷C(O)X
-HX (P*)

wherein amines (AM) are acylated with compounds of the type R⁷C(O)X to give the compounds (P*) according to the invention, wherein X represents a halide or a hydroxyl group.

In this context, the acylation reaction can be carried out, in particular, by reaction with carboxylic acids or carboxylic acid chlorides using dehydrating agents, such as, for example, sodium sulfate or magnesium sulfate, phosphorus oxide, or by addition of bases, such as, for example, sodium methanolate, triethylamine, diisopropylethylamine or N-methylmorpholine, and optionally coupling reagents, such as, for example, EDCI, HOBt, DCC (optionally polymer-bonded), CDI, HBTU, DMAP, PyBOP or pentafluorophenyl diphenyl phosphinate, in the presence of HOAt or HOBt in solvents, such as, for example, methanol, DMF, acetonitrile, dioxane, THF, diethyl ether or methylene chloride. The reaction time can vary between 1 h and 3 d, and the temperature is preferably between 0° C. and 50° C.

General Synthesis Process for the Preparation of Acyclic Acid Units methylate, or metal hydrides, such as potassium hydride, lithium hydride, sodium hydride, conventional organic bases are diisopropylethylamine, triethylamine, in an organic solvent, such as methylene chloride, THF or diethyl ether, at 0° C. to the reflux temperature, to give the products of structure C.

In Method II, the racemic (R and S configuration) or enantiomerically polyurethane (R or S configuration) amino alcohols E are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, dimethy- Method I

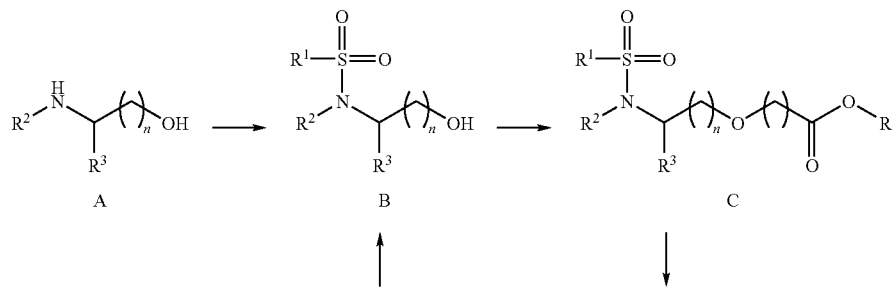

Method II

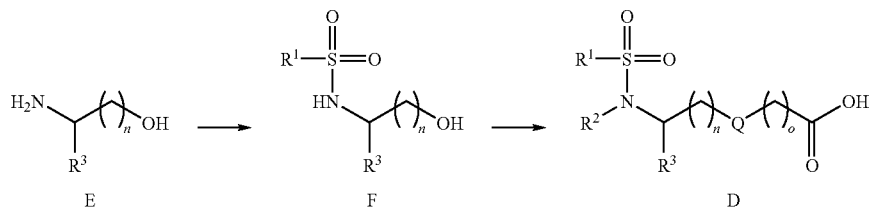

In Method I, the racemic (R and S configuration) or enantiomerically pure (R or S configuration) amino alcohols A are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium carbonate, sodium bicarbonate, diisopropylethylamine, triethylamine, pyridine, dimethylaminopyridine, diethylamine or DBU, preferably in an organic solvent, for example acetone, acetonitrile, methylene chloride or tetrahydrofuran, and at a temperature of from 0° C. to the reflux temperature, to give the sulfonylated amino alcohols B.

The sulfonylated amino alcohols B are reacted in an alkylation reaction with halogenated ester derivatives, using tetrabutylammonium chloride or bromide or tetrabutylammonium hydrogen sulfate, in a phase transfer reaction using an organic solvent, such as THF, toluene, benzene or xylene, and an inorganic base, such as potassium hydroxide, sodium hydroxide, sodium carbonate, sodium bicarbonate, potassium carbonate, or in the presence of an organic or inorganic base, conventional inorganic bases are metal alcoholates, such as sodium methanolate, sodium ethanolate, potassium tert-butylate, lithium bases or sodium bases, such as lithium diisopropylamide, butyllithium, tert-butyllithium, sodium laminopyridine, diethylamine or DBU, preferably in an organic solvent, for example acetone, acetonitrile, methylene chloride or tetrahydrofuran, and at a temperature of from 0° C. to the reflux temperature, to give the sulfonylated amino alcohols F.

The sulfonylated amino alcohols F are then reacted in an alkylation reaction with alkyl halides (RX, X=I, Br, Cl), mesylates or alternative alkylating reagents, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures, at a temperature of from 0° C. to the reflux temperature, to give the sulfonylated amino alcohols B.

In Methods I-II, the ester derivatives C are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, methylene chloride, THF, diethyl ether or these solvents as mixtures, at 0° C. to room temperature, to give the acid stages of the general formula D.

General Synthesis Method for the Preparation of Cyclic Acid Units
Method I
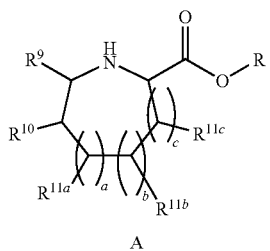
A
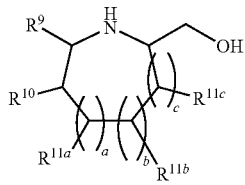
B
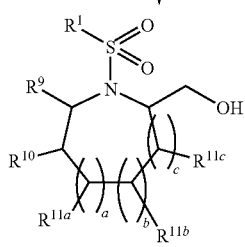
C
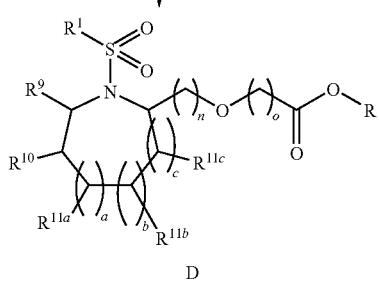
D
Method II
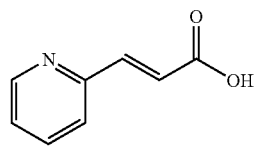
E
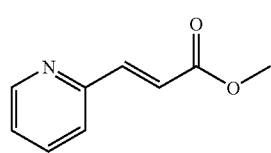
F
Method III
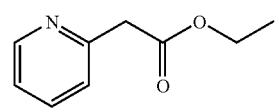
G
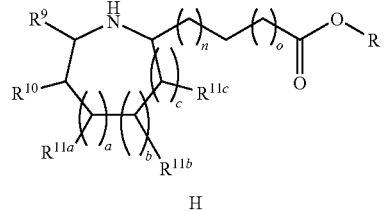
H
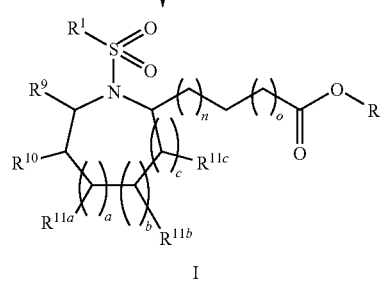
I
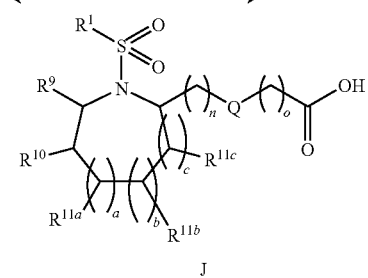
J In Method I, the racemic (R and S configuration) or enantiomerically pure (R or S configuration) amino acid esters A are converted by a reduction into an amino alcohol B using metal hydrides as reducing agents, such as, for example, $LiAlH_4$, $BH_3{\times}DMS$ or $NaBH_4$, in an organic solvent, such as THF or diethyl ether, at temperatures of from 0° C. to the reflux temperature. The amino alcohols B are reacted further in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, dimethylaminopyridine, diethylamine or DBU, preferably in an organic solvent, for example acetone, acetonitrile, methylene chloride or tetrahydrofuran, and at a temperature of from 0° C. to the reflux temperature, to give the sulfonylated amino alcohols C.

The sulfonylated amino alcohols C are reacted in an alkylation reaction with halogenated ester derivatives, using tetrabutylammonium chloride or bromide or tetrabutylammonium hydrogen sulfate, in a phase transfer reaction using an organic solvent, such as THF, toluene, benzene or xylene, and an inorganic base, such as potassium hydroxide, sodium hydroxide, sodium carbonate, sodium bicarbonate, potassium carbonate, or in the presence of an organic or inorganic base, conventional inorganic bases are metal alcoholates, such as sodium methanolate, sodium ethanolate, potassium tert-butylate, lithium bases or sodium bases, such as lithium diisopropylamide, butyllithium, tert-butyllithium, sodium methylate, or metal hydrides, such as potassium hydride, lithium hydride, sodium hydride, conventional organic bases are diisopropylethylamine, triethylamine, in an organic solvent, such as methylene chloride, THF or diethyl ether, at 0° C. to the reflux temperature, to give the products of the general structure D.

In Method II, 3-(pyridin-2-yl)acrylic acid E is esterified using dehydrating reagents, for example inorganic acids, such as $H_2SO_4$ or phosphorus oxides, or organic reagents, such as thionyl chloride, in organic solvents, such as THF, diethyl ether, methanol, ethanol or methylene chloride, to give stage F, at temperatures of from room temperature to the reflux temperature.

In Methods II and III, the ester stages F and G are hydrogenated in a hydrogenation under conditions known to the person skilled in the art in organic solvents, such as THF, chloroform, and in the presence of catalysts, such as platinum oxides, with hydrogen under normal pressure or increased pressure to give the intermediates H.

In Methods II-III, stage H is reacted further in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran, at 0° C. to the reflux temperature, to give the sulfonylated amino esters 1.

In Methods I-III, the ester derivatives D and I are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, methylene chloride, THF, diethyl ether or these solvents as mixtures, at 0° C. to room temperature, to give the acid stages of the general formula J.

General Synthesis of the Amine Units

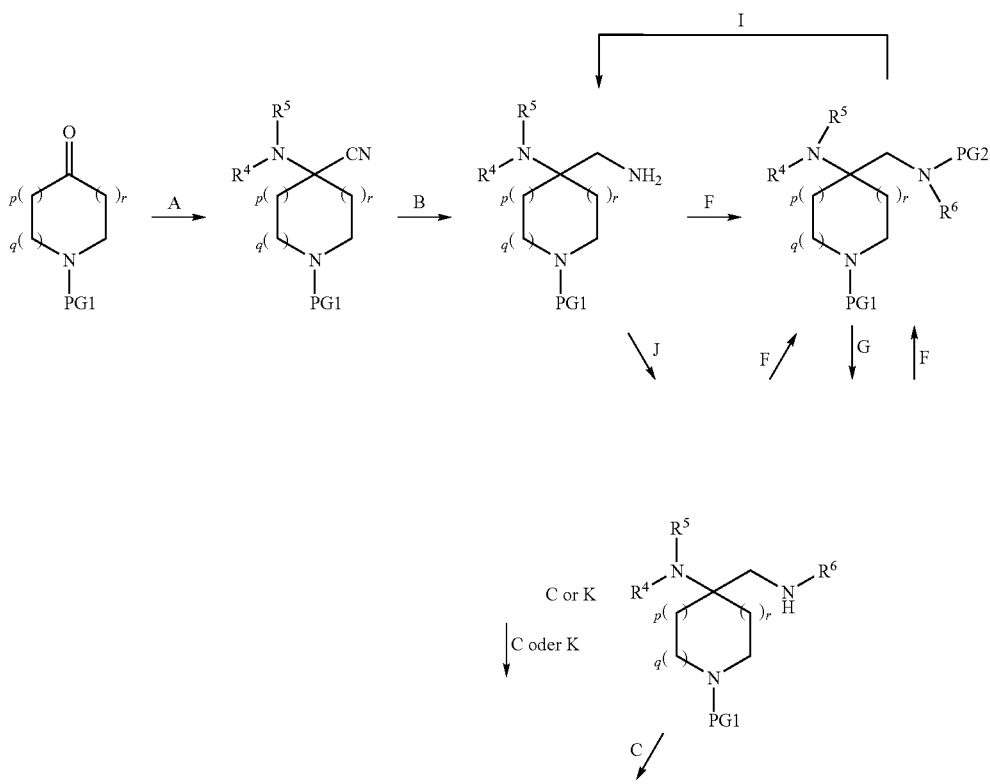

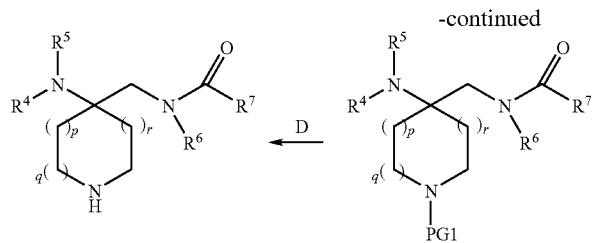 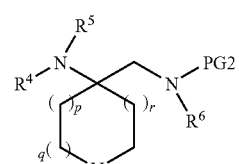

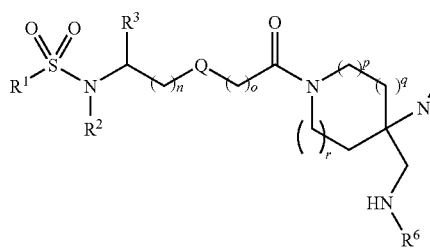 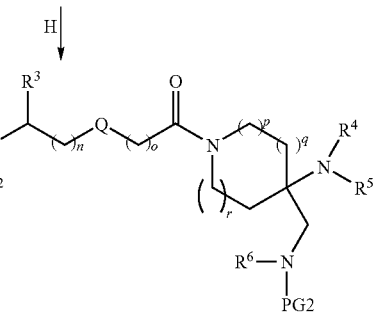

A: The protected piperidone employed can be converted into the nitrile by addition of an amine and a source of cyanide. The reaction can be carried out in one or two stages, as is known to the person skilled in the art. In the two-stage variant, a nitrile alcohol is first formed and isolated. The nitrile alcohol can be formed by reaction of the protected piperidone with HCN, KCN or NaCN. Typical solvents are water, methanol, ethanol, THF, piperidine, diethyl ether or a mixture of these solvents. If NaCN and KCN are used, the cyanide required can typically be liberated by addition of, for example, sodium hydrogen sulfite, sulfuric acid, acetic acid or hydrochloric acid.

Trimethylsilyl cyanide, for example, is likewise suitable as a source of nitrile. In this case the cyanide can be liberated, for example, by boron trifluoride etherate, $InF_3$ or HCl. Typical solvents here are water or toluene.

(Cyano-C)diethylaluminium, for example, is suitable as a further source of cyanide. THF, toluene or a mixture of the two solvents can be used as the solvent.

The reaction temperature can be between −78° C. and +25° C. for all the variants.

Alcohols, such as methanol or ethanol, are particularly suitable as the solvent for the reaction of the nitrile alcohol with the amine. The reaction temperature can be between 0° C. and +25° C.

In the one-stage variant, the nitrile alcohol primarily formed is formed in situ and reacted with the amine.

B: The reduction of the nitrile group can be carried out with the aid of reducing agents or by catalytic hydrogenation.

Suitable reducing agents include, for example, lithium aluminium hydride, aluminium hydride or sodium, in solvents, such as, for example, THF, diethyl ether, dioxane or ethanol. The catalytic hydrogenation can be carried out by means of catalysts, such as, for example, platinum, platinum(IV) oxide or Raney nickel, in solvents, such as ethanol, methanol, optionally with the addition of ammonia or aqueous HCl.

C: The subsequent acylation reaction of the amine can be carried out by reaction with carboxylic acids or carboxylic acid chlorides using dehydrating agents, such as, for example, sodium sulfate or magnesium sulfate, phosphorus oxide, or by addition of bases, such as, for example, sodium methanolate, triethylamine, diisopropylethylamine or N-methylmorpholine, and optionally coupling reagents, such as, for example, EDCI, HOBt, DCC (optionally polymer-bonded), CDI, HBTU, DMAP, PyBOP or pentafluorophenyl diphenyl phosphinate, in the presence of HOAt or HOBt in solvents, such as, for example, methanol, DMF, acetonitrile, dioxane, THF, diethyl ether or MC. The reaction time can vary between 1 hour and 3 days.

D: The method for removing the protective groups depends on the nature of the protective group used. For example, carbamates, such as, for example, the Boc, Fmoc or Cbz(Z) protective group, or also benzylic protective groups are suitable.

The BOC protective group can be removed, for example, by reaction with HCl in organic solvents, such as dioxane, methanol, ethanol, acetonitrile or ethyl acetate, or by reaction with TFA or methanesulfonic acid in methylene chloride or THF at a temperature of from 0° C. to 110° C. over a reaction time of 0.5-20 h.

The Cbz protective group can be removed, for example, under acidic conditions. This acidic splitting off can be carried out, for example, by reaction with an HBr/glacial acetic acid mixture, a mixture of TFA in dioxane/water or HCl in methanol or ethanol. However, reagents such as, for example, $Me_3Sil$, in solvents, such as, for example, MC, chloroform or acetonitrile, $BF_3$ etherate with the addition of ethanethiol or $Me_2S$, in solvents, such as, for example, MC, a mixture of aluminium chloride/anisole in a mixture of MC and nitromethane, or triethylsilane/$PdCl_2$ in methanol, with the addition of triethylamine, are also suitable. A further method is the hydrogenolytic removal of the protective group under increased pressure or normal pressure with the aid of catalysts, such as, for example, Pd on charcoal, $Pd(OH)_2$, $PdCl_2$, Raney nickel or $PtO_2$, in solvents, such as, for example, methanol, ethanol, 2-propanol, THF, acetic acid, ethyl acetate, chloroform, optionally with the addition of HCl, formic acid or TFA.

The Fmoc protective group is as a rule removed under basic conditions in solvents, such as, for example, acetonitrile, DMF, THF, diethyl ether, methanol, ethanol, 1-octanethiol, MC or chloroform. Suitable bases are, for example, diethylamine, piperidine, 4-aminomethylpiperidine, pyrrolidine, DBU, NaOH or LiOH. However, reagents such as, for example, Ag$_2$O/MeI can also be used.

A benzylic protective group can be removed, for example, by catalytic hydrogenation. Suitable catalysts are, for example, Pd on charcoal, PtO$_2$ or Pd(OH)$_2$. The reaction can be carried out in solvents, such as, for example, ethanol, methanol, 2-propanol, acetic acid, THF or DMF, with the addition of acids, such as, for example, ammonium formate, maleic acid or formic acid, or in mixtures of the solvents.

F: The amine function, for instance the primary amine function, is protected with the aid of a protective group. Protective groups which differ from the protective group on the piperidine nitrogen are suitable in this step. For example, carbamates, such as, for example, the Boc, Fmoc or Cbz(Z) protective group, or a benzylic protective group are suitable.

The introduction of the BOC protective group using di-tert-butyl dicarbonate can be carried out in solvents, such as, for example, dioxane, MC, THF, DMF, water, benzene, toluene, methanol, acetonitrile or mixtures of these solvents, optionally with the addition of sodium hydroxide, triethylamine, diisopropylethylamine, sodium bicarbonate, sodium carbonate or DMAP, at temperatures of between 0° C. and 100° C.

The Fmoc protective group is introduced by reaction of 9H-fluoren-9-ylmethyl chloroformate in solvents, such as, for example, MC, DCE, diethyl ether, THF, dioxane, acetone, acetonitrile, DMF or water, optionally with the addition of a base, such as, for example, diisopropylethylamine, triethylamine, pyridine, N-methylmorpholine, sodium carbonate or sodium bicarbonate, and optionally under irradiation with microwaves.

The Cbz protective group can be introduced by reaction of chloroformic acid benzyl ester in solvents, such as, for example, diethyl ether, THF, DMF, benzene, toluene, dioxane, water, acetone, ethyl acetate, MC or chloroform, optionally with the addition of a base, such as, for example, sodium carbonate, sodium bicarbonate, potassium carbonate, sodium hydroxide or triethylamine, optionally with the addition of a coupling reagent, such as, for example, HOBt.

Benzylic protective groups can be introduced by alkylation using chloro- or bromobenzyl compounds or by reductive amination with benzaldehydes. The alkylation can be carried out in solvents, such as, for example, ethanol, methanol, water, acetonitrile, MC, THF, DMSO, water or mixtures of these solvents. If appropriate, a base, such as, for example, diethylamine, sodium bicarbonate, sodium carbonate, potassium carbonate or caesium carbonate, and if appropriate an auxiliary reagent, such as, for example, potassium iodide or sodium iodide, must be added. The reductive amination is carried out in solvents, such as, for example, methanol, ethanol, DCE or MC. Suitable reducing agents are, for example, sodium cyanoborohydride or sodium triacetoxyborohydride, optionally with the addition of acetic acid.

Optionally, a trifluoroacetyl protecting group (CF$_3$CO) can be introduced by reaction of the amine with trifluoroacetic anhydride in the presence of a suitable base, such as for example triethylamine or Hünig base, in a suitable solvent such as dichloromethane, THF, chloroform or mixtures thereof.

G: The protective group on the piperidine nitrogen is removed. The method for removing the protective groups depends on the nature of the protective group used. For example, carbamates, such as, for example, the Boc, Fmoc or Cbz(Z) protective group, or also benzylic protective groups are suitable.

The BOC protective group can be removed, for example, by reaction with HCl in organic solvents, such as dioxane, methanol, ethanol, acetonitrile or ethyl acetate, or by reaction with TFA or methanesulfonic acid in methylene chloride or THF at a temperature of from 0° C. to 110° C. over a reaction time of 0.5-20 h.

The Cbz protective group can be removed, for example, under acidic conditions. This acidic splitting off can be carried out, for example, by reaction with an HBr/glacial acetic acid mixture, a mixture of TFA in dioxane/water or HCl in methanol or ethanol. However, reagents such as, for example, Me$_3$SiI, in solvents, such as, for example, MC, chloroform or acetonitrile, BF$_3$ etherate with the addition of ethanethiol or Me$_2$S, in solvents, such as, for example, MC, a mixture of aluminium chloride/anisole in a mixture of MC and nitromethane, or triethylsilane/PdCl$_2$ in methanol, with the addition of triethylamine, are also suitable. A further method is the hydrogenolytic removal of the protective group under increased pressure or normal pressure with the aid of catalysts, such as, for example, Pd on charcoal, Pd(OH)$_2$, PdCl$_2$, Raney nickel or PtO$_2$, in solvents, such as, for example, methanol, ethanol, 2-propanol, THF, acetic acid, ethyl acetate, chloroform, optionally with the addition of HCl, formic acid or TFA.

The Fmoc protective group is as a rule removed under basic conditions in solvents, such as, for example, acetonitrile, DMF, THF, diethyl ether, methanol, ethanol, 1-octanethiol, MC or chloroform. Suitable bases are, for example, diethylamine, piperidine, 4-aminomethylpiperidine, pyrrolidine, DBU, NaOH or LiOH. However, reagents such as, for example, Ag$_2$O/MeI can also be used.

A benzylic protective group can be removed, for example, by catalytic hydrogenation. Suitable catalysts include, for example, Pd on charcoal, PtO$_2$ or Pd(OH)$_2$. The reaction can be carried out in solvents, such as, for example, ethanol, methanol, 2-propanol, acetic acid, THF or DMF, with the addition of acids, such as, for example, ammonium formate, maleic acid or formic acid, or in mixtures of the solvents.

H: The subsequent acylation reaction of the amine can be carried out by reaction with carboxylic acids or carboxylic acid chlorides using dehydrating agents, such as, for example, sodium sulfate or magnesium sulfate, phosphorus oxide, or by addition of bases, such as, for example, sodium methanolate, triethylamine, diisopropylethylamine or N-methylmorpholine, and optionally coupling reagents, such as, for example, EDCI, HOBt, DCC (optionally polymer-bonded), CDI, HBTU, DMAP, PyBOP or pentafluorophenyl diphenyl phosphinate, in the presence of HOAt or HOBt in solvents, such as, for example, methanol, DMF, acetonitrile, dioxane, THF, diethyl ether or MC. The reaction time can vary between 1 hour and 3 days.

I: The second protective group is then removed. The method for removing the protective groups depends on the nature of the protective group used. For example, carbamates, such as, for example, the Boc, Fmoc or Cbz(Z) protective group, or also benzylic protective groups are suitable.

The BOC protective group can be removed, for example, by reaction with HCl in organic solvents, such as dioxane, methanol, ethanol, acetonitrile or ethyl acetate, or by reaction with TFA or methanesulfonic acid in methylene chloride or THF at a temperature of from 0° C. to 110° C. over a reaction time of 0.5-20 h.

The Cbz protective group can be removed, for example, under acidic conditions. This acidic splitting off can be carried out, for example, by reaction with an HBr/glacial acetic acid mixture, a mixture of TFA in dioxane/water or HCl in methanol or ethanol. However, reagents such as, for example, $Me_3SiI$, in solvents, such as, for example, MC, chloroform or acetonitrile, $BF_3$ etherate with the addition of ethanethiol or $Me_2S$, in solvents, such as, for example, MC, a mixture of aluminium chloride/anisole in a mixture of MC and nitromethane, or triethylsilane/$PdCl_2$ in methanol, with the addition of triethylamine, are also suitable. A further method is the hydrogenolytic removal of the protective group under increased pressure or normal pressure with the aid of catalysts, such as, for example, Pd on charcoal, $Pd(OH)_2$, $PdCl_2$, Raney nickel or $PtO_2$, in solvents, such as, for example, methanol, ethanol, 2-propanol, THF, acetic acid, ethyl acetate, chloroform, optionally with the addition of HCl, formic acid or TFA.

The Fmoc protective group is as a rule removed under basic conditions in solvents, such as, for example, acetonitrile, DMF, THF, diethyl ether, methanol, ethanol, 1-octanethiol, MC or chloroform. Suitable bases are, for example, diethylamine, piperidine, 4-aminomethylpiperidine, pyrrolidine, DBU, NaOH or LiOH. However, reagents such as, for example, $Ag_2O$/MeI can also be used.

A benzylic protective group can be removed, for example, by catalytic hydrogenation. Suitable catalysts are, for example, Pd on charcoal, $PtO_2$ or $Pd(OH)_2$. The reaction can be carried out in solvents, such as, for example, ethanol, methanol, 2-propanol, acetic acid, THF or DMF, with the addition of acids, such as, for example, ammonium formate, maleic acid or formic acid, or in mixtures of the solvents.

If a trifluoroacetyl protecting group ($CF_3CO$) is used, it can be removed in the presence of a suitable base, such as for example potassium carbonate or lithium hydroxide, in a suitable solvent, such as methanol, ethanol, water or mixtures thereof.

J: The reductive amination is carried out by reaction of aldehydes with amines and subsequent reduction with reducing agents, such as, for example, $NaBH(OAc)_3$, $NaBH_4$, $LiBH_3CN$, $NaBH_3CN$, borane-pyridine complex or α-picoline-borane complex, in solvents, such as, for example, ethanol, methanol, MC, DCE, THF, DMF, benzene, toluene or mixtures of these solvents, optionally with the addition of acids, such as, for example, HCl or acetic acid. Alternatively, the aldehyde can be reacted with a corresponding amine to give the imine, optionally with the addition of dehydrating agents, and then converted into the amine by catalytic hydrogenation. Suitable catalysts include, for example, $Pt_2O$, Pd on charcoal or Raney nickel, in solvents, such as, for example, ethanol or methanol.

Protecting groups in general can be selected from a large variety of possibilities and can be introduced and cleaved according to the literature:
1. Philip J. Kocienski, Protecting Groups, 3rd Edition, Georg Thieme Verlag, 2005 (ISBN 3-13-135603-0), in particular pages 498-501, 505-524, 528-534, 570-585, 606-618, 625;
2. Peter G. M. Wuts, Theodora W. Greene, Greene's Protective Groups in Organic Synthesis, 4th Edition, Wiley-Interscience, 2007 (ISBN-13: 978-0-471-69754-1); in particular pages 696-932.

K: The cyclization reaction of the amine is effected under conditions known to those skilled in the art by reaction with aromatic or heteroaromatic 2-(halomethyl) acids or esters or with 2-(2=haloethyl) acids or esters, optionally with the addition of organic bases, such as diisopropylethylamine, triethylamine, pyridine, dimethylaminopyridine, diethylamine or DBU, or an inorganic base, for example potassium carbonate, sodium carbonate, sodium bicarbonate, preferably in an organic solvent, for example toluene, benzene, xylene, acetone, acetonitrile, methylene chloride or tetrahydrofuran, and at a temperature of from 0° C. to the reflux temperature.

EXAMPLES

The invention will be explained in further detail hereinafter with reference to the following illustrative examples, without limiting the overall scope of the invention. The chemicals and solvents employed were obtained commercially from conventional suppliers (e.g. Acros, Avocado, Aldrich, Bachem, Fluka, Lancaster, Maybridge, Merck, Sigma, TCI etc.) or synthesized by methods known to persons skilled in the art. Commercially obtainable materials, for example $Al_2O_3$ or silica gel [for example from E. Merck, Darmstadt, Germany] were employed as the stationary phase for the column chromatography. Thin layer chromatography investigations were carried out with commercially available HPTLC precoated plates (for example silica gel 60 F 254 from E. Merck, Darmstadt). Mixing ratios of solvents, mobile phases or for chromatography investigations are, unless indicated otherwise, always stated in volume/volume. Analytical studies were carried out by mass spectroscopy (ESI-MS).

LIST OF ABBREVIATIONS eq. Equivalent(s)
Bz Benzyl
Boc tert-Butyl carbamate
$Boc_2O$ Di-tert-butyl dicarbonate
CDI 1,1'-Carbonyldiimidazole
MC Methylene chloride
DBU 1,8-Diazabicyclo[5.4.0]undec-7-ene (1, 5-5)
DCC N,N'-Dicyclohexylcarbodiimide
DIPEA Diisopropylethylamine
DMAP N,N-Dimethylaminopyridine
DMF Dimethylformamide
DMSO Dimethylsulfoxide
EDCI N-(3-Dimethylaminopropyl)-N'-ethyl-carbodiimide
sat. Saturated
h Hour(s)
HBTU O-(Benzotriazol-1-yl)-N,N,N',N'-tetramethyluronium hexafluorphosphate
HOAt 1-Hydroxy-7-azabenzotriazole
HOBt 1-Hydroxy-1H-benzotriazole
LAH Lithium aluminium hydride
M Molar
min Minute(s)
PFPTFA Pentafluorophenyl trifluoroacetate
PG Protective group
PyBOP (Benzotriazol-1-yloxy)-tri-pyrrolidinophosphonium hexafluorophosphate
RT Room temperature.
TFA Trifluoroacetic acid
THF Tetrahydrofuran
Acid Units The following acid units were synthesized and employed for synthesis of the compounds according to the invention:

| Acid unit | Structure | Name |
|---|---|---|
| AC1 | 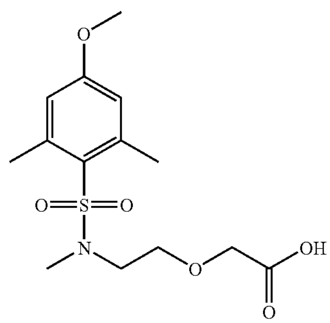 [SMILES: COc1cc(C)c(S(=O)(=O)N(C)CCOCC(=O)O)c(C)c1] | 2-(2-(4-Methoxy-N,2,6-trimethylphenylsulfonamido)ethoxy)-acetic acid |
| AC2 | 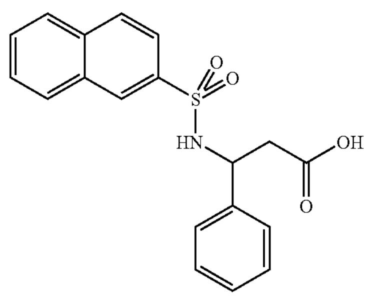 [SMILES: O=C(O)CC(NS(=O)(=O)c1ccc2ccccc2c1)c1ccccc1] | 3-(Naphthalene-2-sulfonamido)-3-phenylpropionic acid |
| AC3 | 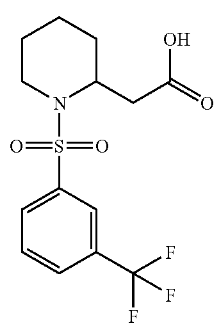 [SMILES: O=C(O)CC1CCCCN1S(=O)(=O)c1cccc(C(F)(F)F)c1] | 2-(1-(3-(Trifluoromethyl)phenylsulfonyl)piperidin-2-yl)acetic acid |
| AC4 | 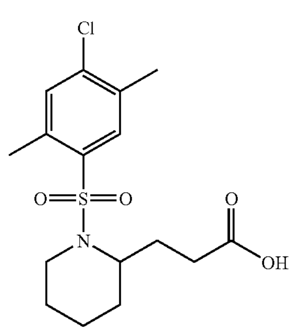 [SMILES: Cc1cc(S(=O)(=O)N2CCCCC2CCC(=O)O)c(C)cc1Cl] | 3-(1-(4-Chloro-2,5-dimethylphenylsulfonyl)piperidin-2-yl)propionic acid |

-continued

| Acid unit | Structure | Name |
|---|---|---|
| AC5 | 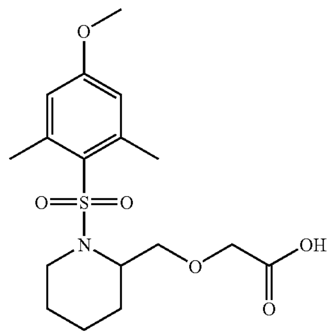 [SMILES: COc1cc(C)c(S(=O)(=O)N2CCCCC2COCC(=O)O)c(C)c1] | 2-((1-(4-Methoxy-2,6-dimethylphenylsulfonyl)piperidin-2-yl)methoxy)acetic acid |
| AC6 | 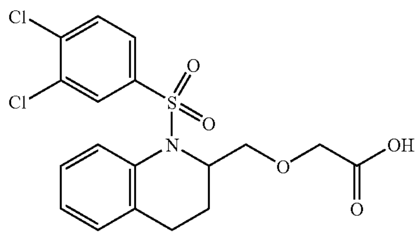 [SMILES: O=C(O)COCC1CCc2ccccc2N1S(=O)(=O)c1ccc(Cl)c(Cl)c1] | 2-((1-(3,4-Dichlorophenylsulfonyl)-1,2,3,4-tetrahydroquinolin-2-yl)methoxy)acetic acid |
| AC7 | 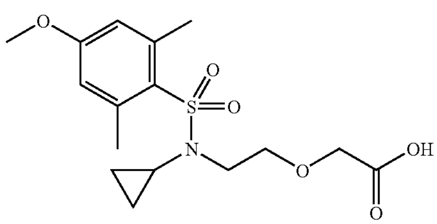 [SMILES: COc1cc(C)c(S(=O)(=O)N(CCOCC(=O)O)C2CC2)c(C)c1] | 2-(2-(N-Cyclopropyl-4-methoxy-2,6-dimethylphenylsulfonamido)ethoxy)acetic acid |
| AC8 | 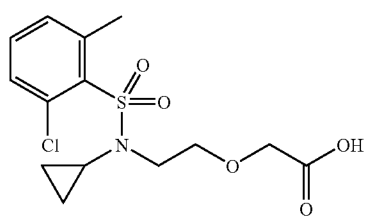 [SMILES: Cc1cccc(Cl)c1S(=O)(=O)N(CCOCC(=O)O)C1CC1] | 2-(2-(2-Chloro-N-cyclopropyl-6-methylphenylsulfonamido)ethoxy)acetic acid |
| AC9 | 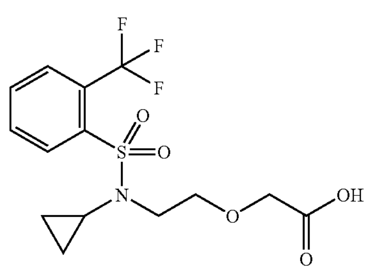 [SMILES: O=C(O)COCCN(C1CC1)S(=O)(=O)c1ccccc1C(F)(F)F] | 2-(2-(N-Cyclopropyl-2-(trifluoromethyl)phenylsulfonamido)ethoxy)acetic acid |
| AC10 | 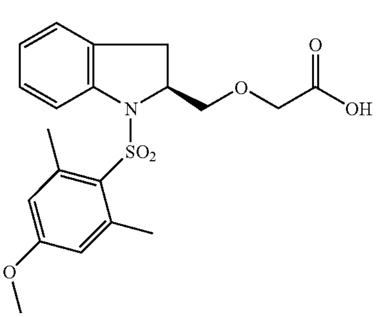 [SMILES: COc1cc(C)c(S(=O)(=O)N2c3ccccc3C[C@H]2COCC(=O)O)c(C)c1] | (S)-2-((1-(4-Methoxy-2,6-dimethylphenylsulfonyl)indolin-2-yl)methoxy)acetic acid |

-continued

| Acid unit | Structure | Name |
|---|---|---|
| AC-11 | 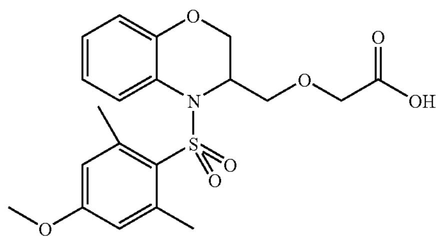 [SMILES: COc1cc(C)c(S(=O)(=O)N2c3ccccc3OCC2COCC(=O)O)c(C)c1] | 2-((4-(4-Methoxy-2,6-dimethylphenylsulfonyl)-3,4-dihydro-2H-benzo[b][1,4]oxazin-3-yl)methoxy)acetic acid |
| AC-12 | 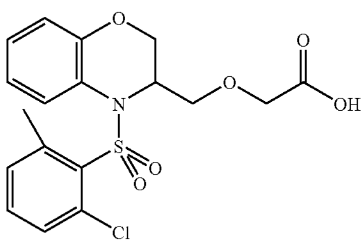 [SMILES: Cc1cccc(Cl)c1S(=O)(=O)N1c2ccccc2OCC1COCC(=O)O] | 2-((4-(2-Chloro-6-methylphenylsulfonyl)-3,4-dihydro-2H-benzo[b][1,4]oxazin-3-yl)methoxy)acetic acid) |
| AC-13 | 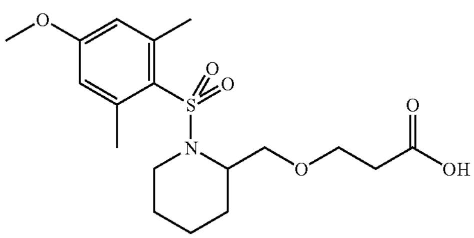 [SMILES: COc1cc(C)c(S(=O)(=O)N2CCCCC2COCCC(=O)O)c(C)c1] | 3-((1-(4-Methoxy-2,6-dimethylphenylsulfonyl)piperidin-2-yl)methoxy)propanoic acid |
| AC-14 | 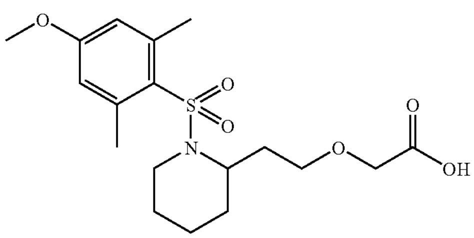 [SMILES: COc1cc(C)c(S(=O)(=O)N2CCCCC2CCOCC(=O)O)c(C)c1] | 2-(2-(1-(4-Methoxy-2,6-dimethylphenylsulfonyl)piperidin-2-yl)ethoxy)acetic acid |
| AC-15 | 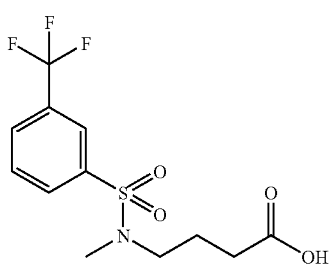 [SMILES: CN(CCCC(=O)O)S(=O)(=O)c1cccc(C(F)(F)F)c1] | 4-(N-Methyl-3-(trifluoromethyl)phenylsulfonamido)butanoic acid |
| AC-16 | 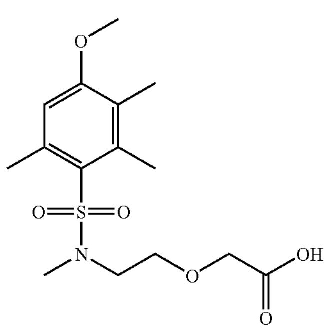 [SMILES: COc1cc(C)c(S(=O)(=O)N(C)CCOCC(=O)O)c(C)c1C] | 2-(2-(4-Methoxy-N,2,3,6-tetramethylphenylsulfonamide)-ethoxy)-acetic acid |

(In the following synthesis descriptions, the acid units "AC", where appropriate, are also described as $R^{20}$—COOH. The particular meaning of the radical $R^{20}$ thus results unambiguously by reference to the above table or in the general meaning as a group having the following structure

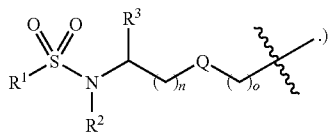

Preparation of 2-(2-(4-methoxy-N,2,6-trimethylphenylsulfonamido)-ethoxy)acetic acid AC1

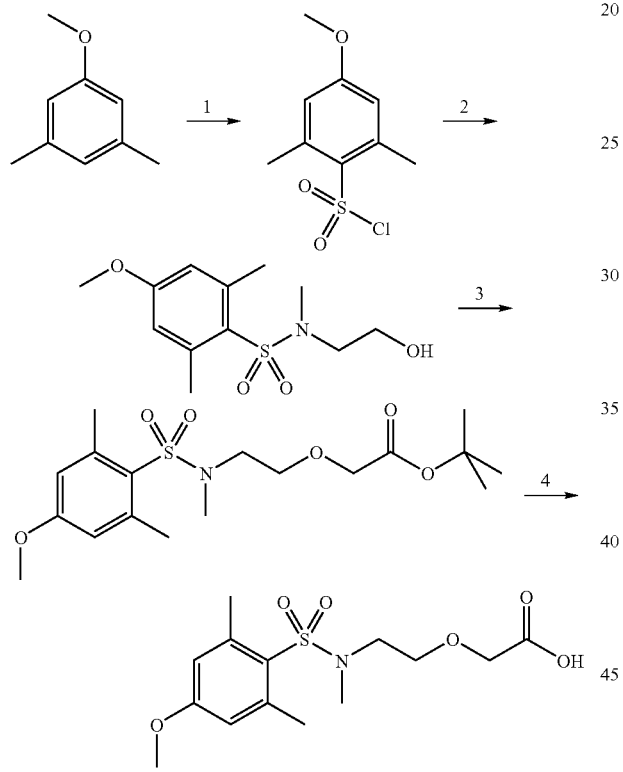

Stage 1: A solution of 3,5-dimethylanisole (102.5 g, 753 mmol) in MC (1 l) was cooled to 0° C. A solution of chlorosulfonic acid (251 ml, 3.763 mmol) in MC (250 ml) was added dropwise to this solution. After a reaction time of 10 min, the reaction solution was introduced into an ice bath (1 l), the phases were separated and extraction was carried out once more with MC (250 ml). The combined organic phases were washed with water (1 l) and sat. NaCl solution (1 l), dried over $Na_2SO_4$ and concentrated. The product was purified by column chromatography over silica gel (heptane/MC 5:1). Yield: 63.5 g, 36%.

Stage 2. Triethylamine (80 mmol) was added to a solution of the amino alcohol (35 mmol) in MC (200 ml) and the mixture was cooled to 0° C. using an ice bath. The sulfonyl chloride (32 mmol) was then added and the mixture was stirred at RT for 3 h. After addition of 0.5 M HCl (100 ml), the organic phase was separated, washed with water, dried over $Na_2SO_4$ and filtered and the solvent was removed in vacuo. The crude product was used in the next stage without further purification.

Stage 3. n-$Bu_4NCl$ (10 mmol) was added to a solution of the product from stage 2. (30 mmol) in toluene (125 ml). The mixture was cooled to 0° C., and first aqueous 35% strength NaOH (150 ml) and then bromoacetic acid tert-butyl ester (45 mmol) in toluene (25 ml) were added dropwise. The reaction mixture was stirred for 3 h and then washed neutral with water and dried with $Na_2SO_4$ and the organic solvent was removed in vacuo. The crude product was used in the next stage without further purification.

Stage 4. The product from stage 3. (20 mmol) was dissolved in 4 N hydrochloric acid in dioxane (80 ml) and the solution was stirred at RT overnight. The solvent was largely distilled off and the crude product was purified by recrystallization.

Preparation of 3-(naphthalene-2-sulfonamido)-3-phenylpropionic acid AC2

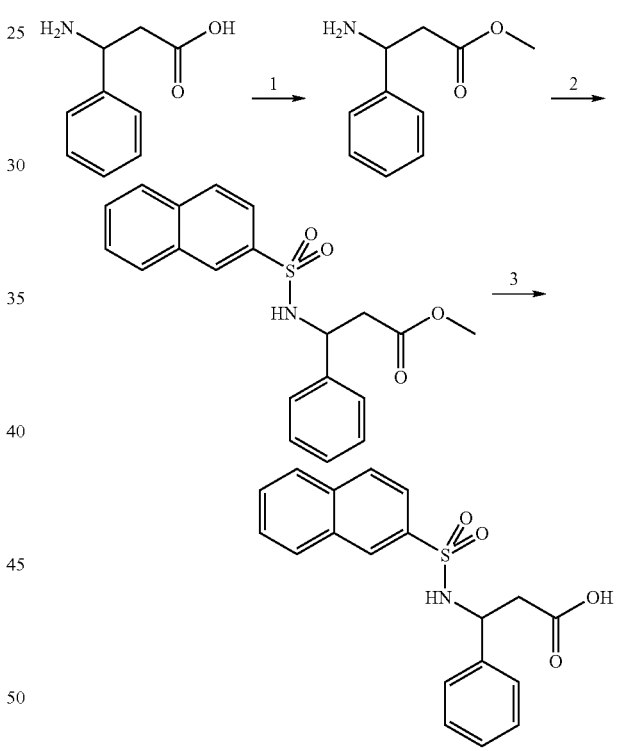

Stage 1. Thionyl chloride (19.1 g, 162 mmol) was added dropwise to a solution, cooled to 0° C., of 3-amino-3-phenylpropionic acid (8.9 g, 54 mmol) in methanol (3 ml/mmol). The reaction mixture was then heated under reflux for 12 h (TLC control). The solvent was removed completely and the residue was dried in vacuo. The crude product was employed in the next stage without further purification.

Stage 2. Triethylamine (9.7 g, 96 mmol) was added to a solution, cooled to 0° C., of methyl 3-amino-phenylpropionate (5.73 g, 32 mmol) in MC. Naphthalene-2-sulfonyl chloride (8.7 g, 38.4 mmol), dissolved in MC (50 ml), was added to this reaction solution. The reaction mixture was stirred at RT for 3 h (TLC control). When the reaction had ended, the reaction mixture was diluted with MC, washed with water and sat. NaCl solution and dried over Na$_2$SO$_4$ and filtered. The solvent was removed in vacuo and the crude product was purified by column chromatography (silica gel, ethyl acetate/hexane, 3:7).

Stage 3. LiOH×H$_2$O (0.25 g, 18 mmol) was added to a solution of the methyl 3-(naphthalene-2-sulfonamido)-3-phenylpropionate (3.3 g, 9 mmol) in a methanol/water mixture (3:1, 90 ml) at a reaction temperature of 0° C. The reaction mixture was stirred at RT for 16 h. The solvent was removed under reduced pressure, the residue was taken up in water and the mixture was washed with MC. The aqueous phase was then cautiously acidified with HCl (1 N) and extracted with ethyl acetate. The organic phase was washed with water and sat. NaCl solution and dried over Na$_2$SO$_4$. After removal of the solvent, the product was obtained in an adequate purity.

Preparation of 2-(1-(3-(trifluoromethyl)phenylsulfonyl)piperidin-2-yl)acetic acid AC3

MC/methanol 98:2), the reaction mixture was diluted with MC (275 ml) and washed successively with KHSO$_4$ solution (0.5 M, 500 ml) and sat. NaCl solution (500 ml). The organic phase was dried over Na$_2$SO$_4$ and concentrated. The crude product was purified by column chromatography over silica gel (MC). Yield: 10.45 g, 76% over 2 stages.

Stage 3. The ethyl 2-(1-(3-(trifluoromethyl)phenylsulfonyl)piperidin-2-yl)acetate (10.45 g, 27.5 mmol) was dissolved in a mixture of methanol (150 ml), dioxane (40 ml) and aqueous NaOH solution (4 M, 41.3 ml, 165.2 mmol, 6 eq.) and the solution was stirred overnight When the reaction had ended (TLC control, MC/methanol 95:5), the solution was concentrated. The crude product was taken up in ethyl acetate (600 ml) and the mixture was . . . with KHSO$_4$ solution (0.5 M, 600 ml). The aqueous phase was extracted once more with ethyl acetate (100 ml) and the combined organic phases were washed with sat. NaCl solution (500 ml), dried over Na$_2$SO$_4$ and concentrated. Yield: 9.4 g, 97%.

Preparation of 3-(1-(4-chloro-2,5-dimethylphenylsulfonyl)piperidin-2-yl)propionic acid AC4

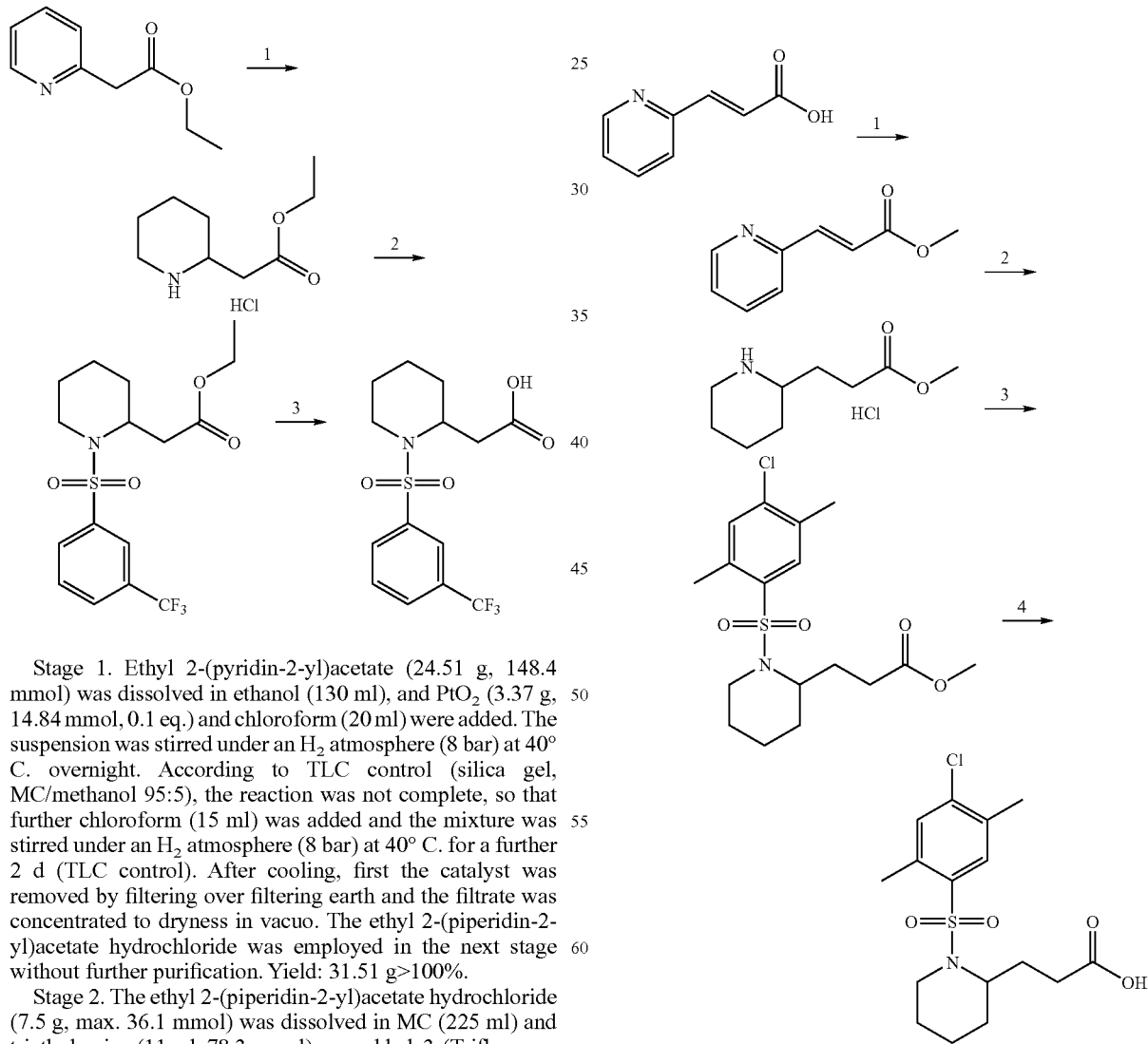

Stage 1. Ethyl 2-(pyridin-2-yl)acetate (24.51 g, 148.4 mmol) was dissolved in ethanol (130 ml), and PtO$_2$ (3.37 g, 14.84 mmol, 0.1 eq.) and chloroform (20 ml) were added. The suspension was stirred under an H$_2$ atmosphere (8 bar) at 40° C. overnight. According to TLC control (silica gel, MC/methanol 95:5), the reaction was not complete, so that further chloroform (15 ml) was added and the mixture was stirred under an H$_2$ atmosphere (8 bar) at 40° C. for a further 2 d (TLC control). After cooling, first the catalyst was removed by filtering over filtering earth and the filtrate was concentrated to dryness in vacuo. The ethyl 2-(piperidin-2-yl)acetate hydrochloride was employed in the next stage without further purification. Yield: 31.51 g>100%.

Stage 2. The ethyl 2-(piperidin-2-yl)acetate hydrochloride (7.5 g, max. 36.1 mmol) was dissolved in MC (225 ml) and triethylamine (11 ml, 78.3 mmol) was added. 3-(Trifluoromethyl)benzene-1-sulfonyl chloride (9.72 g, 39.7 mmol) was then added dropwise and the mixture was stirred at RT overnight. When the reaction had ended (TLC control, Stage 1. H$_2$SO$_4$ (12.8 ml, 240 mmol) was added to a solution of 3-(2-pyridyl)-arylic acid (23.88 g, 160 mmol) in methanol (750 ml). The reaction mixture was heated under reflux overnight and, after cooling to RT, was poured into sat. aqueous NaHCO$_3$ solution (1 ml). The methanol was removed on a rotary evaporator and the aqueous phase was extracted twice with ethyl acetate (400 ml). The organic phase was washed with sat. NaCl solution (500 ml), dried over Na$_2$SO$_4$ and concentrated. The crude product was employed in the next stage without further purification. Yield: 22.19 g, 85%.

Stage 2. Methyl 3-(pyridin-2-yl)acrylate (22.15 g, 136 mmol) was dissolved in THF (300 ml) and chloroform (10.9 ml), and PtO$_2$ (3.08 g, 13.6 mmol, 0.1 eq.) was added under a nitrogen atmosphere. The solution was first flushed with nitrogen for 10 min and then stirred under an H$_2$ atmosphere (8 bar) overnight. After cooling, first the mixture was flushed against with nitrogen, the catalyst was removed by filtering over filtering earth and rinsed with MC and the filtrate was concentrated to dryness in vacuo. The methyl 3-(piperidin-2-yl)propionate hydrochloride was employed in the next stage without further purification. Yield: 27.95 g, 99%.

Stage 3. A solution of triethylamine (14.7 ml, 104.5 mmol), dissolved in MC (150 ml), was added to a solution of methyl 3-(piperidin-2-yl)propionate hydrochloride (8.69 g, 41.8 mmol) and 4-chloro-2,5-dimethylbenzenesulfonyl chloride (10 g, 41.8 mmol) in MC (150 ml). The reaction mixture was stirred at RT overnight and then washed with HCl (1 M, 300 ml). The organic phase was dried over Na$_2$SO$_4$ and concentrated. The crude product was purified by column chromatography over silica gel (heptane/ethyl acetate 6:1 to 3:1). Yield: 12.82 g, 82%.

Stage 4. Aqueous NaOH solution (6 M, 100 ml) was added to a solution of methyl 3-(1-(4-chloro-2,5-dimethylphenylsulfonyl)piperidin-2-yl)propionate (12.82 g, 34.3 mmol) in THF (100 ml). After a reaction time of 1 h, the solvent was removed on a rotary evaporator and the residue was cooled to 0° C. HCl (6 M, 100 ml) was added and the mixture was extracted with ethyl acetate. The organic phase was dried over Na$_2$SO$_4$ and concentrated. Yield: 12.36 g, 100%.

Preparation of 2-((1-(4-methoxy-2,6-dimethylphenylsulfonyl)piperidin-2-yl)methoxy)acetic acid AC5

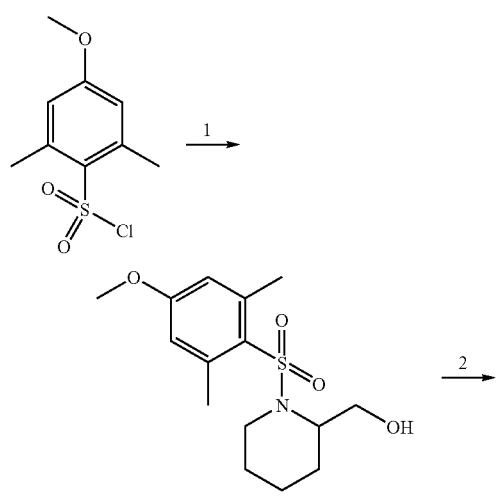

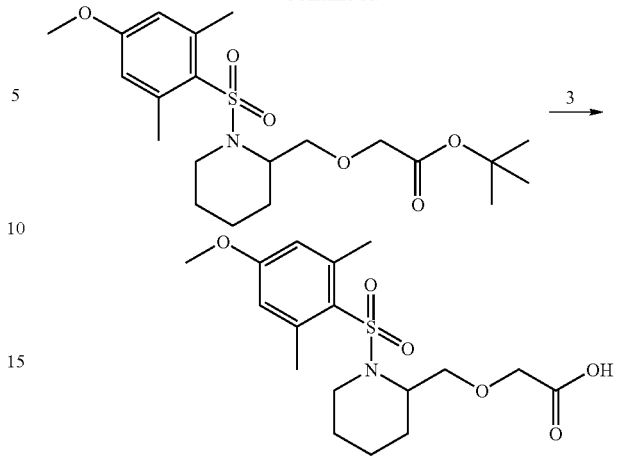

Stage 1. Triethylamine (125 mmol) was added to a solution of the amino alcohol (100 mmol) in MC (200 ml) and the mixture was cooled to 0° C. using an ice bath. The sulfonyl chloride (50 mmol) was then added as a solution in MC (100 ml) and the mixture was stirred at RT for 3 h. After addition of 0.5 M hydrochloric acid (100 ml), the organic phase was separated off, washed with water, dried over Na$_2$SO$_4$ and filtered and the solvent was removed in vacuo. The crude product was used in the next stage without further purification.

Stage 2. n-Bu$_4$NCl (10 mmol) was added to a solution of the product from stage 1 (31 mmol) in toluene (200 ml), the mixture was cooled to 0° C. and first aqueous 35% strength NaOH (200 ml) and then bromoacetic acid tert-butyl ester (46 mmol) were added dropwise. The reaction mixture was stirred for 3 h and then washed neutral with water and dried with Na$_2$SO$_4$ and the organic solvent was removed in vacuo. The crude product was purified by column chromatography (silica gel, heptane/ethyl acetate, 3:1).

Stage 3. The product from stage 2 (30 mmol) was dissolved in MC (200 ml), TFA (30 ml) was added and the mixture was stirred at RT for 2 h. The solvent was largely distilled off and the crude product was purified by recrystallization.

Preparation of 2-((1-(3,4-dichlorophenylsulfonyl)-1,2,3,4-tetrahydroquinolin-2-yl)methoxy)acetic acid AC6

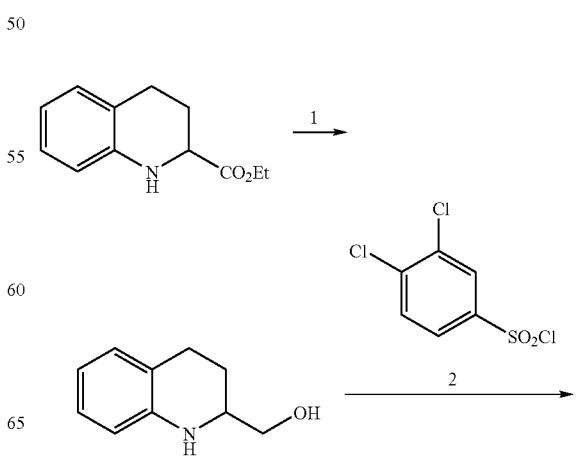

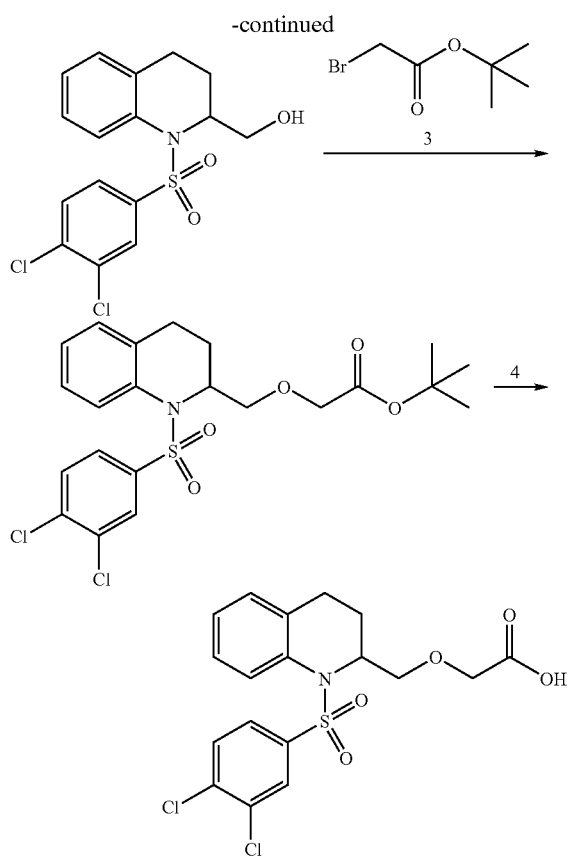

Stage 2. Pyridine (5 eq.), DMAP (0.5 eq.) and 3,4-dichlorobenzenesulfonyl chloride (1.2 eq.), dissolved in MC (50 ml), were added to a suspension, cooled to 0° C., of the alcohol (16 mmol) in MC (5 ml/mmol). After stirring at 0° C. for 5 h, MC was added and the mixture was washed with aqueous copper sulfate solution, water and sat. NaCl solution. After drying over $Na_2SO_4$ and filtration, the solvent was removed in vacuo. The product was purified via column: chromatography (5:95 ethyl acetate/MC). Yield: 80%.

Stage 3. A solution of the sulfonamide (16 mmol) dissolved in THF (100 ml) was added dropwise to a suspension, cooled to 0° C., of NaH (2 eq.) in THF (300 ml), while stirring. After stirring for 45 min at this temperature, a solution of bromoacetic acid tert-butyl ester (1.5 eq.) in THF (50 ml) was added. The reaction mixture was heated at 50° C. for 20 h. It was then cooled to 0° C., ice was added and the mixture was extracted with ethyl acetate. The organic phase was washed with aqueous sat. NaCl solution and dried over $Na_2SO_4$. After filtration, the solvent was removed in vacuo. The product was purified via column:chromatography (1:9 ethyl acetate/hexane). Yield: 50%.

Stage 4. TFA (13 eq.) was added to a solution of the tert-butyl ester (1 eq.) in MC (10 ml/mmol) at a temperature of 0° C., while stirring. After stirring for at 0° C. for 3 h, the solvent was removed in vacuo. The crude product was used without further working up.

Preparation of 2-(2-(N-Cyclopropyl-4-methoxy-2,6-dimethylphenyl-sulfonamido)ethoxy)acetic acid AC7

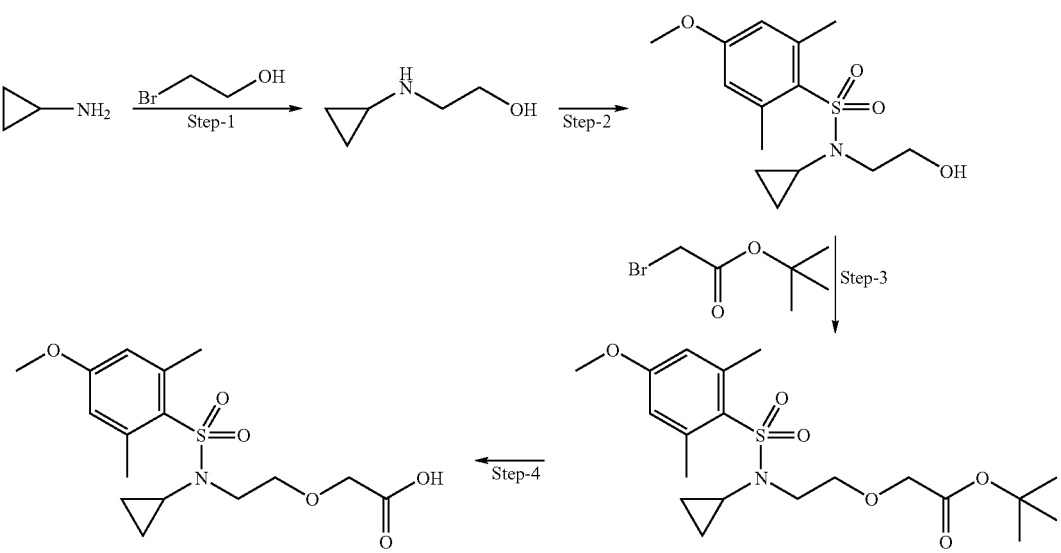

Stage 1. 1,2,3,4-Tetrahydroquinoline-2-carboxylic acid ethyl ester (25 mmol) in THF (5 ml/mol) was added dropwise to a suspension of LAH (2 eq.) in THF (50 ml) at 0° C. The reaction mixture was stirred at RT for 1 h and then heated under reflux for 4 h. After addition of aqueous sat. $Na_2SO_4$ solution, the mixture was filtered and the organic solvent was removed in vacuo. The product was purified via column chromatography (3:7 ethyl acetate/hexane). Yield: 50%.

Step-1: 2-(Cyclopropylamino)ethanol

A solution of cyclopropyl amine (20 mmol) and bromoethanol (8 mmol) in ethanol (20 ml) was heated at 50° C. for 16 h by which time the reaction was completed. The solvent was evaporated under reduced pressure, azeotroped with toluene (2×10 ml), dried and the crude product used for the next step without further purification. Yield: 65%

Step-2: N-Cyclopropyl-N-(2-hydroxyethyl)-4-methoxy-2,6-dimethylbenzenesulfonamide To a cold (0° C.) solution of 2-cyclopropylamino-ethanol (8 mmol) in dichloromethane (24 ml) and triethylamine (2.5 equiv.) a solution of 4-methoxy-2,6-dimethylbenzenesulfonyl chloride (7 mmol) in dichloromethane (12 ml) was added dropwise maintaining the temperature at 0° C. After complete addition the reaction mixture was stirred at 25° C. for 90 min by which time the reaction was complete (TLC). The reaction mixture was diluted with dichloromethane (200 ml) and washed with water and finally with brine. The organic layer was dried over sodium sulfate and evaporated to dryness to obtain the pure product. Yield: 20%

Step-3: tert-Butyl 2-(2-(N-cyclopropyl-4-methoxy-2,6-dimethylphenylsulfonamido)ethoxy)acetate To a cold solution of N-cyclopropyl-N-(2-hydroxyethyl)-4-methoxy-2,6-dimethylbenzenesulfonamide (3.3 mmol) in toluene (18 ml) was added tetrabutylammonium chloride (0.33 equiv.) and 35% sodium hydroxide solution (18 ml) at 0° C. To this cold reaction mixture tert-butyl bromoacetate (1.5 equiv.) was added dropwise maintaining the same temperature. After complete addition the reaction mixture was stirred at 25° C. for 90 min by which time the reaction was complete (TLC). The organic layer was then separated, washed with water until neutral pH, dried over sodium sulfate and evaporated to dryness to give the pure product. Yield: 90%

Step 4: 2-(2-(N-Cyclopropyl-4-methoxy-2,6-dimethylphenylsulfonamido)ethoxy)acetic acid (AC7)

To a dichloromethane solution (10 ml/mmol) of tert-butyl 2-(2-(N-cyclopropyl-4-methoxy-2,6-dimethylphenylsulfonamido)ethoxy)acetate (1 equiv.) was added TFA (13 equiv.) at 0° C. and the resulting reaction mixture was stirred at 25° C. for 2 h. The solvent was evaporated off and the product dried under vacuum to remove traces of TFA. The crude acid was used directly for the next step without any further purification.

Preparation of 2-(2-(2-Chloro-N-cyclopropyl-6-methylphenylsulfonamido)ethoxy)acetic acid AC8

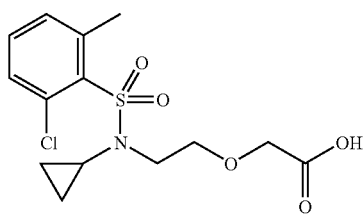 [SMILES: Cc1cccc(Cl)c1S(=O)(=O)N(CCOCC(=O)O)C1CC1]

Carboxylic acid AC8 was synthesized in analogy to carboxylic acid AC7 (2-(2-(N-cyclopropyl-4-methoxy-2,6-dimethylphenylsulfonamido)ethoxy)acetic acid).

Preparation of 2-(2-(N-Cyclopropyl-2-(trifluoromethyl)phenylsulfonamido)-ethoxy)acetic acid AC9

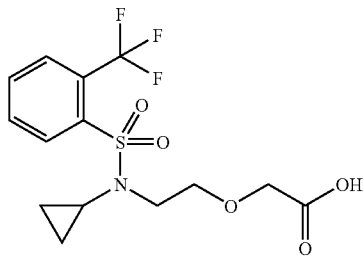 [SMILES: O=C(O)COCCN(C1CC1)S(=O)(=O)c1ccccc1C(F)(F)F]

Carboxylic acid AC9 was synthesized analogously to carboxylic acid AC7 (2-(2-(N-cyclopropyl-4-methoxy-2,6-dimethylphenylsulfonamido)ethoxy)acetic acid).

Preparation of (S)-2-((1-(4-Methoxy-2,6-dimethylphenylsulfonyl)indolin-2-yl)methoxy)acetic acid AC10

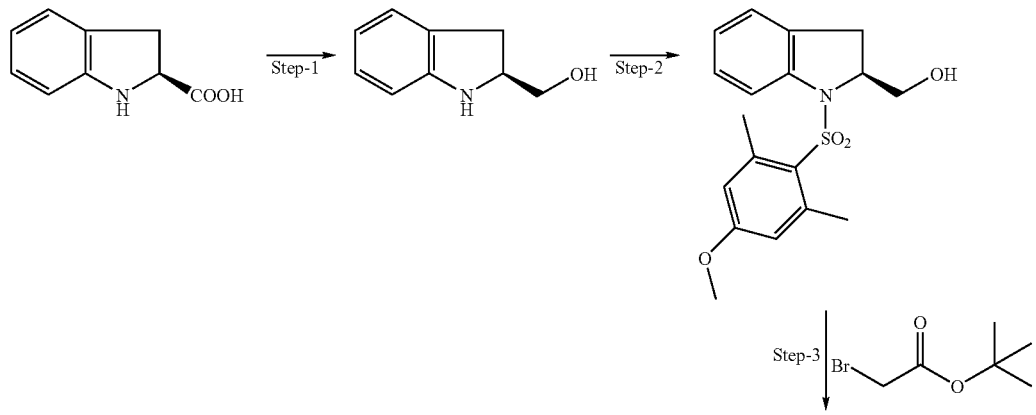

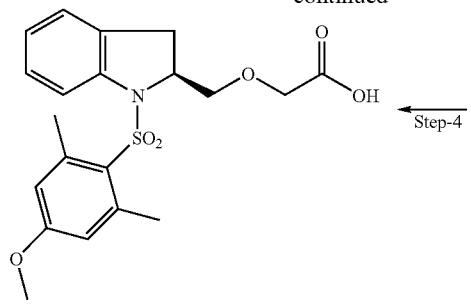
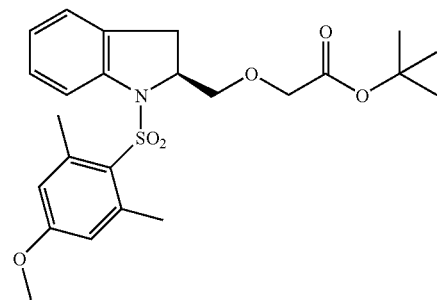

Step-1: (S)-Indolin-2-ylmethanol

To a solution of (S)-indoline-2-carboxylic acid (9.2 mmol, 1.0 equiv.) in THF (18 ml) was added dropwise $BH_3$-DMS solution (18.4 mmol, 2 equiv.) and the reaction mixture was heated to reflux for 12 h. The mixture was quenched with methanol (7.5 ml) and conc. HCl (2.5 ml) with cooling and was then refluxed for additional 2 h. The solvent was evaporated and the residue was basified with 40% NaOH solution and extracted with dichloromethane. The organic layer was washed with brine, dried over sodium sulfate and the solvent was evaporated under reduced pressure to give the crude product which was purified by silica gel column chromatography. Yield: 87%.

Step-2: (S)-(1-(4-Methoxy-2,6-dimethylphenylsulfonyl)indolin-2-yl)methanol

To a cold (0° C.) solution of (S)-indolin-2-ylmethanol (4.60 mmol, 1.2 equiv.) and triethylamine (2.5 equiv.) in dichloromethane (20 ml) was added dropwise 4-methoxy-2,6-dimethylbenzenesulfonyl chloride (3.83 mmol, 1.0 equiv.) in dichloromethane (5 ml) and the reaction mixture was stirred at room temperature for 2 h. The mixture was diluted with dichloromethane, washed successively with water and brine, and dried over sodium sulfate. The solvent was evaporated under reduced pressure and the crude product was purified by silica gel column chromatography. Yield: 72%.

Step-3: (S)-tert-Butyl 2-((1-(4-methoxy-2,6-dimethylphenylsulfonyl)indolin-2-yl)methoxy)acetate To a cold (0° C.) mixture of (S)-(1-(4-methoxy-2,6-dimethylphenylsulfonyl)-indolin-2-yl)methanol (3.3 mmol, 1.0 equiv.) and tetrabutyl ammonium chloride (1.1 mmol, 0.33 equiv.) in toluene (20 ml) was added 35% NaOH solution (10 ml). Tertiary butyl bromo acetate (1.5 equiv.) was then added to the reaction mixture and it was stirred at room temperature for 2 h. The organic layer was separated and the aqueous layer was extracted with ethyl acetate. The combined organic layers were successively washed with water and brine, and dried over sodium sulfate. The solvent was evaporated under reduced pressure to give the crude product which was purified by silica gel column chromatography. Yield: 50%.

Step-4: (S)-2-((1-(4-Methoxy-2,6-dimethylphenylsulfonyl)indolin-2-yl)methoxy)acetic acid (AC10)

To a cold (0° C.) solution of (S)-tert-butyl 2-((1-(4-methoxy-2,6-dimethyl-phenylsulfonyl)indolin-2-yl)methoxy)acetate (0.5 mmol) in dichloromethane (6 ml) was added TFA (1.5 ml) and the reaction mixture was stirred at room temperature for 2 h. The solvent was evaporated under reduced pressure and the crude product was used in the next step.

Synthesis of acid building block AC-11: 2-((4-(4-Methoxy-2,6-dimethyl-phenylsulfonyl)-3,4-dihydro-2H-benzo[b][1,4]oxazin-3-yl)methoxy)acetic acid (AC-11)

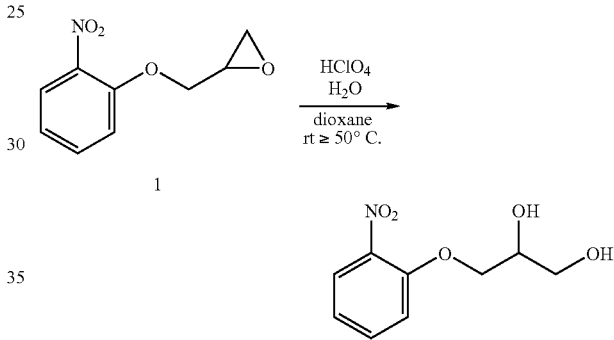

2. Perchloric acid (3.30 mL, 38.2 mmol) was added to a solution of 1 (37.3 g, 191 mmol) in dioxane (746 mL) and $H_2O$ (568 mL) and the reaction mixture was stirred at 50° C. overnight. The reaction mixture was concentrated to half its volume and aqueous saturated $NaHCO_3$ was added. The $H_2O$ layer was extracted with $CH_2Cl_2$ (2×) and the combined organic layer was washed with brine, dried ($Na_2SO_4$) and concentrated. Purification by column chromatography (silica, heptane/EtOAc, 2:3) yielded 2 (30.6 g, 75%).

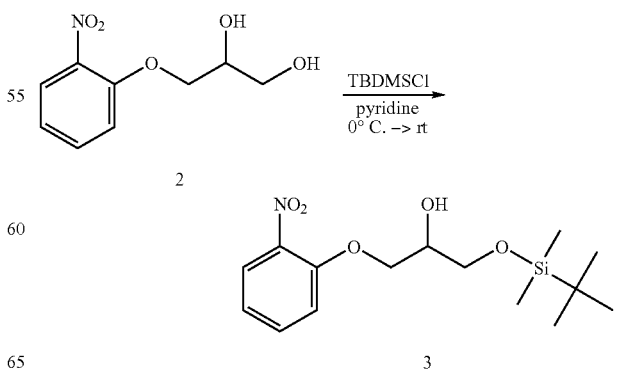

3. To a solution of 2 (30.6 g, 143 mmol) in pyridine (75 mL) was added tert-butyldimethylsilyl chloride (23.8 g, 158 mmol) while cooling with an icebath. The reaction mixture was stirred at room temperature for 2 h and afterwards concentrated and co-evaporated with toluene. The residue was dissolved in EtOAc, washed with H₂O, brine, dried (Na₂SO₄) and concentrated to give 3 (46.7 g, 99%).

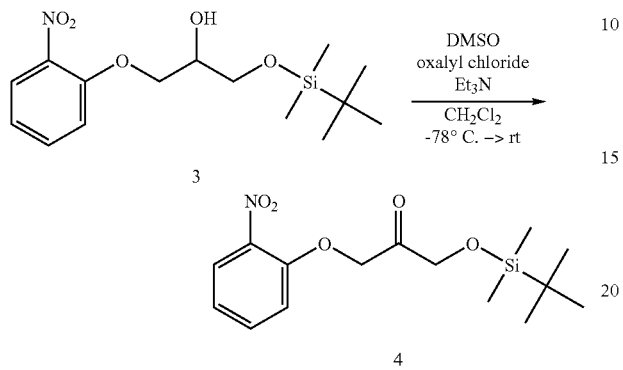

4. A solution of DMSO (21.24 mL, 299 mmol) in CH₂Cl₂ (600 mL) was added dropwise to a solution of oxalyl chloride (15.0 mL, 171 mmol) in CH₂Cl₂ (300 mL) in 30 min while maintaining the internal temperature below −65° C. A solution of 3 (46.7 g, 142 mmol) in CH₂Cl₂ (300 mL) was added dropwise in 15 min. while maintaining the temperature below −65° C. The reaction mixture was stirred an additional 45 minutes at −78° C., after which Et₃N (99.0 mL, 712 mmol) was added. After the reaction mixture was stirred at −78° C. for 45 min, the reaction mixture was allowed to warm to room temperature and stirring was continued for an additional hour. The reaction mixture was washed with H₂O and brine, dried (Na₂SO₄) and concentrated. The residue was dissolved in Et₂O, filtered and the filtrate was concentrated and crystallized (Et₂O/heptane) to result in 4 (30.9 g, 67%). The mother liquor was concentrated and crystallized (Et₂O/heptane) and gave extra 4 (2.27 g, 5%).

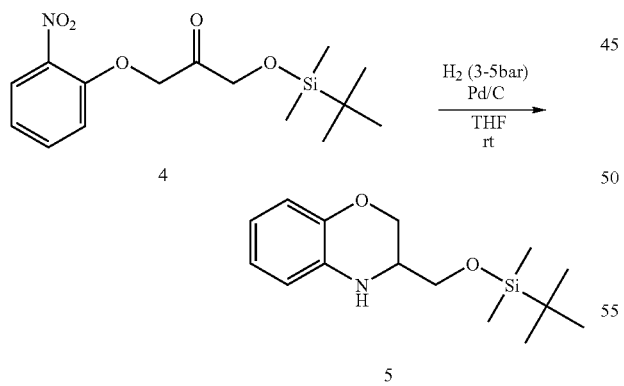

5. A mixture of 4 (18 g, 55.3 mmol) and 10% Pd/C (1.8 g, 1.7 mmol) in dry THF (150 mL) was stirred under an hydrogen atmosphere of ~3 bar for 2 days and then under an hydrogen atmosphere of 5 bar for 1 d. The reaction mixture was filtered over Celite and eluted with THF. The filtrate was concentrated and 10% Pd/C (1.8 g, 1.7 mmol) was added to the residue in dry THF (150 mL) and the resulting reaction mixture was stirred under an hydrogen atmosphere of ~5 bar for 1 d. The reaction mixture was filtered over Celite and eluted with THF. The filtrate was concentrated and purified by column chromatography (silica, heptane/Et₂O, 9:1) to yield 5 (7.11 g, 46%).

Another batch of 4 (15.06 g, 46.3 mmol) and Pd/C 10% Pd/C (1.5 g, 1.4 mmol) in dry THF (150 mL) was stirred under an hydrogen atmosphere (~5 bar) for 2 days. The reaction mixture was filtered over Celite and eluted with THF. The filtrate was concentrated and purified by column chromatography (silica, heptane/Et₂O, 9:1) to yield extra 5 (3.20 g, 25%).

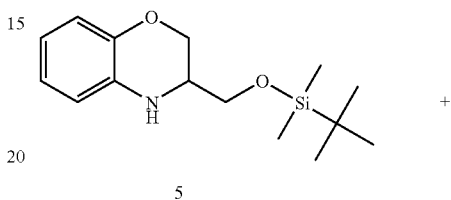

+

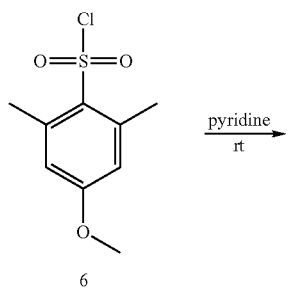

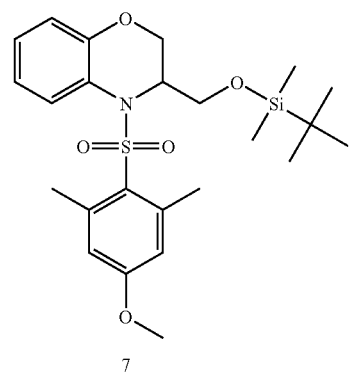

7. Sulfonyl chloride 6 (8.96 g, 38.2 mmol) was added to a solution of 5 (9.70 g, 34.7 mmol) in pyridine (8.42 mL) and the reaction mixture was stirred at room temperature for 2 d. The reaction mixture was concentrated, dissolved in CH₂Cl₂ and washed with H₂O, brine, dried (Na₂SO₄) and concentrated to give crude 7, which was directly used in the next step.

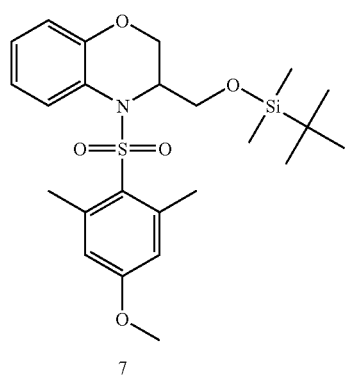

7

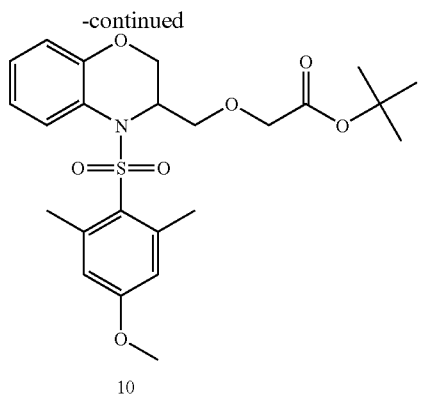

10

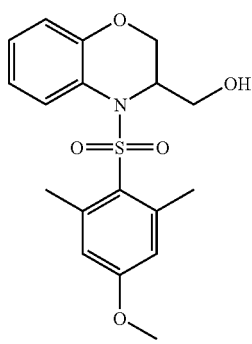

8

8. Crude 7 was dissolved in EtOH (~100 mL) and H₂O (~100 mL) with heating and was left standing overnight. The reaction mixture was concentrated, dissolved in CH₂Cl₂, washed with aqueous saturated NaHCO₃, brine, dried (Na₂SO₄) and concentrated. The residue was solidified with EtOAc/heptane (2:1) and some CH₂Cl₂. The resulting precipitate was washed with EtOAc/heptane (2:1) and dried on filter to yield 8 (9.68 g, 77% over 2 steps).

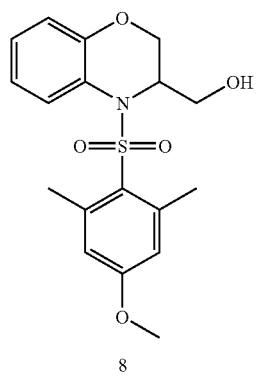

8

+

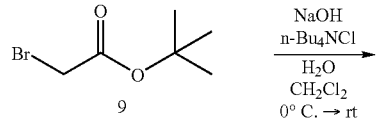

9

10. To an ice-cooled solution of 8 (9.68 g, 26.6 mmol) and n-Bu₄NCl (2.44 g, 8.79 mmol) in CH₂Cl₂ (130 mL) was sequentially added aqueous 35% NaOH solution (130 mL) and tert-butyl bromoacetate (9, 11.6 mL, 80.0 mmol). The reaction mixture was stirred at room temperature for 4.5 h, after which H₂O was added. The organic layer was separated, washed with H₂O (2×), dried (Na₂SO₄) and concentrated. The residue was purified by column chromatography (silica, heptane/EtOAc, 4:1→3:1) to provide 10 (11.9 g, 94%).

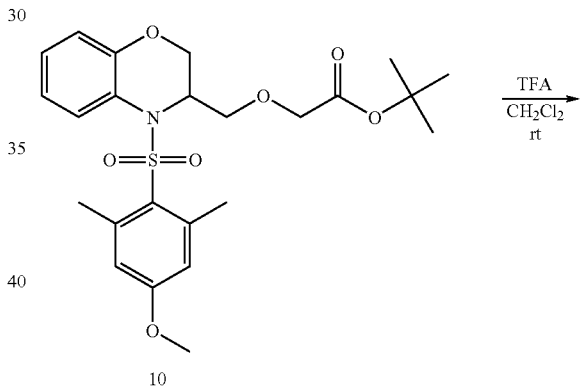

10

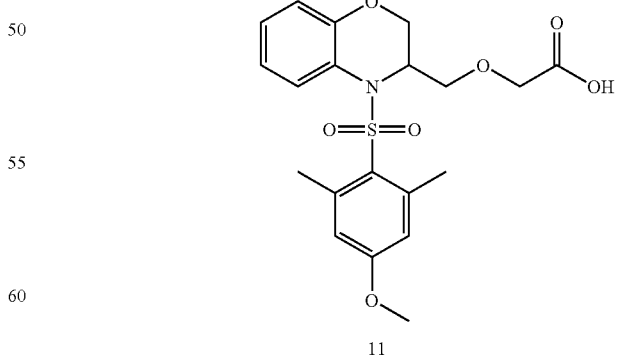

11

11. A solution of 10 (11.80 g, 24.7 mmol) and TFA (25 mL, 324 mmol) in CH₂Cl₂ (125 mL) was stirred at room temperature for 2.5 h. The reaction mixture was concentrated, co-

Synthesis of acid building block AC-12: 2-((4-(2-Chloro-6-methylphenyl-sulfonyl)-3,4-dihydro-2H-benzo[b][1,4]oxazin-3-yl)methoxy)acetic acid (AC-12)

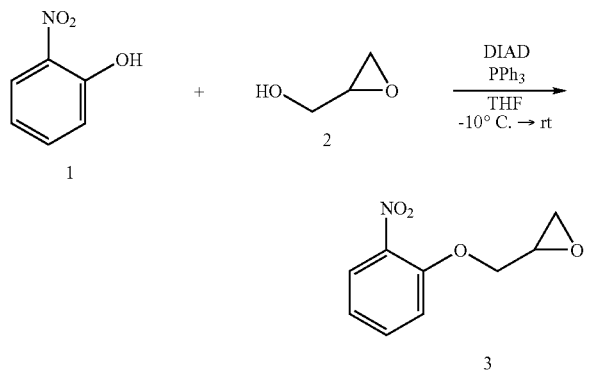

3. A solution of DIAD (149 mL, 719 mmol) in dry THF (200 mL) was added in 30 min to a solution of 2-nitrophenol (1, 100 g, 719 mmol), glycidol (2, 50.0 mL, 719 mmol) and PPh$_3$ (189 g, 719 mmol) in dry THF (800 mL) while keeping the temperature between −10° C. and −5° C. The reaction mixture was stirred for 1 h at this temperature range, after which stirring was continued at room temperature overnight. The reaction mixture was concentrated and the residue was stirred up in toluene, filtered and concentrated. Purification by column chromatography (silica, toluene/acetone, 95:5) afforded 3 (114.25 g, 81%).

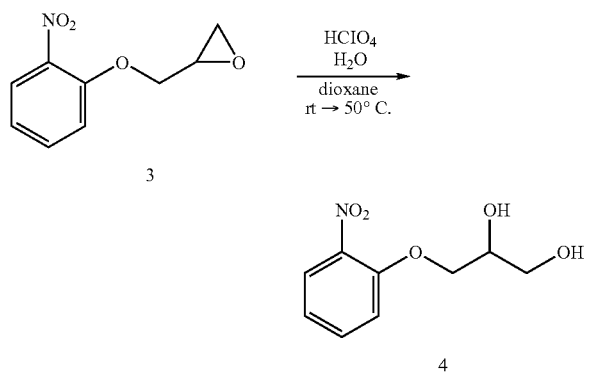

4. Perchloric acid (4.96 mL, 57.4 mmol) was added to a solution of 3 (56.02 g, 287 mmol) in dioxane (1124 mL) and H$_2$O (856 mL) and the reaction mixture was stirred at 50° C. overnight. The reaction mixture was concentrated to half its volume and aqueous saturated NaHCO$_3$ was added. The H$_2$O layer was extracted with CH$_2$Cl$_2$ (2×) and the combined organic layer was washed with brine, dried (Na$_2$SO$_4$) and concentrated. Purification by column chromatography (silica, heptane/EtOAc, 2:3→1:2) yielded 4 (47.45 g, 78%).

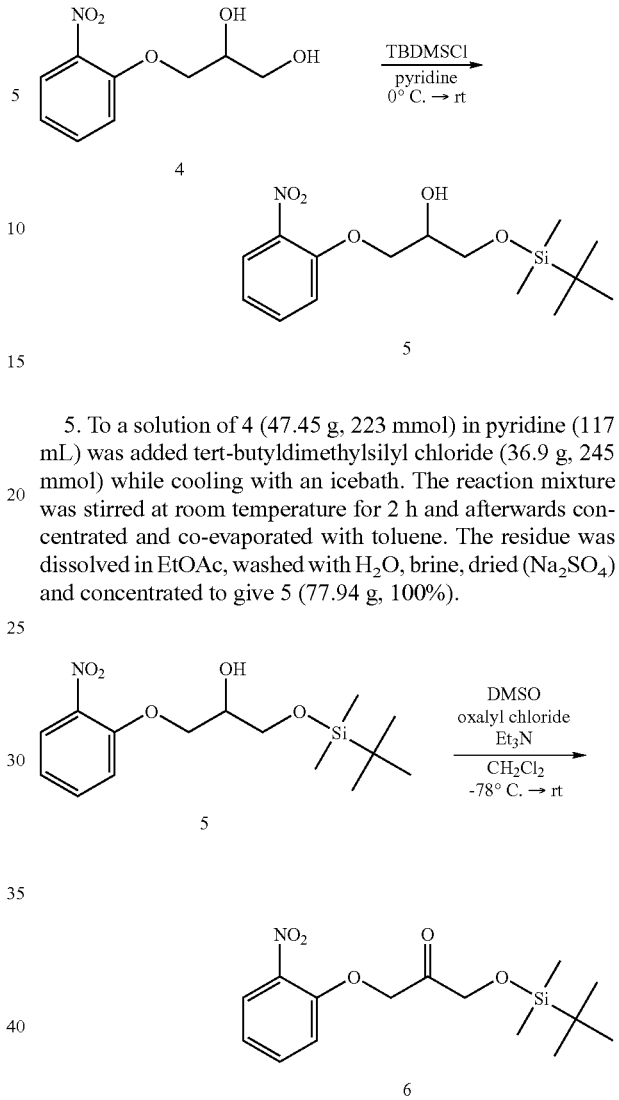

5. To a solution of 4 (47.45 g, 223 mmol) in pyridine (117 mL) was added tert-butyldimethylsilyl chloride (36.9 g, 245 mmol) while cooling with an icebath. The reaction mixture was stirred at room temperature for 2 h and afterwards concentrated and co-evaporated with toluene. The residue was dissolved in EtOAc, washed with H$_2$O, brine, dried (Na$_2$SO$_4$) and concentrated to give 5 (77.94 g, 100%).

6. A solution of DMSO (35.0 mL, 500 mmol) in CH$_2$Cl$_2$ (1 L) was added dropwise to a solution of oxalyl chloride (25.0 mL, 286 mmol) in CH$_2$Cl$_2$ (500 mL) in 1 h while maintaining the internal temperature below −65° C. A solution of 5 (77.94 g, 221 mmol) in CH$_2$Cl$_2$ (500 mL) was added dropwise in 30 min. while maintaining the temperature below −65° C. The reaction mixture was stirred an additional 45 minutes at −78° C., after which Et$_3$N (166 mL, 1.190 mol) was added. After the reaction mixture was stirred at −78° C. for 45 min, the reaction mixture was allowed to warm to room temperature and stirring was continued for an additional hour. The reaction mixture was washed with H$_2$O and brine, dried (Na$_2$SO$_4$) and concentrated. The residue was dissolved in Et$_2$O, filtered and the filtrate was concentrated. The residue was filtered over a small layer of silica (heptane/EtOAc, 4:1) and crystallized (i-Pr$_2$O/heptane) to result in 6 (23.15 g, 32.1%). The mother liquor was concentrated and crystallized (heptane) to give extra 6 (3.20 g, 4%). The mother liquor was concentrated and purified by column chromatography (silica, heptane/EtOAc, 4:1→3:1), followed by crystallization (Et$_2$O/heptane) to yield extra 6 (4.16 g, 6%). All crystals were combined to give 6 (30.51 g, 42%).

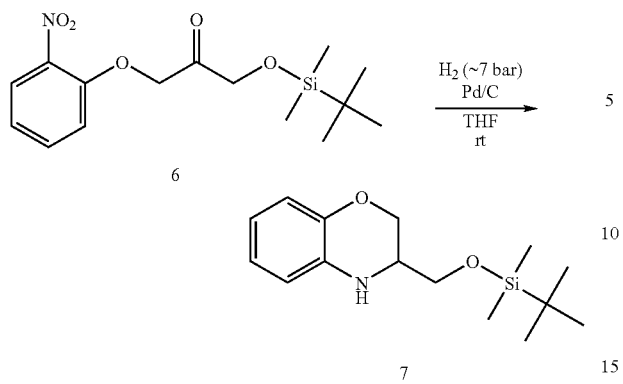

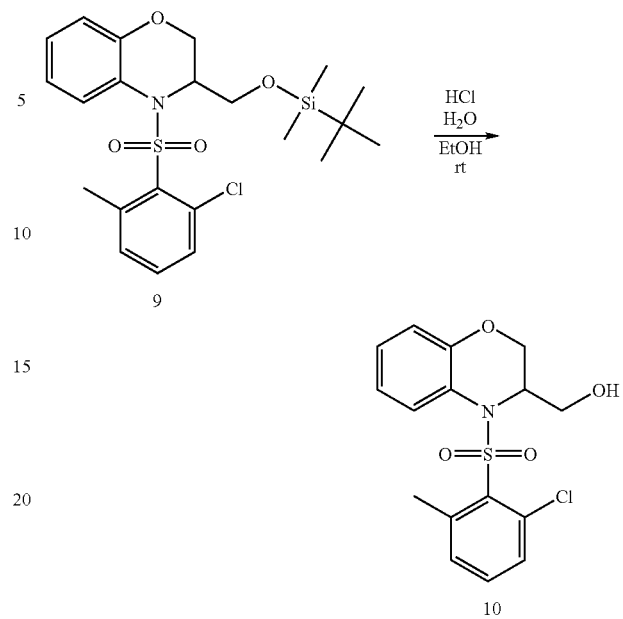

7. A mixture of 6 (24.36 g, 74.9 mmol) and 10% Pd/C (2.4 g, 23 mmol) in EtOH (350 mL) in a 1 L autoclave was stirred at 60° C. under a nitrogen atmosphere. After pressurizing the reaction vessel with hydrogen to ~7 bar, the pressure dropped rapidly while stirring vigorously. The pressurizing the reaction vessel with hydrogen to ~7 bar was repeated until the pressure remained almost constant for 10 min. The reaction mixture was then stirred at 60° C. and 4 bar overnight. The reaction mixture was filtered over Celite and eluted with EtOH. The filtrate was concentrated, co-evaporated with heptane and purified by column chromatography (silica, heptane/i-Pr₂O, 9:1→4:1) to yield 7 (14.75 g, 71%).

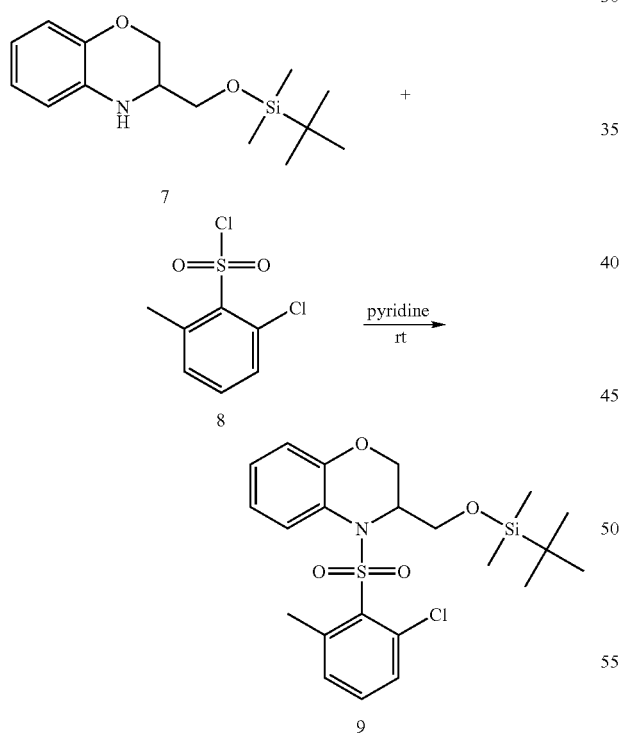

7. 2-chloro-6-methylbenzenesulfonyl chloride (8, 7.82 g, 34.8 mmol) was added to a solution of 7 (8.83 g, 31.6 mmol) in pyridine (7.67 mL, 95.0 mmol) and the reaction mixture was stirred at room temperature overnight. CH₂Cl₂ and H₂O were added to the reaction mixture and the organic layer was separated, washed with H₂O, brine, dried (Na₂SO₄) and concentrated to give crude 9, which was directly used as such in the next step.

10. Aqueous 1 M HCl (50 mL, 50 mmol) was added to crude 9 in EtOH (200 mL) and the reaction mixture was stirred at room temperature overnight. The reaction mixture was concentrated, dissolved in CH₂Cl₂, washed with aqueous saturated NaHCO₃, dried (Na₂SO₄) and concentrated. The residue was purified by column chromatography (silica, heptane/EtOAc: 2:1) to yield 10 (7.75 g, 69%, 2 steps).

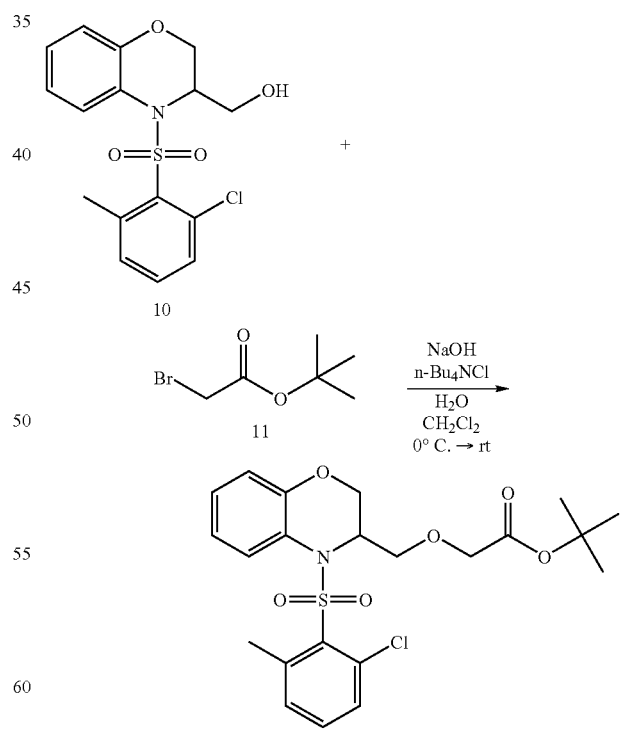

12. To an ice-cooled solution of 10 (7.75 g, 21.9 mmol) and n-Bu₄NCl (2.00 g, 7.23 mmol) in CH₂Cl₂ (110 mL) was sequentially added aqueous 35% NaOH solution (110 mL)

and tert-butyl bromoacetate (11, 9.57 mL, 65.7 mmol). The reaction mixture was stirred at room temperature for 4 h, after which H$_2$O was added. The organic layer was separated, washed with H$_2$O and brine, dried (Na$_2$SO$_4$) and concentrated. The residue was purified by column chromatography (silica, heptane/EtOAc, 4:1) to provide 12 (9.98 g, 92%).

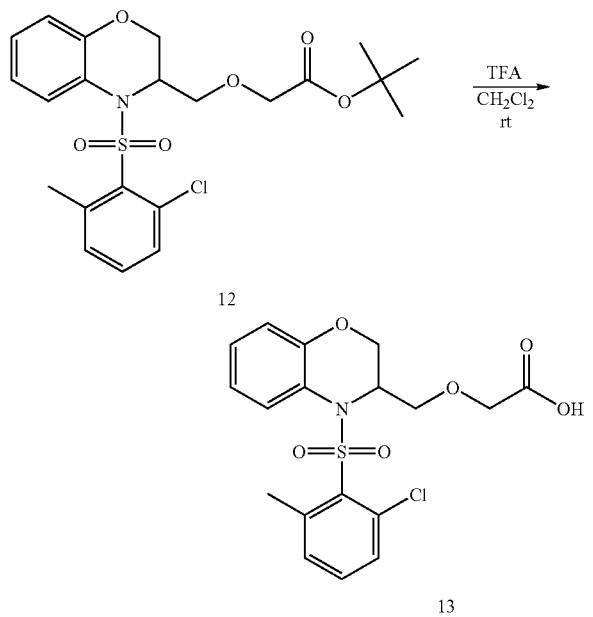

13. A solution of 12 (9.88 g, 20.1 mmol) and TFA (20 mL, 260 mmol) in CH$_2$Cl$_2$ (100 mL) was stirred at room temperature for 2 h. The reaction mixture was concentrated, co-evaporated with toluene (2×) and CH$_2$Cl$_2$ (2×). The residue was transferred to a jar with CH$_2$Cl$_2$, concentrated and dried under vacuum overnight to furnish 13 (8.50 g, '103'%).

Synthesis of acid building block AC-13: 3-((1-(4-Methoxy-2,6-dimethyl-phenylsulfonyl)piperidin-2-yl)methoxy)propanoic acid (AC-13)

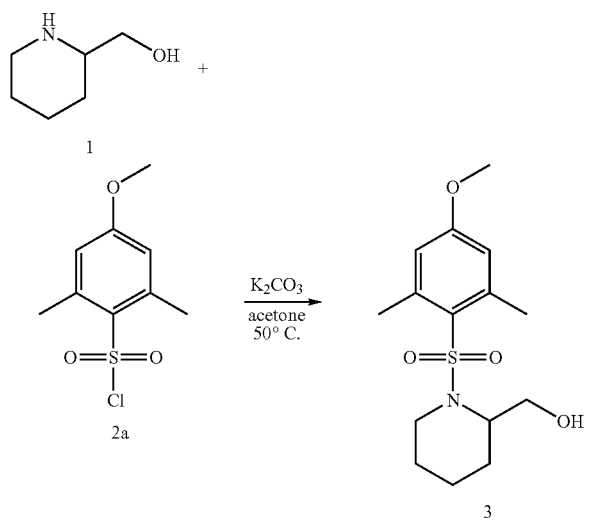

3. 2-Piperidinemethanol (1, 8.1 g, 70.11 mmol) was suspended in acetone (350 mL). K$_2$CO$_3$ (19.4 g, 140.22 mmol) was added followed by sulfonyl chloride 2a (18.1 g, 77.12 mmol). The mixture was stirred overnight at 50° C. After cooling to room temperature, the reaction mixture was filtered and the filtrate was evaporated to dryness. Purification by column chromatography (silica, heptane/EtOAc 2:1) gave 3 (12.9 g, 59%) as a white solid.

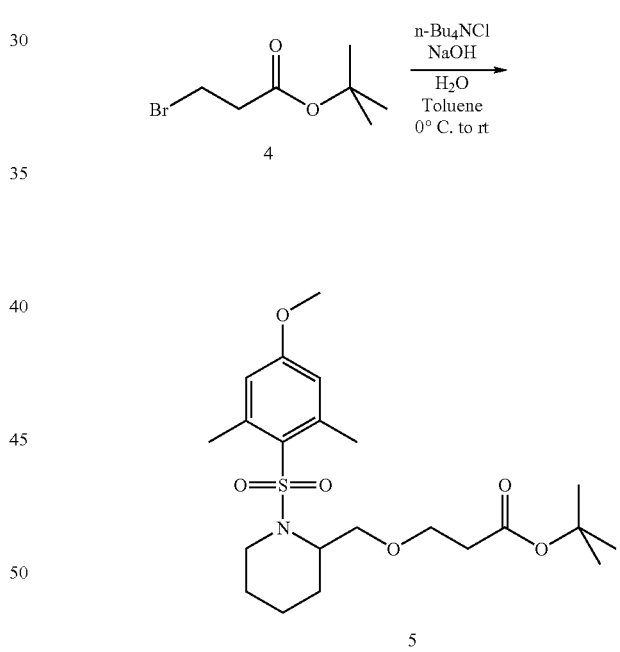

5. To a solution of alcohol 3 (12.8 g, 40.84 mmol) in toluene (200 mL) was added Bu$_4$NCl (3.7 g, 13.48 mmol). The reaction mixture was cooled to 0° C. after which aqueous 35% NaOH (250 mL) was added followed by a dropwise addition of tert-butyl 3-bromopropionate (4, 8.2 mL, 49.01 mmol) in toluene (50 mL). The mixture was stirred overnight at room temperature. The organic layer was separated and washed with H$_2$O until neutral, dried (Na$_2$SO$_4$), concentrated and co-evaporated with CH$_2$Cl$_2$ (3×). Purification by column chromatography (silica, heptane/EtOAc 4:1) gave 5 (11.2 g, 62%) as a yellow oil.

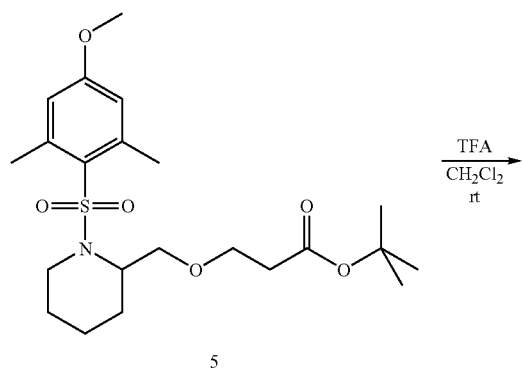

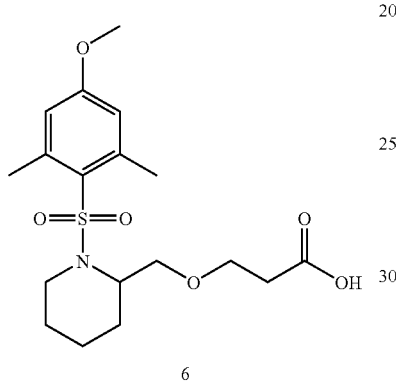

6. tert-Butyl ester 5 (10.9 g, 24.68 mmol) was dissolved in CH₂Cl₂ (150 mL). TFA (75 mL) was added and the mixture was stirred overnight at room temperature. The reaction mixture was concentrated in vacuo and co-evaporated with toluene (3×) and CH₂Cl₂ (3×). The crude product was purified by column chromatography (silica, heptane/EtOAc 2:1+2% HOAc). Co-evaporation with toluene (2×) and CH₂Cl₂ (3×) gave 6 (9.2 g, 97%) as a yellow oil.

Synthesis of acid building block AC-14: 2-(2-(1-(4-Methoxy-2,6-dimethylphenylsulfonyl)piperidin-2-yl)ethoxy)acetic acid (AC-14)

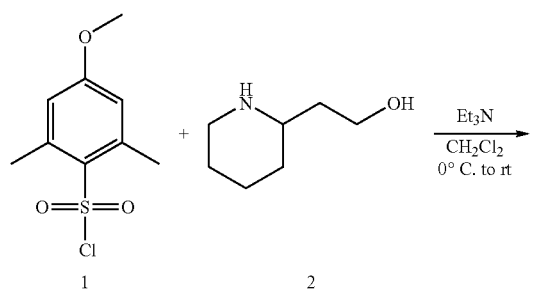

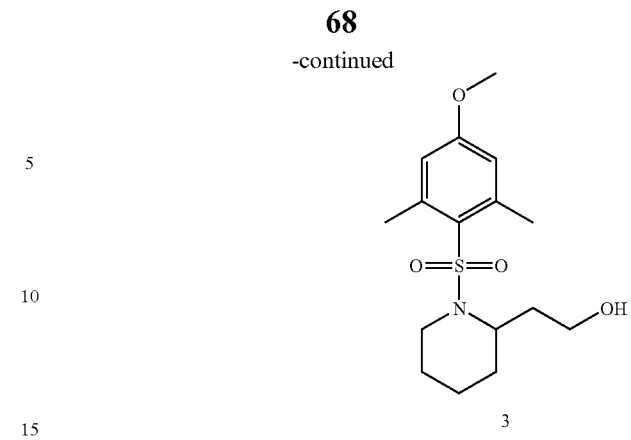

3. To a solution of 2-piperidineethanol (2, 5.63 g, 43.6 mmol) in CH₂Cl₂ (200 mL) was added Et₃N (14.1 mL, 109 mmol). At 0° C. was added 4-methoxy-2,6-dimethylbenzenesulfonyl chloride (1, 10.23 g, 43.6 mmol). The reaction mixture was stirred for 1 h at 0° C. and overnight at room temperature. Aqueous 1 M HCl (150 mL) was added and after separation of the layers the organic layer was washed with brine (150 mL), dried (Na₂SO₄) and evaporated to dryness to afford compound 3 (14.85 g, '104%').

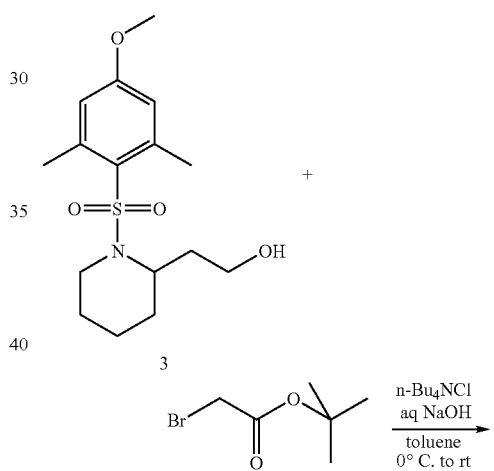

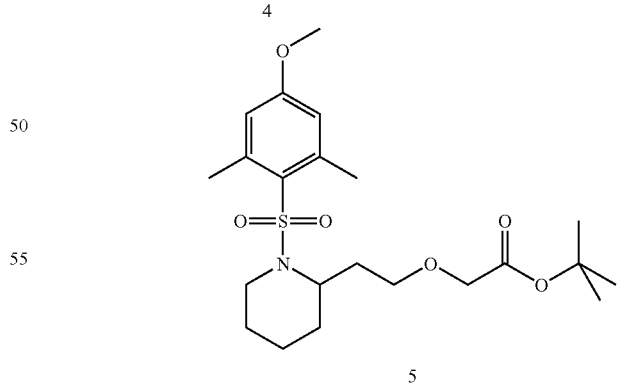

5. To a solution of alcohol 3 (14.8 g, max. 43.6 mmol) in toluene (200 mL) was added n-Bu₄NCl (4.04 g, 14.5 mmol). After cooling to 0° C., an aqueous 35% NaOH solution (200 mL) was added, followed by a dropwise addition of tert-butyl bromoacetate (4, 9.53 mL, 65.4 mmol). The reaction mixture was stirred at room temperature for 3 h. The organic layer was separated and washed with H₂O (3×200 mL), dried (Na₂SO₄) and evaporated to dryness. Purification by column chromatography (silica, heptane/EtOAc, 4:1) yielded compound 5 (12.90 g, 67%, 2 steps).

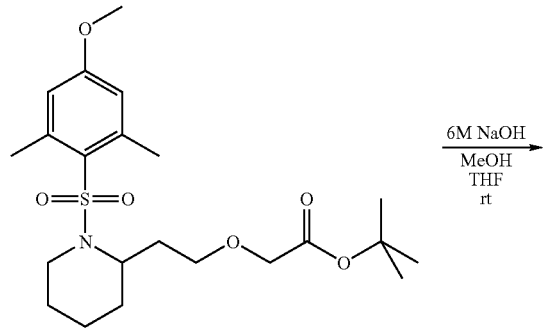

6. To a solution of ester 5 (12.90 g, 29.2 mmol) in THF (95 mL) and MeOH (95 mL) was added aqueous 6 M NaOH (95 mL). After 1 h organic solvents were evaporated and aqueous 6 M HCl (95 mL) was added at 0° C. The mixture was extracted with EtOAc (500 mL), dried (Na₂SO₄) and co-evaporated with Et₂O (2×) to afford compound 6 (11.07 g, 98%).

Synthesis of acid building block AC-15: 4-(N-Methyl-3-(trifluoromethyl)-phenylsulfonamido)butanoic acid (AC-15)

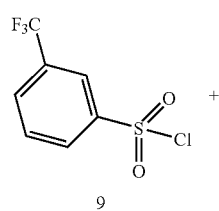

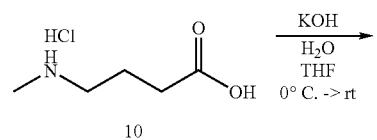

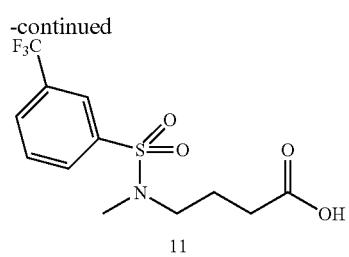

11. To a solution of KOH (16.5 g, 294 mmol) in H₂O (75 mL) was added 4-(methylamino)butyric acid hydrochloride (10, 15.1 g, 98.1 mmol) and the reaction mixture was cooled with an icebath. A solution of 3-(trifluoromethyl)benzenesulfonyl chloride (9, 12.0 g, 49.1 mmol) in THF (75 mL) was added dropwise to the reaction mixture and stirring was continued at room temperature overnight. Aqueous 6 M HCl (75 mL) was added to the reaction mixture while cooling with an icebath, after which CH₂Cl₂ was added. The organic layer was separated, washed with brine, dried (Na₂SO₄), concentrated and co-evaporated with a minimal amount of Et₂O. Crystallization of the residue out of EtOAc/heptane resulted in 11 (11.32 g, 71%).

Synthesis instructions for the preparation of 2-(2-(4-methoxy-N,2,3,6-tetramethylphenylsulfonamide)ethoxy)acetic acid AC16

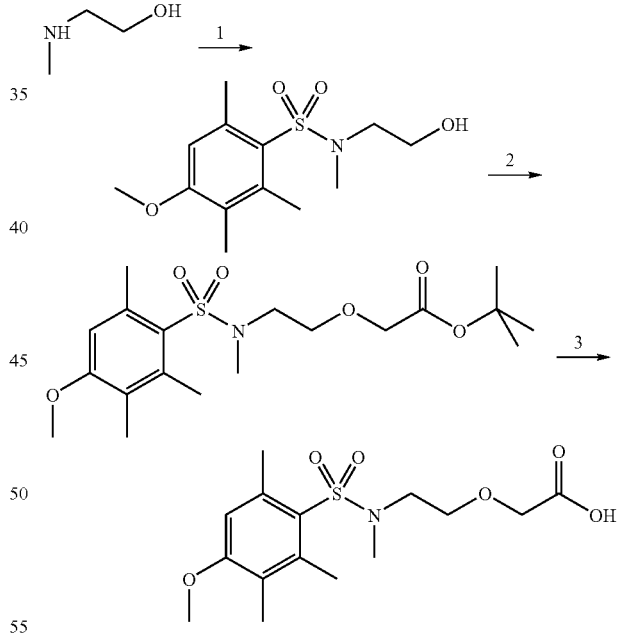

Stage 1. A solution of 4-methoxy-2,3,6-trimethylbenzenesulfonyl chloride (2.29 g, 9.19 mmol) in THF (30 ml) was added dropwise to a solution of 2-methyl-aminoethanol (0.89 g, 0.95 ml, 11.8 mmol) and Et₃N (5 ml) in THF (15 ml) at 0° C. The mixture was subsequently stirred at RT for 5 h and then concentrated in vacuo, the residue was taken up in NaHCO₃ solution. and the mixture was extracted with EtOAc (3×30 ml). The combined organic phases were dried with Na₂SO₄ and concentrated in vacuo. Yield: 2.38 g (90%)

Stage 2. 35% aq. sodium hydroxide solution (40 ml) was added to a solution of N-(2-hydroxyethyl)-4-methoxy-2,3,6, N-tetramethylbenzenesulfonamide (2.34 g, 8.2 mmol) and tetra-n-butylammonium hydrogen sulfate (611 mg, 1.8 mmol) in toluene (40 ml) at 0° C. A solution of bromoacetic acid tert-butyl ester (2.40 g, 1.82 ml, 12.3 mmol) in toluene (35 ml) was then added dropwise to the intensively stirred two-phase system. The mixture was subsequently stirred at RT for 2 h, the aqueous phase was then separated off and the organic phase was washed neutral with water (3×40 ml). The organic phase was dried with $Na_2SO_4$ and concentrated in vacuo and the residue was purified by flash chromatography with EtOAc/cyclohexane (1:3). Yield: 2.50 g (76%)

Stage 3. First triethylsilane (1.12 g, 1.54 ml, 9.6 mmol) and then trifluoroacetic acid (5 ml) were added to a solution of {2-[(4-methoxy-2,3,6-trimethylbenzene-sulfonyl)-methylamino]-ethoxy}-acetic acid tert-butyl ester (2.48 g, 6.18 mmol) in MC (50 ml) and the mixture was stirred at RT for 5 h. The mixture was then concentrated in vacuo, the residue was taken up repeatedly in toluene and the mixture was in each case concentrated again. The crude product was dissolved in EtOAc and the solution was extracted with 5% $NaHCO_3$ solution (3×50 ml). The combined aqueous phases were adjusted to pH 1 with conc. hydrochloric acid and extracted again with EtOAc (3×50 ml). The combined EtOAc phases were dried with $Na_2SO_4$ and concentrated in vacuo. Yield: 2.41 g (>99%)

Preparation of the Amine Units

The following amine units were employed for synthesis of the compounds according to the invention:

| Amine unit | Structure | Name |
|---|---|---|
| AM1 | 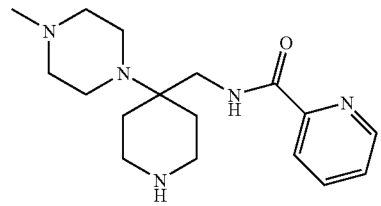 [SMILES: CN1CCN(C2(CNC(=O)c3ccccn3)CCNCC2)CC1] | N-((4-(4-Methylpiperazin-1-yl)piperidin-4-yl)methyl)picolinamide |
| AM2 | 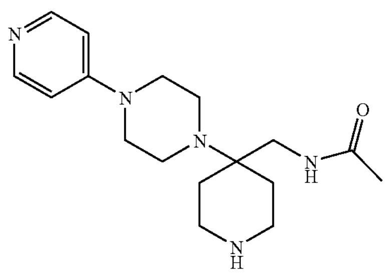 [SMILES: CC(=O)NCC1(N2CCN(c3ccncc3)CC2)CCNCC1] | N-((4-(4-(Pyridin-4-yl)piperazin-1-yl)piperidin-4-yl)methyl)acetamide |
| AM3 | 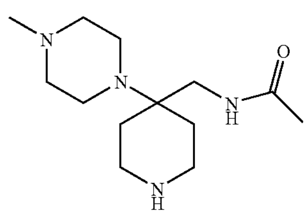 [SMILES: CC(=O)NCC1(N2CCN(C)CC2)CCNCC1] | N-((4-(4-Methylpiperazin-1-yl)piperidin-4-yl)methyl)acetamide |
| AM4 | 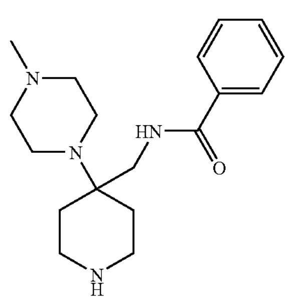 [SMILES: CN1CCN(C2(CNC(=O)c3ccccc3)CCNCC2)CC1] | N-((4-(4-Methylpiperazin-1-yl)piperidin-4-yl)methyl)benzamide |

-continued

| Amine unit | Structure | Name |
|---|---|---|
| AM5 | 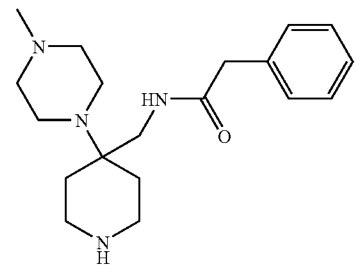 [SMILES: CN1CCN(C2(CNC(=O)Cc3ccccc3)CCNCC2)CC1] | N-((4-(4-Methylpiperazin-1-yl)piperidin-4-yl)methyl)-2-phenylacetamide |
| AM6 | 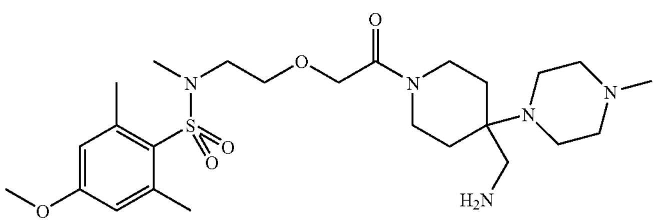 | N-(2-(2-(4-(Aminomethyl)-4-(4-methylpiperazin-1-yl)piperidin-1-yl)-2-oxoethoxy)ethyl)-4-methoxy-N,2,6-trimethylbenzenesulfonamide |
| AM7 | 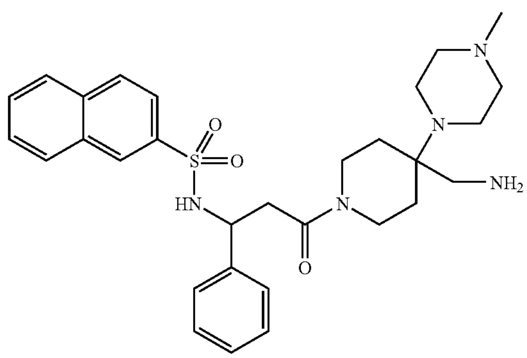 [SMILES: CN1CCN(C2(CN)CCN(C(=O)CC(NS(=O)(=O)c3ccc4ccccc4c3)c3ccccc3)CC2)CC1] | N-(3-(4-(Aminomethyl)-4-(4-methylpiperazin-1-yl)piperidin-1-yl)-3-oxo-1-phenylpropyl)naphthalene-2-sulfonamide |
| AM8 | 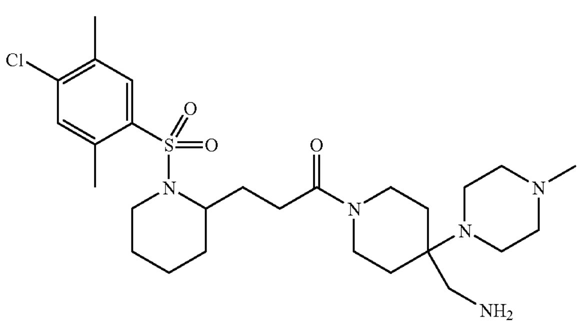 [SMILES: Cc1cc(S(=O)(=O)N2CCCCC2CCC(=O)N2CCC(CN)(N3CCN(C)CC3)CC2)c(C)cc1Cl] | 1-(4-(Aminomethyl)-4-(4-methylpiperazin-1-yl)piperidin-1-yl)-3-(1-(4-chloro-2,5-dimethylphenylsulfonyl)piperidin-2-yl)propan-1-one |
| AM9 | 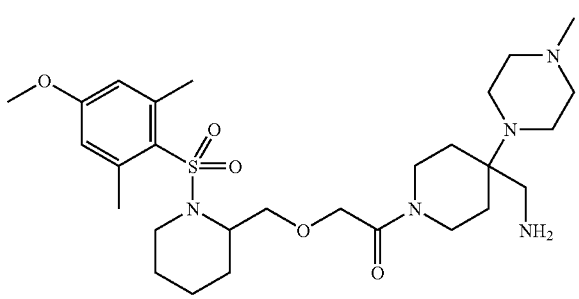 | 1-(4-(Aminomethyl)-4-(4-methylpiperazin-1-yl)piperidin-1-yl)-2-((1-(4-methoxy-2,6-dimethylphenylsulfonyl)piperidin-2-yl)methoxy)ethanone |

| Amine unit | Structure | Name |
|---|---|---|
| AM10 | 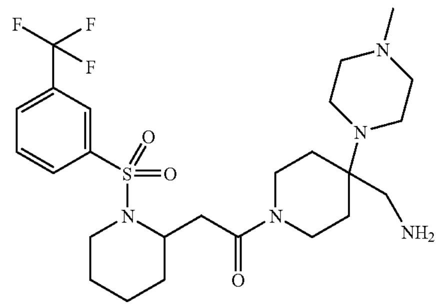 [SMILES: CN1CCN(C2(CN)CCN(C(=O)CC3CCCCN3S(=O)(=O)c3cccc(C(F)(F)F)c3)CC2)CC1] | 1-(4-(Aminomethyl)-4-(4-methylpiperazin-1-yl)piperidin-1-yl)-2-(1-(3-(trifluoromethyl)phenylsulfonyl)-piperidin-2-yl)ethanone |
| AM11 | 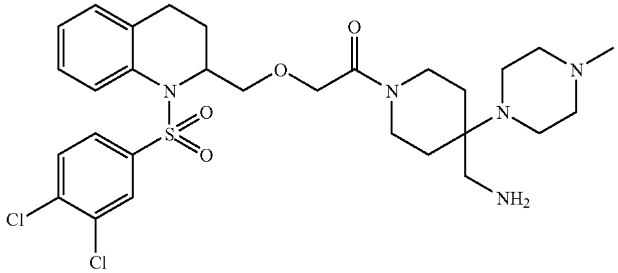 [SMILES: CN1CCN(C2(CN)CCN(C(=O)COCC3CCc4ccccc4N3S(=O)(=O)c3ccc(Cl)c(Cl)c3)CC2)CC1] | 1-(4-(Aminomethyl)-4-(4-methylpiperazin-1-yl)piperidin-1-yl)-2-((1-(3,4-dichlorophenylsulfonyl)-1,2,3,4-tetrahydroquinolin-2-yl)methoxy)ethanone |
| AM12 | 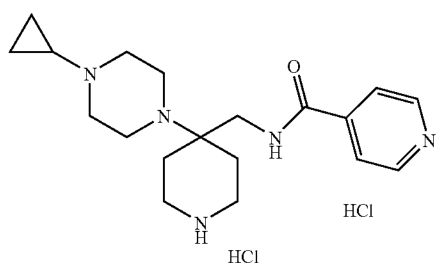 [SMILES: O=C(NCC1(N2CCN(C3CC3)CC2)CCNCC1)c1ccncc1 ; Cl ; Cl] | N-((4-(4-Cyclopropylpiperazin-1-yl)piperidin-4-yl)methyl)isonicotinamide dihydrochloride |
| AM13 | 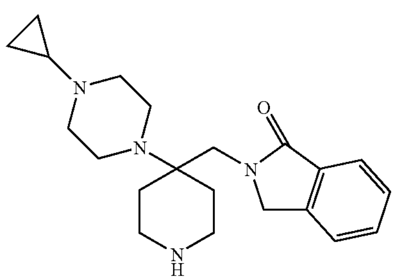 [SMILES: O=C1c2ccccc2CN1CC1(N2CCN(C3CC3)CC2)CCNCC1] | 2-((4-(4-Cyclopropylpiperazin-1-yl)piperidin-4-yl)methyl)isoindolin-1-one |
| AM14 | 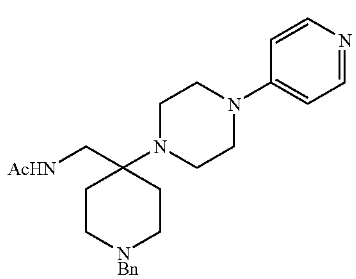 [SMILES: CC(=O)NCC1(N2CCN(c3ccncc3)CC2)CCN(Cc2ccccc2)CC1] | N-((1-Benzyl-4-(4-(pyridin-4-yl)piperazin-1-yl)piperidin-4-yl)methyl)acetamide |

-continued

| Amine unit | Structure | Name |
|---|---|---|
| AM-15 | 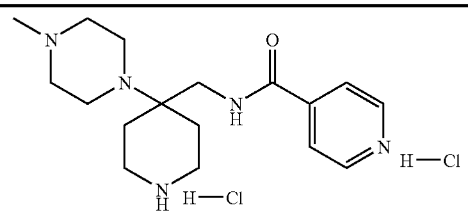 | N-((4-(4-Methylpiperazin-1-yl)piperidin-4-yl)methyl)isonicotin-amide dihydrochloride (A-40) |

Method A

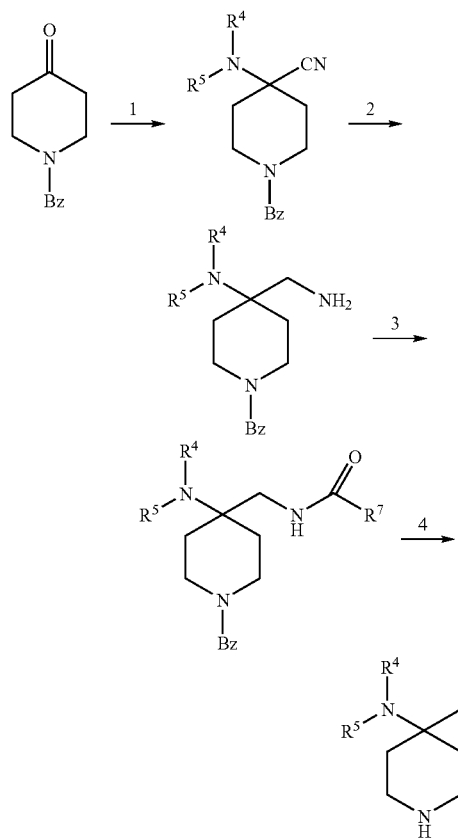

Stage 1. Water (1.2 ml), the corresponding amine (52.9 mmol), acetic acid (52.9 mmol) and potassium cyanide (58.2 mmol) were added successively to a solution of N-benzylpiperidone (52.9 mmol) in methanol (20 ml). The reaction mixture was stirred at room temperature for 1 h, a white solid forming. $NH_4OH$ solution (35%, 300 ml) and ice (100 g) were then added to the reaction solution. The resulting solid was filtered out, washed several times with water and dried.

Stage 2. A solution of $H_2SO_4$ (1 eq.) in THF (1 ml/mmol) was added dropwise to a suspension, cooled to 0° C., of LAH (3 eq.) in THF (2 ml/mmol) (very exothermic reaction!). The suspension was stirred at 25° C. for 1 h and then cooled to 0° C. The nitrile (1 eq.) in THF (2 ml/mol) was added dropwise to this suspension and the mixture was then heated at 50° C. for 12 h (TLC control). An aqueous $Na_2SO_4$ solution was added to the reaction mixture and the mixture was filtered over Celite. The aqueous phase was extracted with ethyl acetate, the organic phase was then dried over $Na_2SO_4$ and filtered and the solvent was removed in vacuo. The crude product was employed in the next stage without further purification.

Stage 3. Triethylamine (2.5 eq.) and the corresponding acid chloride (1.1 eq.) were added to a solution, cooled to 0° C., of the amine (1 eq.) in MC and the mixture was stirred at this temperature for 12 h. The reaction solution was then warmed to 25° C. and stirred at this temperature for 1 h (TLC control). After reaction of the amine was complete, hydrolysis was carried out with ice, the mixture was diluted further with MC and the organic phase was washed with water and sat. NaCl solution. The mixture was then dried over $Na_2SO_4$ and filtered and the solvent was removed in vacuo. The crude product was purified by column chromatography (neutral $Al_2O_3$), MC/methanol: 9:1).

Stage 4. $Pd(OH)_2$ (10%, 50 wt. %) was added to a solution of the benzylated compound in methanol (3 ml/mmol) and hydrogenolysis was carried out under atmospheric pressure for 16 h (LCMS control). When the reaction was concluded, the reaction mixture was filtered over Celite and the residue was rinsed a few times with methanol. The combined organic phases were concentrated under reduced pressure. The crude product was used further without further purification.

The amine units AM1-AM5 listed in the following were prepared by Method A.

| No. | $NR^4R^5$ | $R^7$ | Name |
|---|---|---|---|
| AM1 | N-Methylpiperazinyl | Picolinoyl | N-((4-(4-Methylpiperazin-1-yl)piperidin-4-yl)methyl)picolinamide |
| AM2 | 1-(Pyridin-4-yl)-piperazinyl | Acetyl | N-((4-(4-(Pyridin-4-yl)piperazin-1-yl)piperidin-4-yl)methyl)acetamide |
| AM3 | N-Methylpiperazinyl | Acetyl | N-((4-(4-Methylpiperazin-1-yl)piperidin-4-yl)methyl)acetamide |
| AM4 | N-Methylpiperazinyl | Benzoyl | N-((4-(4-Methylpiperazin-1-yl)piperidin-4-yl)methyl)benzamide |
| AM5 | N-Methylpiperazinyl | Phenacetyl | N-((4-(4-Methylpiperazin-1-yl)piperidin-4-yl)methyl)-2-phenylacetamide |

Method B

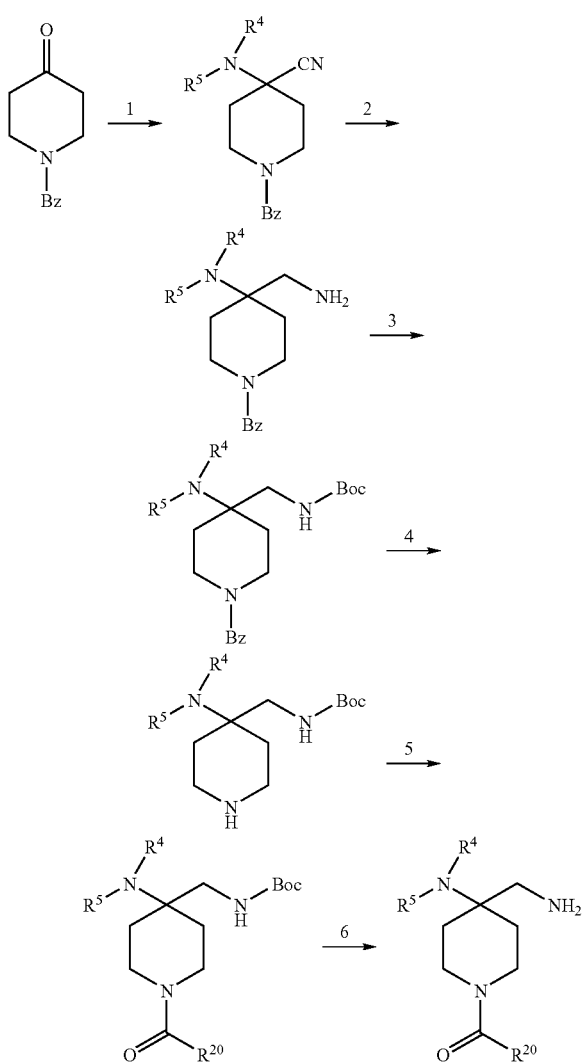

In Method B, stage 1. and stage 2. were carried out analogously to Method A.

Stage 3. The benzyl-protected amine (1 eq.) was dissolved in MC (5 ml/mmol), DIPEA (1.5 eq.) and $Boc_2O$ (1.2 eq.) were added at 25° C. and the mixture was stirred at this temperature for 16 h (TLC control). The mixture was diluted with MC and then washed first with water and then with NaCl solution. The organic phase was dried over $Na_2SO_4$ and concentrated. The crude product was purified by column chromatography (silica gel, MC/methanol: 97:3).

Stage 4. $Pd(OH)_2$ (10%, 50 wt. %) was added to a solution of the benzylated compound in methanol (3 ml/mmol) and hydrogenation was carried out under atmospheric pressure for 16 h (LCMS control). When the reaction was concluded, the reaction mixture was filtered over Celite and the residue was rinsed a few times with methanol. The combined organic phases were concentrated under reduced pressure. The crude product was employed further without further purification.

Stage 5. EDCI (1.5 eq.), HOBt (1 eq.) and DIPEA (2 eq.) were added to a solution of the corresponding acid unit AC1-AC6 [=$R^{20}$—COOH] (1 eq.) in MC (5 ml/mmol). The reaction mixture was stirred at 25° C. for 15 min. The corresponding Boc-protected amine unit, dissolved in DMF (5 ml/mmol), was added to this solution and the mixture was stirred at 25° C. for 16 h. The mixture was then diluted with MC and washed successively with $NH_4Cl$ solution, $NaHCO_3$ solution and NaCl solution. The organic phase was concentrated under reduced pressure. The crude product was purified by column chromatography (silica gel, MC/methanol: 95:5).

Stage 6. The Boc-protected amines from stage 5. were dissolved in TFA (20% in MC, 5 ml/mmol) at 0° C. and the solution was then warmed to 25° C. The reaction mixture was stirred at this temperature for 3 h (TLC control). When the reaction was concluded, the solvent was removed completely and the crude product was used for the further reactions without further purification.

The amine units AM6 to AM11 listed in the following were prepared by Method B.

| No. | $NR^4R^5$ | $R^{20}$ | Name |
|---|---|---|---|
| AM6 | N-Methyl-piperazinyl | | N-(2-(2-(4-(Aminomethyl)-4-(4-methylpiperazin-1-yl)piperidin-1-yl)-2-oxoethoxy)ethyl)-4-methoxy-N,2,6-trimethylbenzenesulfonamide |

-continued

| No. | NR⁴R⁵ | R²⁰ | Name |
|---|---|---|---|
| AM7 | N-Methyl-piperazinyl | 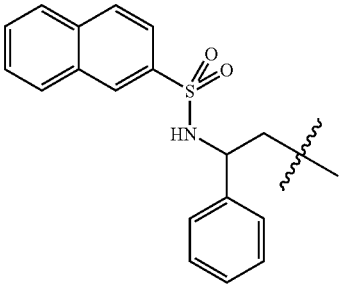 [SMILES: *CC(NS(=O)(=O)c1ccc2ccccc2c1)c1ccccc1] | N-(3-(4-(Aminomethyl)-4-(4-methylpiperazin-1-yl)piperidin-1-yl)-3-oxo-1-phenylpropyl)naphthalene-2-sulfonamide |
| AM8 | N-Methyl-piperazinyl | 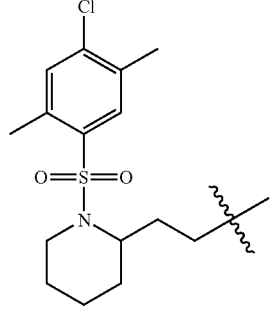 [SMILES: *CCC1CCCCN1S(=O)(=O)c1cc(C)c(Cl)cc1C] | 1-(4-(Aminomethyl)-4-(4-methyl-piperazin-1-yl)piperidin-1-yl)-3-(1-(4-chloro-2,5-dimethylphenylsulfonyl)-piperidin-2-yl)propan-1-one |
| AM9 | N-Methyl-piperazinyl | 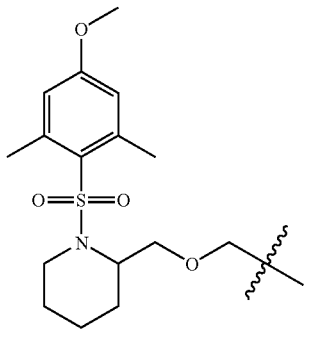 [SMILES: *COCC1CCCCN1S(=O)(=O)c1c(C)cc(OC)cc1C] | 1-(4-(Aminomethyl)-4-(4-methyl-piperazin-1-yl)piperidin-1-yl)-2-((1-(4-methoxy-2,6-dimethylphenylsulfonyl)-piperidin-2-yl)methoxy)ethanone |
| AM10 | N-Methyl-piperazinyl | 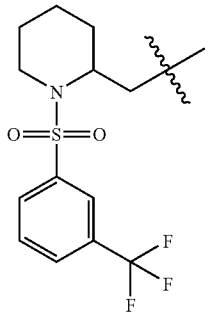 [SMILES: *CC1CCCCN1S(=O)(=O)c1cccc(C(F)(F)F)c1] | 1-(4-(Aminomethyl)-4-(4-methylpiperazin-1-yl)piperidin-1-yl)-2-(1-(3-(trifluoromethyl)phenylsulfonyl)-piperidin-2-yl)ethanone |
| AM11 | N-Methyl-piperazinyl | 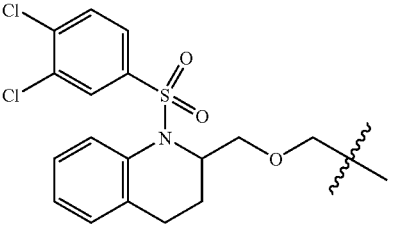 [SMILES: *COCC1CCc2ccccc2N1S(=O)(=O)c1ccc(Cl)c(Cl)c1] | 1-(4-(Aminomethyl)-4-(4-methylpiper-azin-1-yl)piperidin-1-yl)-2-((1-(3,4-dichloro-phenylsulfonyl)-1,2,3,4-tetra-hydroquinolin-2-yl)methoxy)ethanone |

Amine AM12: N-((4-(4-Cyclopropylpiperazin-1-yl)piperidin-4-yl)methyl)-isonicotinamide dihydrochloride

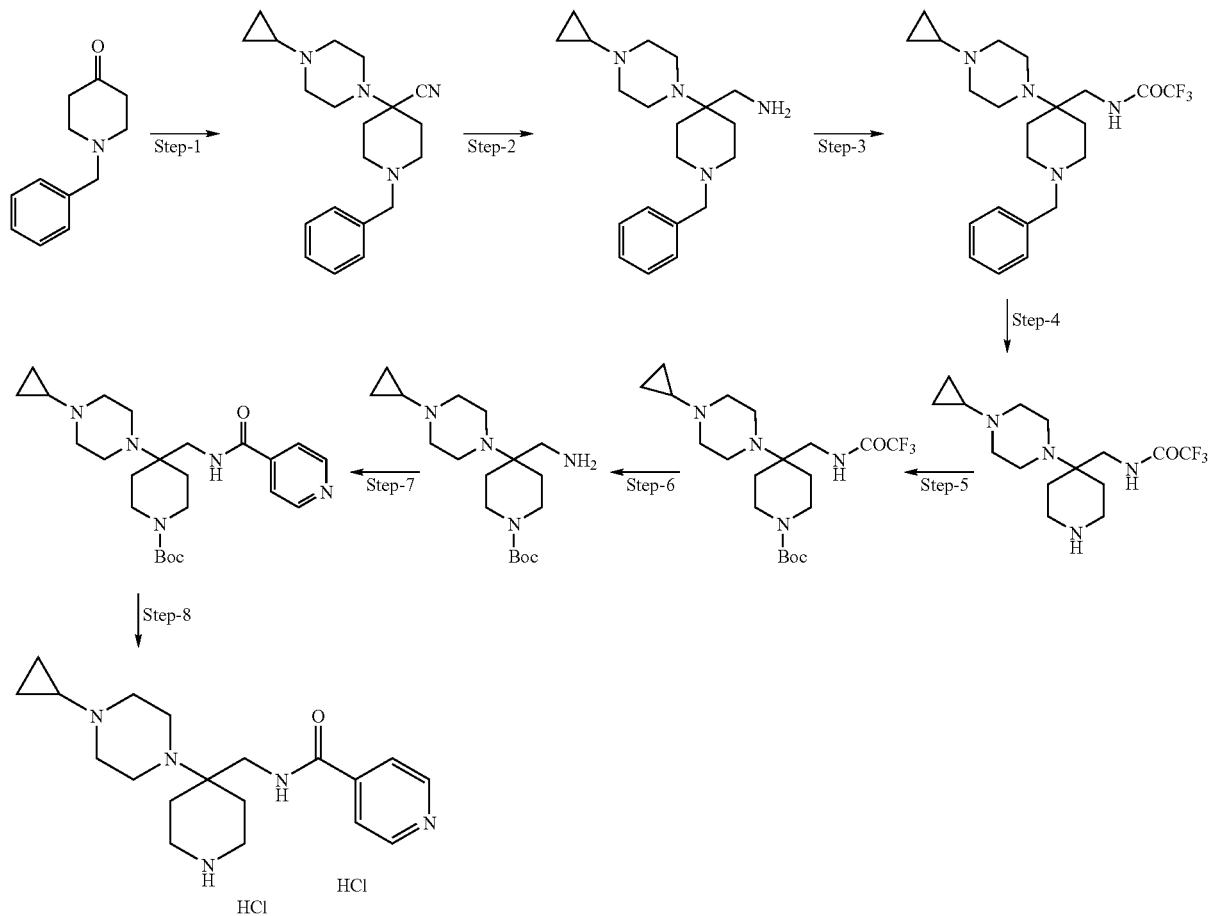

Step-1: 1-Benzyl-4-(4-cyclopropylpiperazin-1-yl)piperidine-4-carbonitrile

To a solution of 1-benzylpiperidin-4-one (26.42 mmol, 1.0 equiv.) and acetic acid (26.42 mmol, 1.0 equiv.) in methanol (10 ml) were added water (600 ml), N-cyclopropyl piperazine (29.06 mmol, 1.1 equiv.), and potassium cyanide (26.42 mmol, 1.0 equiv.). The resulting reaction mixture was stirred at room temperature for 1 h by which time a solid had separated. The solid was collected by filtration, washed with water and dried to obtain the desired product which was used in the next step without further purification. Yield: 53%.

Step-2: (1-Benzyl-4-(4-cyclopropylpiperazin-1-yl)piperidin-4-yl)methanamine

To a cooled (0° C.) suspension of LAH (9.24 mmol, 3.0 equiv.) in THF (2 ml/mmol) was added dropwise conc. $H_2SO_4$ (4.62 mmol, 1.5 equiv.) in THF (1 ml/mmol) and the resulting suspension was stirred at room temperature for 1.5 h. A solution of 1-benzyl-4-(4-cyclopropylpiperazin-1-yl)piperidine-4-carbonitrile (3.08 mmol, 1.0 equiv.) in THF (2 ml/mmol) was added dropwise to the reaction mixture and it was heated to 50° C. for 12 h. The mixture was quenched with sodium sulfate solution, filtered through celite and washed with ethyl acetate. The organic layer was dried over sodium sulfate and the solvent was evaporated under reduced pressure to yield the desired product. Yield: 90%

Step-3: N-((1-Benzyl-4-(4-cyclopropylpiperazin-1-yl)piperidin-4-yl)methyl)-2,2,2-trifluoroacetamide To a solution of (1-benzyl-4-(4-cyclopropylpiperazin-1-yl)piperidin-4-yl)-methanamine (11.29 mmol, 1.0 equiv.) and triethylamine (5.0 equiv.) in dichloromethane (56 ml) was added trifluoroacetic anhydride at 0° C. and the resulting reaction mixture was stirred at room temperature for 2 h. The mixture was diluted with dichloromethane, successively washed with water and brine, dried over sodium sulfate and the solvent evaporated under reduced pressure to yield the crude product which was purified by silica gel column chromatography. Yield: 50%.

Step-4: N-((4-(4-Cyclopropylpiperazin-1-yl)piperidin-4-yl)methyl)-2,2,2-trifluoroacetamide Through a solution of N-((1-benzyl-4-(4-cyclopropylpiperazin-1-yl)-piperidin-4-yl)methyl)-2,2,2-trifluoroacetamide (5.4 mmol) in methanol (30 ml) was passed argon gas for 10 min. Then acetic acid (855 µl) and Pd(OH)$_2$ (40% by weight) were added to the reaction mixture and it was stirred at room temperature for 16 h under an atmosphere of H$_2$ by using a hydrogen balloon. The reaction mixture was filtered through celite and the filtrate was concentrated to dryness to yield the desired product which was used in the next step without further purification. Yield: 90%.

Step-5: tert-Butyl 4-(4-cyclopropylpiperazin-1-yl)-4-((2,2,2-trifluoro-acetamido)methyl)piperidine-1-carboxylate To a solution of N-((4-(4-cyclopropylpiperazin-1-yl)piperidin-4-yl)methyl)-2,2,2-trifluoroacetamide (6.88 mmol, 1.0 equiv.) and DIPEA (1.5 equiv.) in dichloromethane (35 ml) was added Boc anhydride (8.26 mmol, 1.2 equiv.) and the reaction mixture was stirred at room temperature for 3 h. The mixture was diluted with dichloromethane, successively washed with water and brine, dried over sodium sulfate and the solvent evaporated under reduced pressure to obtain the crude product which was purified by silica gel column chromatography. Yield: 50%.

Step-6: tert-Butyl 4-(aminomethyl)-4-(4-cyclopropylpiperazin-1-yl)-piperidine-1-carboxylate To a solution of tert-butyl 4-(4-cyclopropylpiperazin-1-yl)-4-((2,2,2-trifluoroacetamido)methyl)piperidine-1-carboxylate (3.22 mmol) in methanol (8 ml) was added 1 N NaOH solution (13 ml) and the reaction mixture was stirred at room temperature for 2 h. After completion the reaction mixture was extracted with ethyl acetate (3×). The combined organic layers were washed with brine, dried over sodium sulfate and the solvent was evaporated under reduced pressure to obtain the desired product. Yield: 90%.

Step-7: tert-Butyl 4-(4-cyclopropylpiperazin-1-yl)-4-(isonicotinamido-methyl)piperidine-1-carboxylate To a solution of tert-butyl 4-(aminomethyl)-4-(4-cyclopropylpiperazin-1-yl)piperidine-1-carboxylate (0.769 mmol, 1.0 equiv.) and triethylamine (2.5 equiv.) in dichloromethane (7 ml) was added isonicotinyl chloride (0.769 mmol, 1.0 equiv.) and the reaction mixture was stirred at room temperature for 2 h. The mixture was diluted with dichloromethane, successively washed with water and brine, dried over sodium sulfate and the solvent evaporated under reduced pressure to obtain the crude product which was purified by silica gel column chromatography. Yield: 70%.

Step-8: N-((4-(4-Cyclopropylpiperazin-1-yl)piperidin-4-yl)methyl)isonicotinamide dihydrochloride (AM12)

To a cooled (0° C.) solution of tert-butyl 4-(4-cyclopropylpiperazin-1-yl)-4-(isonicotinamidomethyl)piperidine-1-carboxylate (0.541 mmol) in dioxane (1 ml/mmol) was added saturated dioxane-HCl solution (3.3 ml) and the reaction mixture was stirred at room temperature for 3 h. The solvent was evaporated and the residue was azeotroped with dioxane (3×). The crude product was used in the next step.

Amine AM13: 2-((4-(4-Cyclopropylpiperazin-1-yl)piperidin-4-yl)methyl)-isoindolin-1-one

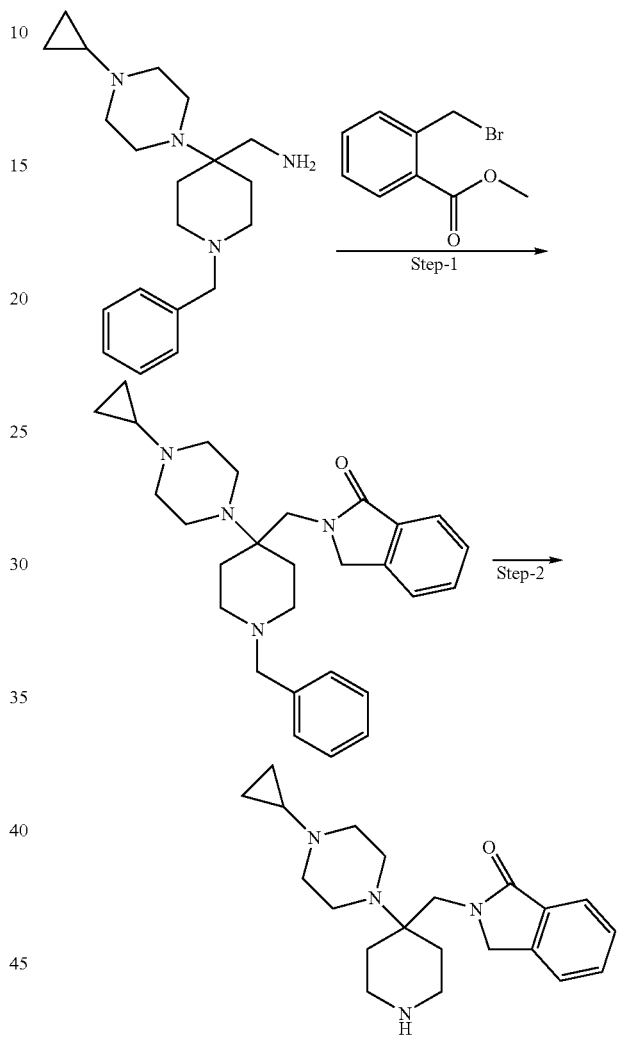

Step-1: 2-((1-Benzyl-4-(4-cyclopropylpiperazin-1-yl)piperidin-4-yl)methyl)-isoindolin-1-one To a solution of (1-benzyl-4-(4-cyclopropylpiperazin-1-yl)piperidin-4-yl)methanamine (see above: synthesis of amine AM12) (1.22 mmol, 1.0 equiv.) and methyl 2-(bromomethyl)benzoate (1.22 mmol, 1.0 equiv.) in benzene (3 ml/mmol) was added triethylamine (2.44 mmol, 2.0 equiv.) and the resulting reaction mixture was refluxed for 25 h. The mixture was cooled to room temperature and the solvent was evaporated under reduced pressure. The residue was dissolved in ethyl acetate and the organic layer was successively washed with water and brine. The organic layer was dried over sodium sulfate and the solvent was evaporated under reduced pressure to give the crude product which was purified by silica gel column chromatography. Yield: 51%.

Step-2: 2-((4-(4-Cyclopropylpiperazin-1-yl)piperidin-4-yl)methyl)isoindolin-1-one (AM13)

Through a solution of 2-((1-Benzyl-4-(4-cyclopropylpiperazin-1-yl)-piperidin-4-yl)methyl)isoindolin-1-one (0.63 mmol) in ethanol (10 ml) was passed argon gas for 10 min. Then acetic acid (200 μl) and Pd(OH)$_2$ (20% by weight) were added to the reaction mixture. The mixture was stirred at room temperature for 16 h under an atmosphere of H$_2$ by using a hydrogen balloon. The reaction mixture was filtered through celite and the filtrate was concentrated to dryness to give the desired product. Yield: 60%.

Amine AM14: N-((1-Benzyl-4-(4-(pyridin-4-yl)piperazin-1-yl)piperidin-4-yl)-methyl)acetamide

Step 2: 1-(Pyridin-4-yl)piperazine tert-Butyl 4-(pyridin-4-yl)piperazine-1-carboxylate was produced using standard de-Boc conditions (see above: 13 equiv. TFA in dichlorormethane) which was made TFA free upon work-up by stirring with basic amberlyst resin in methanol.

Step 3: 1-Benzyl-4-(4-(pyridin-4-yl)piperazin-1-yl)piperidine-4-carbonitrile A solution containing 1-(pyridin-4-yl)piperazine (58.34 mmol, 1 equiv.), N-benzyl-piperidinone (1 equiv.), KCN (1.1 equiv.), AcOH (3.3 ml) and water (1.3 ml) in methanol was stirred at room temperature for 16 h. The reaction mixture was quenched with NH$_4$OH solution (400 ml) and filtered. The

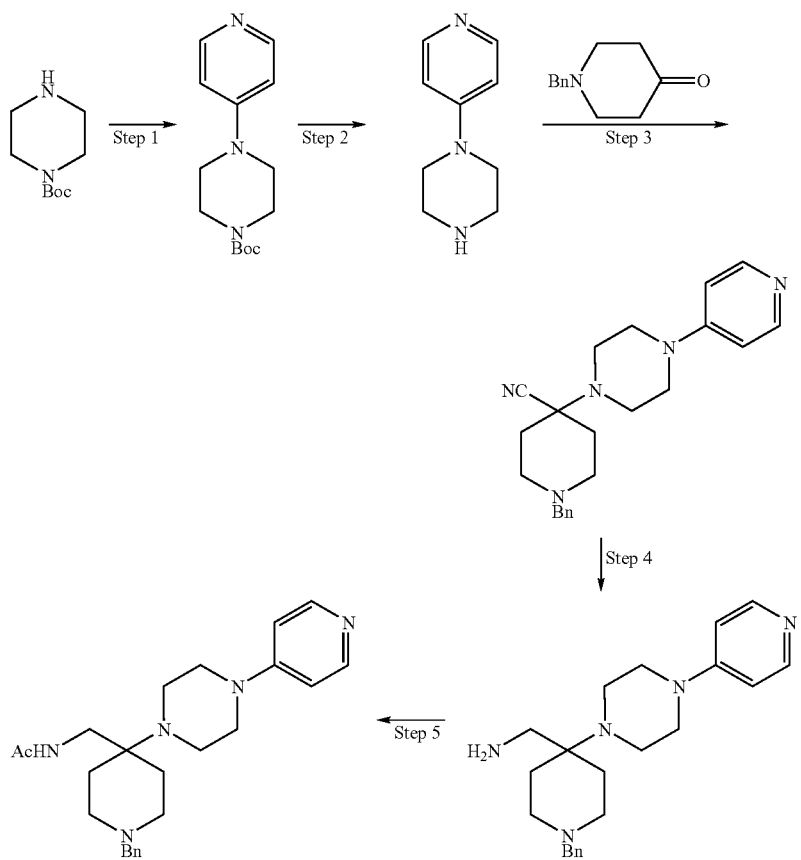

Step 1: tert-Butyl 4-(pyridin-4-yl)piperazine-1-carboxylate

To a degassed solution of 4-bromopyridine (1 equiv.), tert-butyl piperazine-1-carboxylate (16 mmol, 1.2 equiv.) and NaOtBu (3.4 equiv.) in toluene were added Pd(OAc)$_2$ (2 mol %) and BINAP (1 mol %) and the resulting solution was refluxed for 3 h. The reaction mixture was cooled, diluted with ethyl acetate and given water and brine washes respectively. The organic layer was dried over sodium sulfate, the solvent removed in vacuo and the crude product purified by column chromatography (silica). Yield: 47%.

solid precipitate was thoroughly washed with water, dried under vacuum and taken through to the next reaction without further purification. Yield: 47%.

Step 4: (1-Benzyl-4-(4-(pyridin-4-yl)piperazin-1-yl)piperidin-4-yl)methanamine H$_2$SO$_4$ (1.5 equiv.) was added to a suspension of LAH (3 equiv.) in THF (32 ml) at 0° C. and the mixture was stirred at room temperature for 0.5 h. A solution of 1-benzyl-4-(4-(pyridin-4-yl)piperazin-1-yl)piperidine-4-carbonitrile (5.54 mmol, 1 equiv.) in THF was added under cooled conditions and the resulting reaction mixture was heated to 50° C. for 16 h. The reaction was quenched with THF/H$_2$O solution, filtered and the solid residue washed with excess ethyl acetate.

The organic layer was given a brine wash, dried over sodium sulfate and the solvent was removed under reduced pressure. The resulting crude product was used for the next step without further purification. Yield: 85%.

Step 5: N-((1-Benzyl-4-(4-(pyridin-4-yl)piperazin-1-yl)piperidin-4-yl)methyl)acetamide (AM14)

Triethylamine (2.5 equiv.) followed by acetyl chloride (1.2 equiv.) were added under cooled conditions to a solution of (1-benzyl-4-(4-(pyridin-4-yl)piperazin-1-yl)piperidin-4-yl)methanamine (4.67 mmol, 1 equiv.) in dichloromethane. The resulting solution was warmed to room temperature and stirred for 3 h. The mixture was diluted with dichloromethane and given water and brine washes respectively. The organic layer was dried over sodium sulfate, filtered and the solvent removed. The crude product was purified by column chromatography (silica). Yield: 52%

Synthesis of amine building block AM-15: 2-((1-(2 N-((4-(4-Methylpiperazin-1-yl)piperidin-4-yl)methyl)isonicotinamide dihydrochloride (AM-15)

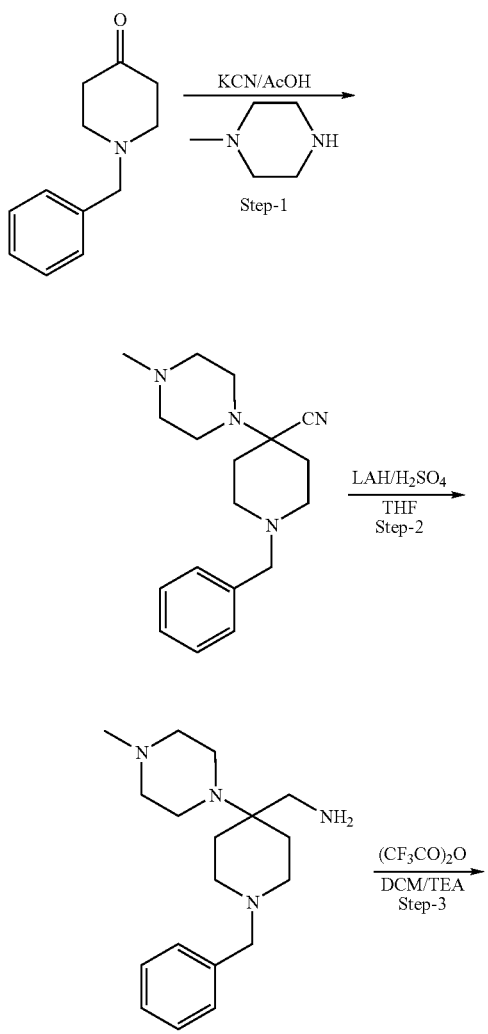

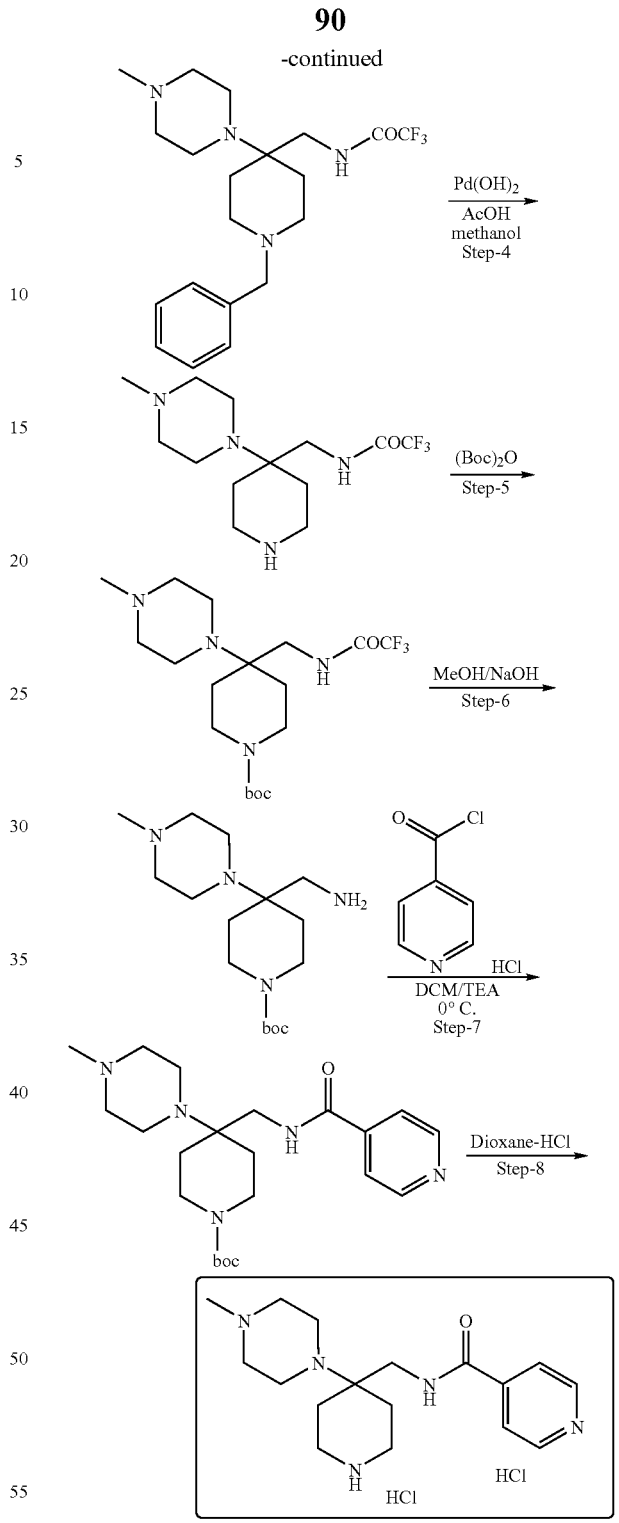

Procedure for Step-1:

To a methanolic solution (20 ml) of N-benzyl piperidone (52.9 mmol) was added water (1.2 ml), N-methylpiperazine (1 eqv), acetic acid (1 eqv) and potassium cyanide (1.1 eqv). The resulting reaction mixture was stirred at 25° C. for 1 hr by which time solid was separated. It was then treated with 35% ammonium hydroxide (300 ml) and ice (100 g). Solid was filtered, washed several times with water and dried. Yield: 45%.

Procedure for Step-2:

To a cold (0° C.) suspension of LAH (3 eqv) in THF (2 ml/mmol) under argon atmosphere was added dropwise a solution of conc. $H_2SO_4$ (1.5 eqv) in THF (1 ml/mmol) (very exothermic). The suspension was stirred for 90 minutes at 25° C. and then cooled to 0° C. To this cold reaction mixture, cyano compound (1 eqv) in THF (2 ml/mmol) was added dropwise and after complete addition it was heated at 50° C. for 12 hrs (monitored by TLC). Reaction was carefully quenched with a saturated aqueous solution of sodium sulfate and filtered over a celite bed. Residue was washed with ethyl acetate, organic layer was dried over sodium sulfate and evaporated under reduced pressure to get the crude amine which was used directly in the next step without any further purification. Yield 79%

Procedure for Step-3:

To a dichloromethane (5 ml/mmol) solution of the amine obtained from step-2 (74.5 mmol) was added TEA (5 eqv) and trifluoro acetic anhydride (2 eqv) at 0° C. and the resulting reaction mixture was stirred at 25° C. for 2 hrs (monitored by TLC). Reaction was diluted with dichloromethane, washed successively with water and brine and finally dried over sodium sulfate. Evaporation of organic layer under reduced pressure gave the crude product which was purified by column chromatography (10% methanol in dichloromethane). Yield: 64%

Procedure for Step-4:

A solution of the benzylated compound obtained from step-3 (19 g) in methanol (285 ml) was deoxygenated with argon. To it was added 10% $Pd(OH)_2$ (9.5 g), AcOH (7.6 ml) and the resulting reaction mixture was hydrogenated under atmospheric pressure for 16 hrs (monitored by TLC and LCMS). It was filtered through celite bed, the residue was washed with methanol and the combined organic layer was evaporated to dryness to obtain the crude product which was used directly in the next step without any further purification. Yield 14.8 g (quantitative).

Procedure for Step-5:

To a dichloromethane solution (240 ml) of the amine (14.8 g, 48 mmol) obtained from step-4 was added DIPEA (1.5 eqv), boc-anhydride (1.2 eqv) at 0° C. and the resulting reaction mixture was stirred at ambient temperature for 3 hrs. It was diluted with dichloromethane, organic layer was washed successively with water and brine and finally dried over sodium sulfate. Evaporation of the organic layer under reduced pressure gave the crude product which was purified by column chromatography (10% methanol in dichloromethane). Yield: 12.5 g (63%).

Procedure for Step-6:

To a methanol solution (80 ml) of the boc-protected compound obtained from step-5 was added 1(N) NaOH (120 ml) at 0° C. and the resulting reaction mixture was stirred at 25° C. for 2 hrs (monitored by TLC). Reaction mixture was diluted with ethyl acetate, aqueous layer was extracted several times with ethyl acetate and the combined organic layer was washed with brine. After drying over sodium sulfate, organic layer was evaporated under reduced pressure to get the crude product which was used directly in next step without any further purification. Yield: 7.7 g (83%)

Procedure for Step-7:

To a cold (0° C.) DCM solution of the amino compound (1 eqv) obtained from step-6 was added triethyl amine (2.5 eqv) and isonicotinoyl chloride hydrochloride (1 eqv) and the reaction was stirred at 25° C. for 2 hrs (monitored by TLC). Reaction was quenched with crushed ice, diluted with DCM and organic layer was washed successively with water and brine. After drying over sodium sulfate, organic layer was evaporated under reduced pressure to get the crude product which was purified by column chromatography (neutral alumina, 1:9 methanol in dichloromethane). Yield: 70%

Procedure for Step-8:

To a dioxane solution (2 ml/mmol) of the boc-protected compound obtained from step-7 was added dioxane containing HCl gas (2 M, 6 ml/mmol) at 0° C. and the resulting reaction mixture was stirred at 25° C. for 3 hrs (monitored by TLC). Solid was collected by filtration, washed with ether under inert atmosphere and finally dried under vacuum to get the product. Yield: 80%.

Parallel Synthesis Methods

Parallel Synthesis Method A

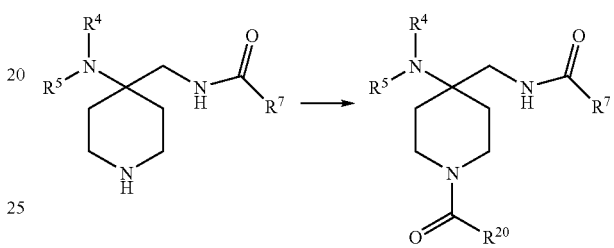

EDCI (1.5 eq.), HOBt (1 eq.) and DIPEA (2 eq.) were added to a solution of the corresponding acid unit "AC" [=$R^{20}$—COOH] (1 eq.) in MC (5 ml/mmol). The reaction mixture was stirred at 25° C. for 15 min. The corresponding amine unit, dissolved in DMF (5 ml/mmol), was added to this solution and the mixture was stirred at 25° C. for 16 h. The mixture was then diluted with MC and washed successively with $NH_4Cl$ solution, $NaHCO_3$ solution and NaCl solution. The organic phase was concentrated under reduced pressure. The crude product was purified in a parallel purification system from Biotage.

Parallel Synthesis Method B

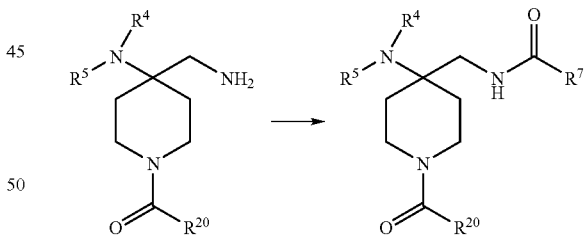

Triethylamine (4.5 eq.) and the corresponding acid chloride (1.1 eq.) were added to a solution, cooled to 0° C., of the Boc-protected amine (1 eq.) in MC (5 ml/mmol) and the mixture was stirred at this temperature for 30 min. The reaction solution was then warmed to 25° C. and stirred at this temperature for 1 h (TLC control). After reaction of the amine was complete, hydrolysis was carried out with ice, the mixture was diluted further with MC and the organic phase was washed with water and saturated NaCl solution. The mixture was then dried over $Na_2SO_4$ and filtered and the solvent was removed in vacuo. The crude product was purified in a parallel purification system from Biotage.

93

Parallel Synthesis Method C

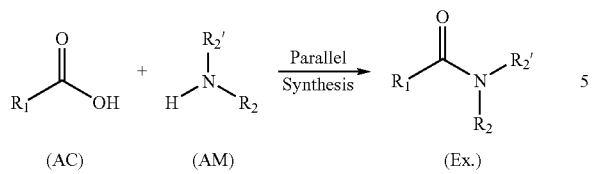

(AC)    (AM)    (Ex.)

Similarly to Method A, acid building blocks (AC) were converted with amines (AM) to the amide Example Compounds (Ex.) using parallel synthesis. The correlation between product, reagent, building block and method can be taken from the table below, listing all Example Compounds prepared by the above described Methods A, B and C.

To a solution of acid S (100 µmol) in 1 mL dichlormethane a solution of 1,1'-carbonyldiimidazol (150 µmol) in 1 mL dichlormethane was added and the reaction mixture was stirred at room temperature for 1.5 h. Afterwards a solution of amine A (150 µmol) and Hünigs base (500 µmol) in 1 mL dichlormethane was added. The mixture was stirred for 18 h at room temperature. The solvent was evaporated under reduced pressure in a vacuum centrifuge (brand: GeneVac). The final purification resulted from HPLC-MS[2]. The final analytics resulted from LC-MS[1]. The crude products from the parallel synthesis according to Method C were analyzed by HPLC_MS and subsequently purified via reverse phase HPLC-MS. The identification of the products was demonstrated by analytical HPLC-MS measurements:

Equipment and Methods for HPLC-MS Analytics:

Parallel Synthesis Method: HPLC: Waters Alliance 2795 with PDA Waters 2996; MS: ZQ 2000 MassLynx Single Quadrupol MS Detector; Column: Atlantis dC18 30×2.1 mm, 3 µm; Col. temp.: 40° C., Eluent A: purified water+0.1% formic acid; Eluent B: methanol (gradient grade)+0.1% formic acid; Gradient: 0% B to 100% B in 2.3 min, 100% B for 0.4 min, 100% B to 0% B in 0.01 min, 0% B for 0.8 min; Flow: 1.0 mL/min; Ionisation: ES+, 25V; make up: 100 µL/min 70% methanol+0.2% formic acid; UV: 200-400 nm.

Equipment and Methods for HPLC-MS Purification:

Prep Pump Waters 2525; Make Up Pump: Waters 515; Auxilary Detector: Waters DAD 2487; MS Detector: Waters Micromass ZQ; Injector/Fraction Collector: Waters Sample Manager 2767; Gradient: Initial: 60% Water 40% Methanol→12-14.5 min: 0% Water 100% Methanol→14.5-15 min: 60% Water 40% Methanol; Flow: 35 ml/min Column: Macherey-Nagel, C18 Gravity, 100×21 mm, 5µ.

Synthesis of Individual Compounds

Example 1

N-((1-(2-(2-(4-Methoxy-N,2,6-trimethylphenylsulfonamido)-ethoxy)acetyl)-4-(4-methylpiperazin-1-yl)piperidin-4-yl)methyl)isonicotin-amide

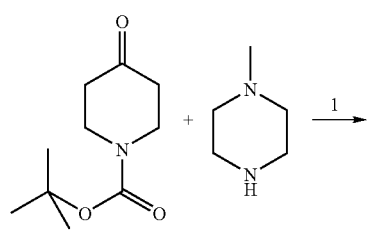

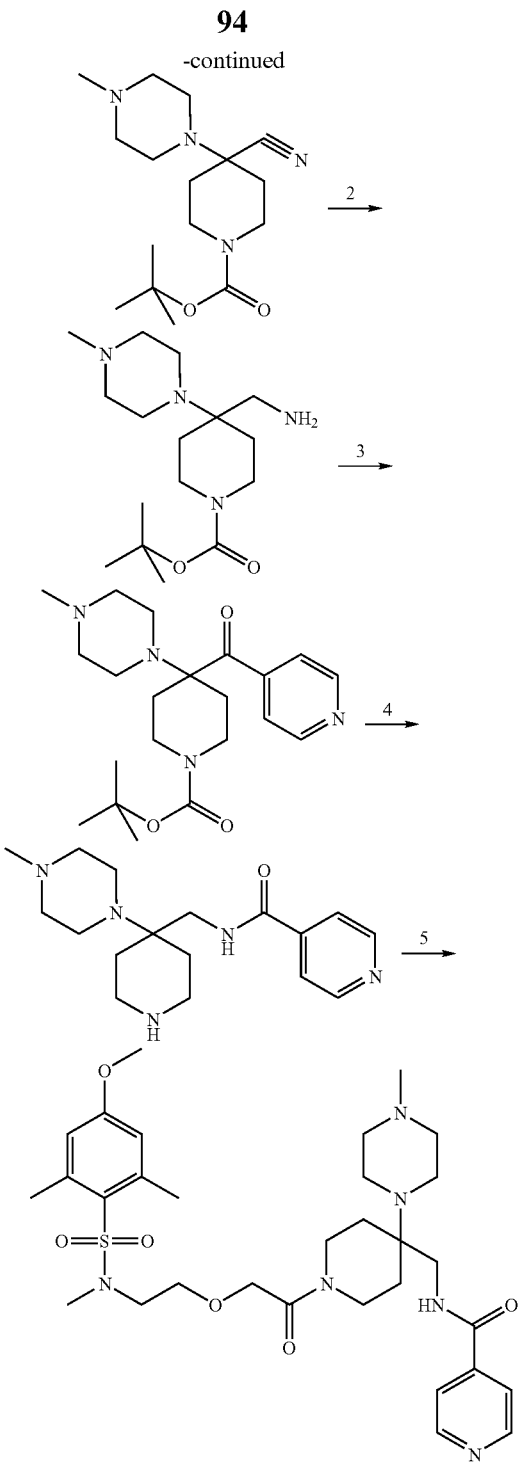

Stage 1. A mixture of N-Boc-piperidone (10.0 g, 50.2 mmol), 1-methylpiperazine (5.57 ml, 50.2 mmol), water (1.18 ml, 65.2 mmol) and acetic acid (3.18 ml, 55.2 mmol) in methanol (20 ml) was stirred at RT under a nitrogen atmosphere. KCN (3.44 g, 52.8 mmol) was added and the reaction mixture was stirred at RT. After 30 min, a solid precipitated out. Aqueous NH$_4$OH solution (35%, 300 ml) and ice (100 g) were added to the reaction mixture. The solid was filtered out, dried and employed further without further purification.

Stage 2. A solution of LAH (1.0 M in diethyl ether, 34.6 ml, 34.6 mmol) was cooled to 0° C. and the product from stage 1., dissolved in diethyl ether (150 ml), was added dropwise. The mixture was then stirred at 0° C. for 2 h. Na$_2$SO$_4$.10H$_2$O was then added at 0° C., until no further evolution of gas was to be detected. The reaction mixture was filtered and washing was carried out with MC. The solvent was removed and the crude product was employed further without further purification.

Stage 3. Triethylamine (4.2 ml, 29.7 mmol) and isonicotinoyl chloride hydrochloride (1.20 g, 6.74 mmol) were added to a solution of the crude product from stage 2. (max. 9.89 mmol) in MC (125 ml) at RT. The reaction mixture was stirred at RT for 3 h and then concentrated to dryness. The crude product was purified by column chromatography (silica gel, MC, 7 M $NH_3$ in methanol, 95:5).

Stage 4. HCl (4 M in dioxane, 2.35 ml, 9.4 mmol) was added to a solution of the product from stage 3. (490 mg, 1.17 mmol) in dioxane (10 ml) and the mixture was stirred at RT for 3 h. The solvent was removed and the crude product was employed further without further purification.

Stage 5. A mixture of the Boc-deprotected product (max. 1.17 mmol), the acid AC1 (388 mg, 1.17 mmol), DIPEA (957 µl, 5.85 mmol) and HOAt (24 mg, 0.18 mmol) in MC (25 ml) was cooled to 0° C. EDCI (247 mg, 1.29 mmol) was added and the reaction mixture was stirred under a nitrogen atmosphere overnight. The reaction solution was washed with sat. NaCl solution (50 ml), dried over $Na_2SO_4$ and concentrated to dryness. The product was purified via preparative LCMS. LCMS analysis: MS, m/z 631.4 ($MH^+$)

Example 42

N-Cyclopropyl-N-(2-(2-(4-(4-cyclopropylpiperazin-1-yl)-4-((1-oxoisoindolin-2-yl)methyl)piperidin-1-yl)-2-oxoethoxy)ethyl)-4-methoxy-2,6-dimethylbenzenesulfonamide

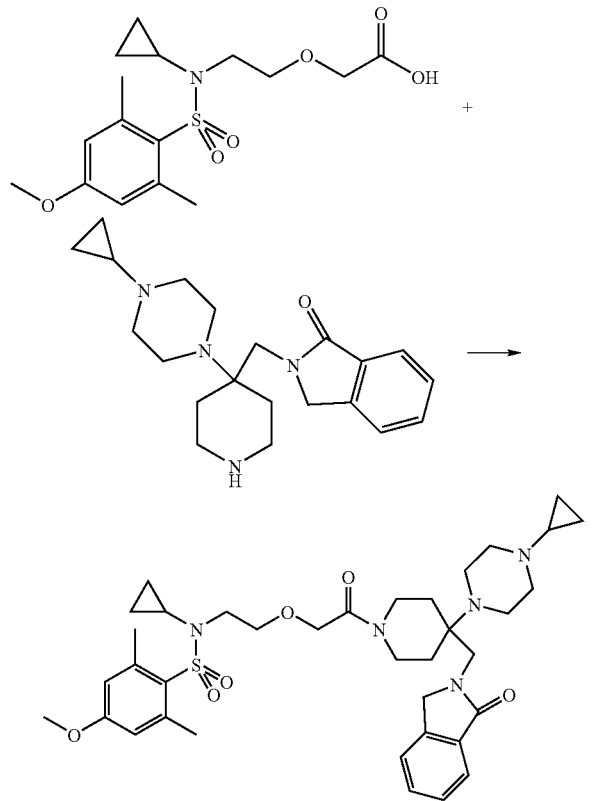

To a solution of 2-(2-(N-cyclopropyl-4-methoxy-2,6-dimethylphenyl-sulfonamido)ethoxy)acetic acid AC7 (0.306 mmol) in dichloromethane (10 ml/mmol) was added diisopropyl ethylamine (4.0 equiv.) at 0° C. followed by the addition of HOBT (1.0 equiv.) and EDCI (1.5 equiv.). The resultant solution was stirred at 25° C. for 15 min. It was again cooled to 0° C. and a solution of 2-((4-(4-cyclopropylpiperazin-1-yl)piperidin-4-yl)methyl)isoindolin-1-one AM13 (1.2 equiv) in dichloromethane (2 ml) was added. The reaction mixture was stirred for 16 h at 25° C. The mixture was diluted with dichloromethane, washed with saturated ammonium chloride solution, brine, saturated sodium bicarbonate and finally again with brine. The organic layer was dried over sodium sulfate and evaporated to dryness under reduced pressure to give the crude product which was purified by column chromatography. Yield: 50%. MS, $R_t$=3.4 min, m/z=694.5 $[MH]^+$.

Example 43

N-((1-(2-(2-(2-Chloro-N-cyclopropyl-6-methylphenyl-sulfonamido)ethoxy)acetyl)-4-(4-cyclopropylpiperazin-1-yl)piperidin-4-yl)-methyl)isonicotinamide

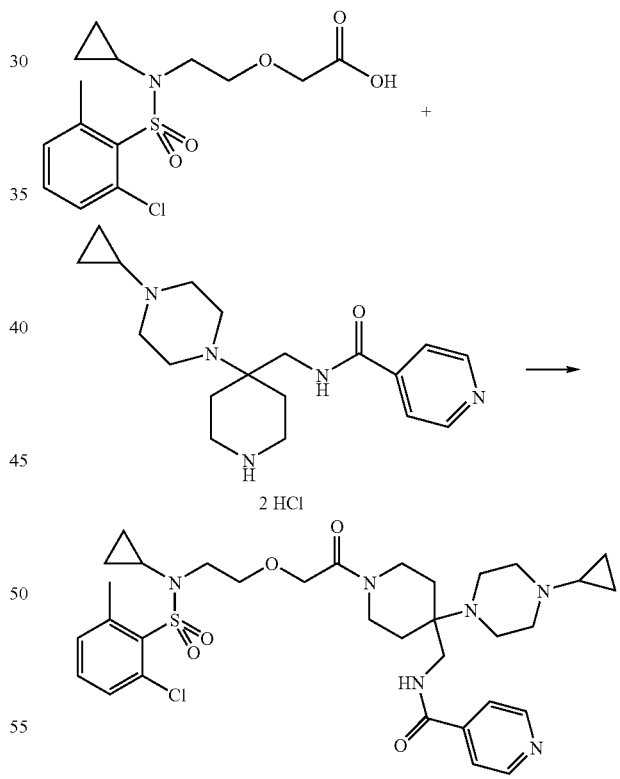

To a solution of 2-(2-(2-chloro-N-cyclopropyl-6-methylphenylsulfonamido)-ethoxy)acetic acid AC8 (0.225 mmol) in dichloromethane (10 ml/mmol) was added diisopropyl ethylamine (4 equiv.) at 0° C. followed by the addition of HOBT (1.0 equiv.) and EDCI (1.5 equiv.). The resulting solution was stirred at 25° C. for 15 min. It was again cooled to 0° C. and a solution of N-((4-(4-cyclopropyl-piperazin-1-yl)piperidin-4-yl)methyl)isonicotinamide dihydrochloride AM12 (1.2 equiv.) in DMF (2 ml) was added. The reaction mixture was stirred for 16 h at 25° C. The mixture was diluted with dichloromethane, washed with saturated ammonium chloride solution, brine, saturated sodium bicarbonate and finally again with brine. The organic layer was dried over sodium sulfate and evaporated to dryness under reduced pressure to give the crude product which was purified by column chromatography. Yield: 55%. MS, $R_t$=2.8 min, m/z=673.4 [MH]+.

Example 44

N-((1-(2-(2-(N-Cyclopropyl-4-methoxy-2,6-dimethylphenyl-sulfonamido)ethoxy)acetyl)-4-(4-cyclopropylpiperazin-1-yl)piperidin-4-yl)-methyl)-isonicotinamide

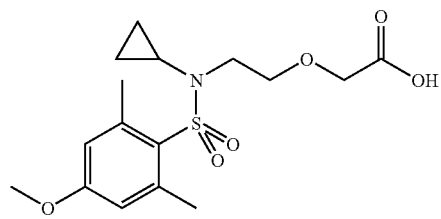

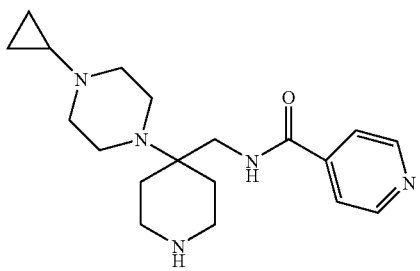

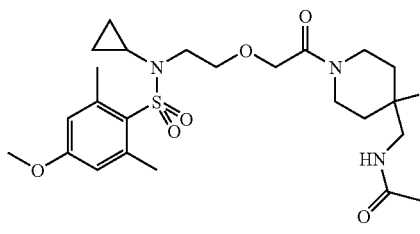

To a solution of 2-(2-(N-cyclopropyl-4-methoxy-2,6-dimethylphenyl-sulfonamido)ethoxy)acetic acid AC7 (0.225 mmol) in dichloromethane (10 ml/mmol) was added diisopropyl ethylamine (4 equiv.) at 0° C. followed by the addition of HOBT (1.0 equiv.) and EDCI (1.5 equiv.). The resultant solution was stirred at 25° C. for 15 min. It was again cooled to 0° C. and a solution of N-((4-(4-cyclopropylpiperazin-1-yl)piperidin-4-yl)methyl)isonicotinamide dihydrochloride AM12 (1.2 equiv.) in DMF (2 ml) was added. The reaction mixture was stirred for 16 h at 25° C. The mixture was diluted with dichloromethane, washed with saturated ammonium chloride solution, brine, saturated sodium bicarbonate and finally again with brine. The organic layer was dried over sodium sulfate and evaporated to dryness under reduced pressure to yield the crude product which was purified by column chromatography. Yield: 60%. MS, $R_t$=2.8 min, m/z 683.5 [MH]+.

Example 45

(S)—N-((4-(4-Cyclopropylpiperazin-1-yl)-1-(2-((1-(4-methoxy-2,6-dimethylphenylsulfonyl)indolin-2-yl)methoxy)acetyl)piperidin-4-yl)-methyl)isonicotinamide

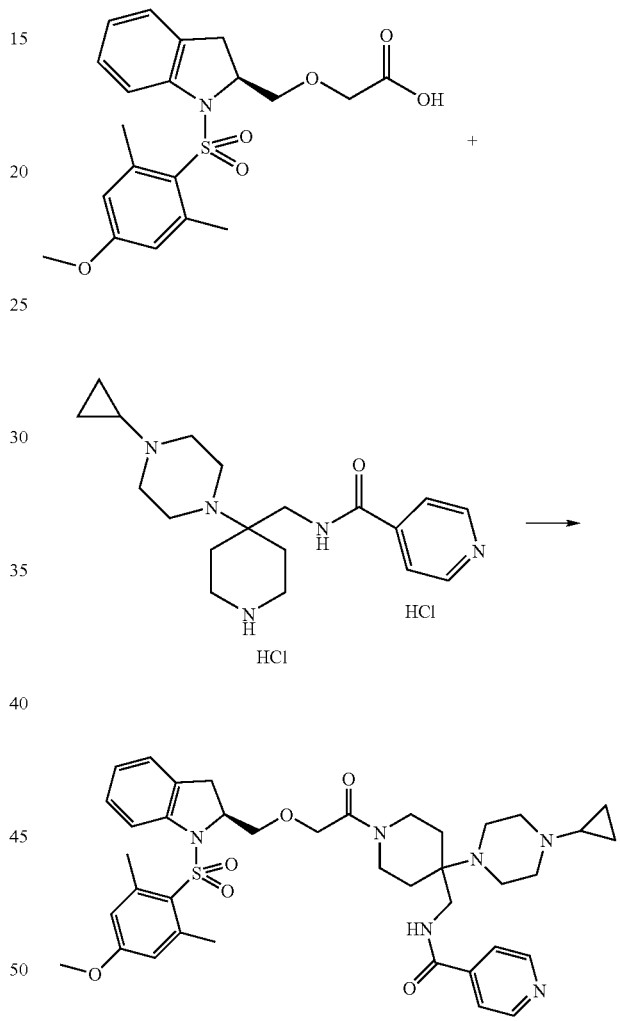

To a solution of (S)-2-((1-(4-methoxy-2,6-dimethylphenylsulfonyl)indolin-2-yl)methoxy)acetic acid AC10 (0.282 mmol) in dichloromethane (10 ml/mmol) was added diisopropyl ethylamine (4 equiv.) at 0° C. followed by the addition of HOBT (1.0 equiv.) and EDCI (1.5 equiv.). The resultant solution was stirred at 25° C. for 15 min. It was again cooled to 0° C. and a solution of N-((4-(4-cyclopropyl-piperazin-1-yl)piperidin-4-yl)methyl)isonicotinamide dihydrochloride AM12 (1.2 equiv.) in DMF (2 ml) was added. The reaction mixture was stirred for 16 h at 25° C. The mixture was diluted with dichloromethane, washed with saturated ammonium chloride solution, brine, saturated sodium bicarbonate and finally again with brine. The organic layer was dried over sodium sulfate and evaporated to dryness under reduced pressure to yield the crude product which was purified by column chromatography. Yield: 58%. MS, $R_t$=3.2 min, m/z=731.5 [MH]+.

Example 46

N-((1-(2-(2-(N-Cyclopropyl-4-methoxy-2,6-dimethylphenyl-sulfonamido)ethoxy)acetyl)-4-(4-(pyridin-4-yl)piperazin-1-yl)piperidin-4-yl)-methyl)acetamide

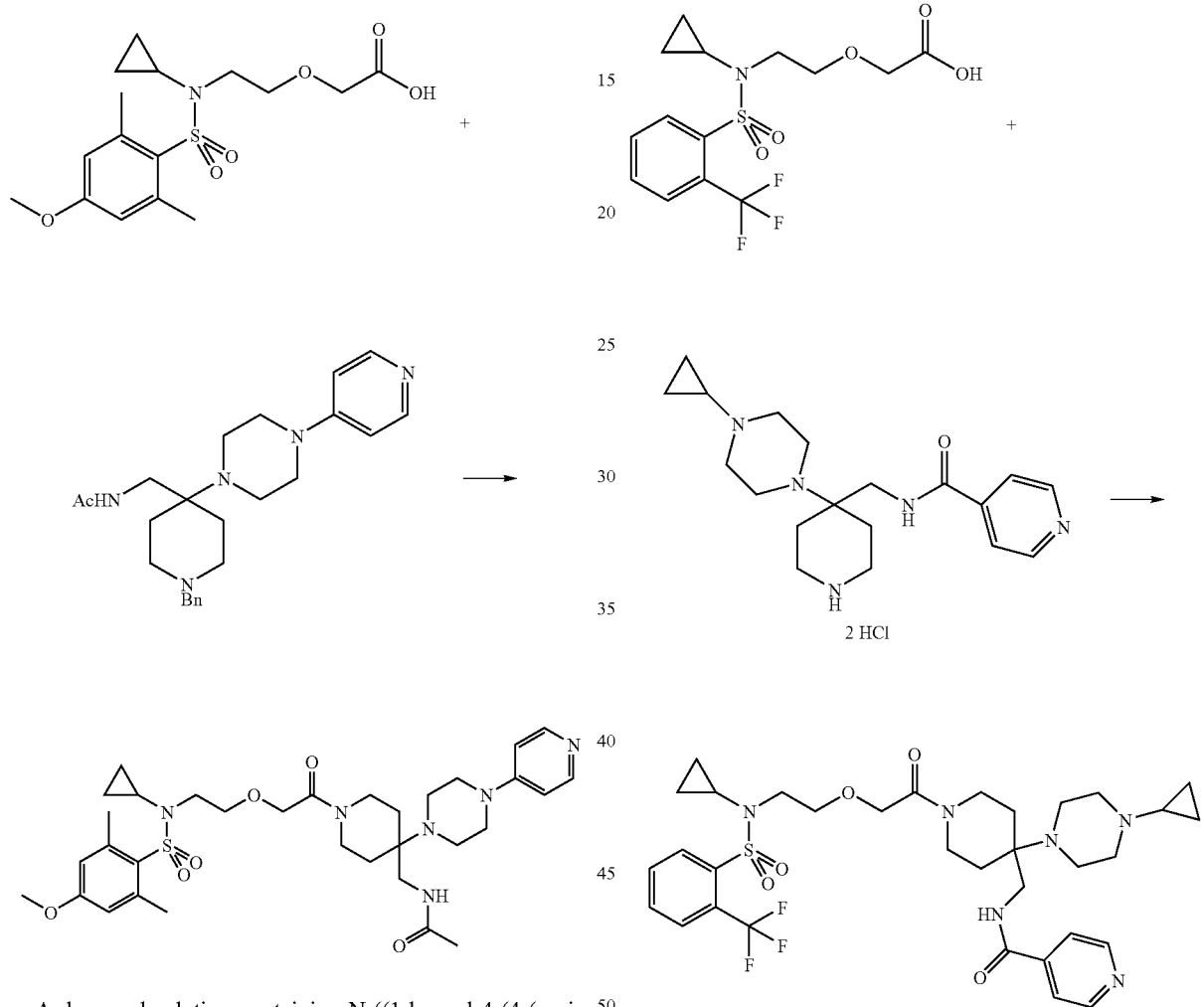

A degassed solution containing N-((1-benzyl-4-(4-(pyridin-4-yl)piperazin-1-yl)piperidin-4-yl)methyl)acetamide AM14 (1.96 mmol), AcOH (0.3 ml) and Pd(OH)$_2$ in methanol was hydrogenated for 16 h to yield N-((4-(4-(pyridin-4-yl)-piperazin-1-yl)piperidin-4-yl)methyl)acetamide AM2, which was obtained after passage through a celite pad and solvent removed under reduced pressure. N-((4-(4-(pyridin-4-yl)piperazin-1-yl)piperidin-4-yl)methyl)acetamide AM2 was re-dissolved in dichloromethane and added to a solution containing 2-(2-(N-cyclopropyl-4-methoxy-2,6-dimethylphenylsulfonamido)ethoxy)acetic acid AC7 (0.8 equiv.), EDCI (1.5 equiv.), HOBT (1 equiv.) and DIPEA (4 equiv.) in dichloromethane at 0° C. The reaction mixture was warmed to room temperature and stirred for 16 h. The mixture was diluted with dichloromethane and was given aq. NH$_4$Cl and aq. NaHCO$_3$ washes. The organic layer was dried over sodium sulfate and the solvent removed. The crude product was purified by alumina column chromatography. Yield: 5%. MS, $R_t$=2.5 min, m/z=657.5 [MH]+.

Example 47

N-((1-(2-(2-(N-Cyclopropyl-2-(trifluoromethyl)phenyl-sulfonamido)ethoxy)acetyl)-4-(4-cyclopropylpiperazin-1-yl)piperidin-4-yl)-methyl)isonicotinamide To a solution of 2-(2-(N-cyclopropyl-2-(trifluoromethyl)phenylsulfonamido)-ethoxy)acetic acid AC9 (0.472 mmol) in dichloromethane (10 ml/mmol) was added diisopropyl ethylamine (4 equiv.) at 0° C. followed by the addition of HOBT (1.0 equiv.) and EDCI (1.5 equiv.). The resultant solution was stirred at 25° C. for 15 min. It was again cooled to 0° C. and a solution of N-((4-(4-cyclopropylpiperazin-1-yl)piperidin-4-yl)methyl)isonicotinamide dihydrochloride AM12 (1.2 equiv.) in DMF (2 ml) was added. The reaction mixture was stirred for 16 h at 25° C. The mixture was diluted with dichloromethane, washed with saturated ammonium chloride solution, brine, saturated sodium bicarbonate and finally again with brine. The organic layer was dried over sodium sulfate and evaporated to dryness under reduced pressure to give the crude product which was purified by column chromatography. Yield: 55%. MS, $R_t$=2.8 min, m/z=693.5 [MH]+.

Example 48

N-((1-(2-(2-(4-Methoxy-N,2,6-trimethylphenylsulfonamido)-ethoxy)acetyl)-4-(4-methylpiperazin-1-yl)piperidin-4-yl)methyl)-isonicotinamide hydrochloride

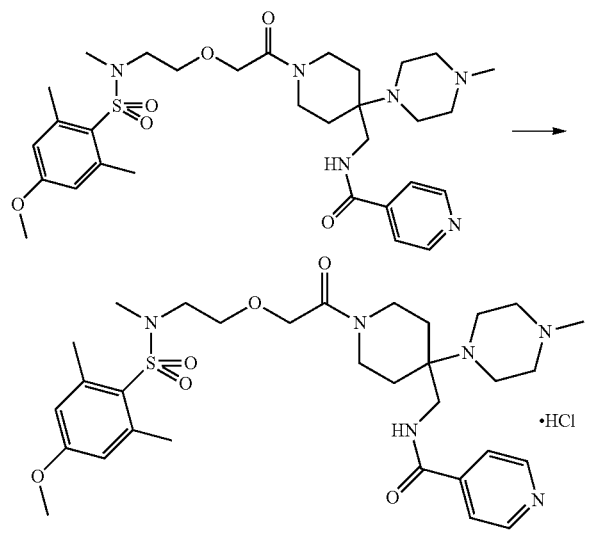

To a solution of N-((1-(2-(2-(4-methoxy-N,2,6-trimethylphenyl-sulfonamido)ethoxy)acetyl)-4-(4-methylpiperazin-1-yl)piperidin-4-yl)methyl)-isonicotinamide (Example 1) (730 mg) in dioxane (5 ml) was added dioxane-HCl (15 ml) at 0° C. and the reaction mixture was stirred at room temperature for 1 h. The solvent was evaporated under reduced pressure and the residue was azeotroped (2×) with dichloromethane to obtain the desired hydrochloride salt. Yield: quantitative. MS, $R_t$=2.4 min, m/z=631.5 [MH]+

Equipment and Methods Used for HPLC-MS-Analysis of Examples 1 & 42 to 48:

HPLC: Waters Alliance 2795 with PDA Waters 2998; MS: Micromass Quattro Micro™ API; Column: Waters Atlantis®T3, 3 µm, 100 Å, 2.1×30 mm; temp.: 40° C., Eluent A: water+0.1% formic acid; Eluent B: acetonitrile+0.1% formic acid; Gradient: 0% B to 100% B in 8.8 min, 100% B for 0.4 min, 100% B to 0% B in 0.01 min, 0% B for 0.8 min; Flow: 1.0 mL/min; Ionisation: ES+, 25 V; Make up: 100 µL/min 70% Methanol+0.2% formic acid; UV: 200-400 nm The Example Compounds (2) to (41) and (49) to (54) prepared by means of the parallel syntheses were analyzed, inter alia, with the aid of their molecular weight. The particular method used for the synthesis and the molecular weights measured by means of ESI-MS are summarized in the following table.

| Example | AC | AM | Method | Name | Mass (ESI-MS) |
|---|---|---|---|---|---|
| 2 | 4 | 3 | A | N-((1-(3-(1-(4-Chloro-2,5-dimethylphenylsulfonyl)piperidin-2-yl)propanoyl)-4-(4-methylpiperazin-1-yl)piperidin-4-yl)methyl)acetamide | 595.3 |
| 3 | 5 | 5 | A | N-((1-(2-((1-(4-Methoxy-2,6-dimethyl-phenylsulfonyl)piperidin-2-yl)methoxy)-acetyl)-4-(4-methylpiperazin-1-yl)piperidin-4-yl)methyl)-2-phenylacetamide | 683.4 |
| 4 | 3 | 5 | A | N-((4-(4-Methylpiperazin-1-yl)-1-(2-(1-(3-(trifluoromethyl)phenylsulfonyl)piperidin-2-yl)acetyl)piperidin-4-yl)methyl)-2-phenylacetamide | 663.3 |
| 5 | 5 | 4 | A | N-((1-(2-((1-(4-Methoxy-2,6-dimethylphenylsulfonyl)piperidin-2-yl)methoxy)acetyl)-4-(4-methylpiperazin-1-yl)piperidin-4-yl)methyl)benzamide | 669.4 |
| 6 | 4 | 4 | A | N-((1-(3-(1-(4-Chloro-2,5-dimethylphenylsulfonyl)piperidin-2-yl)propanoyl)-4-(4-methylpiperazin-1-yl)piperidin-4-yl)methyl)benzamide | 657.3 |
| 7 | 6 | 3 | A | N-((1-(2-((1-(3,4-Dichlorophenylsulfonyl)-1,2,3,4-tetrahydroquinolin-2-yl)methoxy)acetyl)-4-(4-methylpiperazin-1-yl)piperidin-4-yl)methyl)acetamide | 665.2 |
| 8 | 2 | 5 | A | N-((4-(4-Methylpiperazin-1-yl)-1-(3-(naphthalene-2-sulfonamido)-3-phenylpropanoyl)piperidin-4-yl)methyl)-2-phenylacetamide | 667.3 |
| 9 | 4 | 1 | A | N-((1-(3-(1-(4-Chloro-2,5-dimethylphenylsulfonyl)piperidin-2-yl)propanoyl)-4-(4-methylpiperazin-1-yl)piperidin-4-yl)methyl)picolinamide | 658.3 |
| 10 | 4 | 5 | A | N-((1-(3-(1-(4-Chloro-2,5-dimethylphenyl-sulfonyl)piperidin-2-yl)propanoyl)-4-(4-methylpiperazin-1-yl)piperidin-4-yl)methyl)-2-phenylacetamide | 671.3 |
| 11 | 4 | 2 | A | N-((1-(3-(1-(4-Chloro-2,5-dimethylphenylsulfonyl)piperidin-2-yl)propanoyl)-4-(4-(pyridin-4-yl)piperazin-1-yl)piperidin-4-yl)methyl)acetamide | 658.3 |

-continued

| Example | AC | AM | Method | Name | Mass (ESI-MS) |
|---|---|---|---|---|---|
| 12 | 3 | 3 | A | N-((4-(4-Methylpiperazin-1-yl)-1-(2-(1-(3-(trifluoromethyl)phenylsulfonyl)piperidin-2-yl)acetyl)piperidin-4-yl)methyl)acetamide | 587.3 |
| 13 | 6 | 5 | A | N-((1-(2-((1-(3,4-Dichlorophenylsulfonyl)-1,2,3,4-tetrahydroquinolin-2-yl)methoxy)-acetyl)-4-(4-methylpiperazin-1-yl)piperidin-4-yl)methyl)-2-phenylacetamide | 741.3 |
| 14 | 2 | 2 | A | N-((1-(3-(Naphthalene-2-sulfonamido)-3-phenylpropanoyl)-4-(4-(pyridin-4-yl)piperazin-1-yl)piperidin-4-yl)methyl)-acetamide | 654.3 |
| 15 | 1 | 5 | A | N-((1-(2-(2-(4-Methoxy-N,2,6-trimethylphenylsulfonamido)ethoxy)acetyl)-4-(4-methylpiperazin-1-yl)piperidin-4-yl)methyl)-2-phenylacetamide | 643.3 |
| 16 | 2 | 4 | A | N-((4-(4-Methylpiperazin-1-yl)-1-(3-(naphthalene-2-sulfonamido)-3-phenylpropanoyl)piperidin-4-yl)methyl)-benzamide | 653.3 |
| 17 | 6 | 2 | B | N-((1-(2-((1-(3,4-Dichlorophenylsulfonyl)-1,2,3,4-tetrahydroquinolin-2-yl)methoxy)-acetyl)-4-(4-(pyridin-4-yl)piperazin-1-yl)-piperidin-4-yl)methyl)acetamide | 728.2 |
| 18 | 3 | 4 | A | N-((4-(4-Methylpiperazin-1-yl)-1-(2-(1-(3-(trifluoromethyl)phenylsulfonyl)piperidin-2-yl)acetyl)piperidin-4-yl)methyl)picolinamide | 650.3 |
| 19 | 2 | 1 | A | N-((4-(4-Methylpiperazin-1-yl)-1-(3-(naphthalene-2-sulfonamido)-3-phenyl-propanoyl)piperidin-4-yl)methyl)-picolinamide | 654.3 |
| 20 | 6 | 1 | A | N-((1-(2-((1-(3,4-Dichlorophenylsulfonyl)-1,2,3,4-tetrahydroquinolin-2-yl)methoxy)acetyl)-4-(4-methylpiperazin-1-yl)piperidin-4-yl)methyl)picolinamide | 728.2 |
| 21 | 5 | 1 | A | N-((1-(2-((1-(4-Methoxy-2,6-dimethyl-phenylsulfonyl)piperidin-2-yl)methoxy)-acetyl)-4-(4-methylpiperazin-1-yl)piperidin-4-yl)methyl)picolinamide | 670.4 |
| 22 | 5 | 2 | A | N-((1-(2-((1-(4-Methoxy-2,6-dimethyl-phenylsulfonyl)piperidin-2-yl)methoxy)-acetyl)-4-(4-(pyridin-4-yl)piperazin-1-yl)-piperidin-4-yl)methyl)acetamide | 670.4 |
| 23 | 6 | 4 | A | N-((1-(2-((1-(3,4-Dichlorophenylsulfonyl)-1,2,3,4-tetrahydroquinolin-2-yl)methoxy)acetyl)-4-(4-methylpiperazin-1-yl)piperidin-4-yl)methyl)benzamide | 727.2 |
| 24 | 1 | 4 | A | N-((1-(2-(2-(4-Methoxy-N,2,6-trimethyl-phenylsulfonamido)ethoxy)acetyl)-4-(4-methylpiperazin-1-yl)piperidin-4-yl)methyl)-benzamide | 629.3 |
| 25 | 1 | 1 | A | N-((1-(2-(2-(4-Methoxy-N,2,6-trimethylphenylsulfonamido)ethoxy)acetyl)-4-(4-methylpiperazin-1-yl)piperidin-4-yl)methyl)picolinamide | 630.3 |
| 26 | * | 8 | B | N-((1-(3-(1-(4-Chloro-2,5-dimethyl-phenylsulfonyl)piperidin-2-yl)propanoyl)-4-(4-methylpiperazin-1-yl)piperidin-4-yl)-methyl)isonicotinamide | 658.3 |
| 27 | 5 | 3 | A | N-((1-(2-((1-(4-Methoxy-2,6-dimethylphenylsulfonyl)piperidin-2-yl)methoxy)acetyl)-4-(4-methylpiperazin-1-yl)piperidin-4-yl)methyl)acetamide | 607.3 |
| 28 | * | 9 | B | N-((1-(2-((1-(4-Methoxy-2,6-dimethylphenylsulfonyl)piperidin-2-yl)methoxy)acetyl)-4-(4-methylpiperazin-1-yl)piperidin-4-yl)methyl)isonicotinamide | 670.4 |
| 29 | * | 10 | B | N-((4-(4-Methylpiperazin-1-yl)-1-(2-(1-(3-(trifluoromethyl)phenylsulfonyl)piperidin-2-yl)acetyl)piperidin-4-yl)methyl)isonicotinamide | 650.3 |
| 30 | * | 11 | B | N-((1-(2-((1-(3,4-Dichlorophenylsulfonyl)-1,2,3,4-tetrahydroquinolin-2-yl)methoxy)acetyl)-4-(4-methylpiperazin-1-yl)piperidin-4-yl)methyl)isonicotinamide | 728.2 |

-continued

| Example | AC | AM | Method | Name | Mass (ESI-MS) |
|---|---|---|---|---|---|
| 31 | 1 | 3 | A | N-((1-(2-(2-(4-Methoxy-N,2,6-trimethylphenylsulfonamido)ethoxy)acetyl)-4-(4-methylpiperazin-1-yl)piperidin-4-yl)methyl)acetamide | 567.3 |
| 32 | * | 6 | B | N-((1-(2-(2-(4-Methoxy-N,2,6-trimethyl-phenylsulfonamido)ethoxy)acetyl)-4-(4-methylpiperazin-1-yl)piperidin-4-yl)methyl)-nicotinamide | 630.3 |
| 33 | * | 8 | B | N-((1-(3-(1-(4-Chloro-2,5-dimethylphenyl-sulfonyl)piperidin-2-yl)propanoyl)-4-(4-methylpiperazin-1-yl)piperidin-4-yl)methyl)-nicotinamide | 658.3 |
| 34 | * | 9 | B | N-((1-(2-((1-(4-Methoxy-2,6-dimethylphenylsulfonyl)piperidin-2-yl)methoxy)acetyl)-4-(4-methylpiperazin-1-yl)piperidin-4-yl)methyl)nicotinamide | 670.4 |
| 35 | 2 | 3 | A | N-((4-(4-Methylpiperazin-1-yl)-1-(3-(naphthalene-2-sulfonamido)-3-phenyl-propanoyl)piperidin-4-yl)methyl)acetamide | 591.3 |
| 36 | 3 | 2 | A | N-((4-(4-(Pyridin-4-yl)piperazin-1-yl)-1-(2-(1-(3-(trifluoromethyl)phenylsulfonyl)-piperidin-2-yl)acetyl)piperidin-4-yl)methyl)-acetamide | 650.3 |
| 37 | * | 7 | B | N-((4-(4-Methylpiperazin-1-yl)-1-(3-(naphthalene-2-sulfonamido)-3-phenyl-propanoyl)piperidin-4-yl)methyl)-isonicotinamide | 654.3 |
| 38 | * | 7 | B | N-((4-(4-Methylpiperazin-1-yl)-1-(3-(naphthalene-2-sulfonamido)-3-phenyl-propanoyl)piperidin-4-yl)methyl)-nicotinamide | 654.3 |
| 39 | * | 10 | A | N-((4-(4-Methylpiperazin-1-yl)-1-(2-(1-(3-(trifluoromethyl)phenylsulfonyl)piperidin-2-yl)acetyl)piperidin-4-yl)methyl)nicotinamide | 650.3 |
| 40 | * | 11 | B | N-((1-(2-((1-(3,4-Dichlorophenylsulfonyl)-1,2,3,4-tetrahydroquinolin-2-yl)-methoxy)-acetyl)-4-(4-methylpiperazin-1-yl)piperidin-4-yl)methyl)nicotinamide | 728.2 |
| 41 | 1 | 2 | A | N-((1-(2-(2-(4-Methoxy-N,2,6-trimethyl-phenylsulfonamido)ethoxy)acetyl)-4-(4-(pyridin-4-yl)piperazin-1-yl)piperidin-4-yl)methyl)acetamide | 630.3 |
| 49 | 11 | 15 | C | N-((1-(2-((4-(4-Methoxy-2,6-dimethyl-phenylsulfonyl)-3,4-dihydro-2H-benzo[b]-[1,4]oxazin-3-yl)methoxy)acetyl)-4-(4-methylpiperazin-1-yl)piperidin-4-yl)methyl)-isonicotinamide | 721.5 |
| 50 | 12 | 15 | C | N-((1-(2-((4-(2-Chloro-6-methylphenyl-sulfonyl)-3,4-dihydro-2H-benzo[b][1,4]-oxazin-3-yl)methoxy)acetyl)-4-(4-methyl-piperazin-1-yl)piperidin-4-yl)methyl)-isonicotinamide | 711.4 |
| 51 | 16 | 15 | C | N-((1-(2-(2-(4-Methoxy-N,2,3,6-tetramethylphenylsulfonamido)ethoxy)acetyl)-4-(4-methylpiperazin-1-yl)piperidin-4-yl)methyl)isonicotinamide | 645.4 |
| 52 | 13 | 15 | C | N-((1-(3-((1-(4-Methoxy-2,6-dimethyl-phenylsulfonyl)piperidin-2-yl)methoxy)-propanoyl)-4-(4-methylpiperazin-1-yl)piperidin-4-yl)methyl)isonicotinamide | 685.5 |
| 53 | 14 | 15 | C | N-((1-(2-(2-(1-(4-Methoxy-2,6-dimethylphenylsulfonyl)piperidin-2-yl)ethoxy)acetyl)-4-(4-methylpiperazin-1-yl)piperidin-4-yl)methyl)isonicotinamide | 685.4 |
| 54 | 15 | 15 | C | N-((1-(4-(N-Methyl-3-(trifluoromethyl)phenylsulfonamido)butanoyl)-4-(4-methylpiperazin-1-yl)piperidin-4-yl)methyl)isonicotinamide | 625.3 |

In the above listed compounds obtained according to Method B, the following acid chlorides were used as acid units (denoted with (*)): 26; 28; 29; 30: Isonicotinyl chloride; 32; 33; 34; 37; 38; 39; and 40: nicotinyl chloride.

Pharmacological Investigations

1. Functional Investigation on the Bradykinin 1 Receptor (B1R)

The agonistic or antagonistic action of substances can be determined on the bradykinin 1 receptor (B1R) of humans and rats by means of a cell-based flourescent calcium-mobilization assay. According to this assay agonist-induced increase of intracellular free $Ca^{2+}$ is quantified by means of a $Ca^{2+}$-sensitive dye (Fluo-4 type, Molecular Probes Europe BV, Leiden, Netherlands), in a Fluorescent Imaging Plate Reader (FLIPR, Molecular Devices, Sunnyvale, USA) and/or the Novostar (BMG Labtech GmbH, Offenburg, Germany).

Method:

Chinese hamster ovary cells (CHO K1 cells), which are stably transfected with the human B1R gene (hB1R cells) or with the B1R gene of rats (rB1R cells), are used. For functional investigations these cells are seeded into black 96-well plates with a clear bottom (BD Biosciences, Heidelberg, Germany or Greiner, Frickenhausen, Germany) in a density of 20,000-35,000 cells/well. The cells are incubated overnight in a humidified atmosphere at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % FBS (foetal bovine serum, Gibco Invitrogen GmbH, Karlsruhe, Germany).

On the following day the cells are loaded with the $Ca^{2+}$-sensitive dye Fluo-4-AM (Molecular Probes Europe BV, Leiden, Netherlands):

Method A: The medium of the cells is removed and cell plates are incubated with loading solution, which contains 2.13 µM Fluo-4-AM, 2.5 mM probenecid (Sigma-Aldrich, Taufkirchen, Germany), and 10 mM HEPES (Sigma-Aldrich, Taufkirchen, Germany) in HBSS buffer (Hank's buffered saline solution, Gibco Invitrogen GmbH, Karlsruhe, Germany) for 60 minutes at 37° C. After the plates are washed twice with HBSS buffer, HBSS buffer supplemented 0.1% BSA (bovine serum albumin; Sigma-Aldrich, Taufkirchen, Germany), 5.6 mM glucose and 0.05% gelatine (Merck KGaA, Darmstadt, Germany) is added. Cell plates are incubated for at least 20 minutes in the dark at room temperature before they are used for the $Ca^{2+}$ measurement in the FLIPR or Novostar.

Method B: The plates are washed with buffer A (15 mM HEPES, 80 mM NaCl, 5 mM KCl, 1.2 mM $CaCl_2$, 0.7 mM $MgSO_4$, 2 mg/ml glucose, 2.5 mM probenecid) and subsequently loaded with buffer A containing 2.4 µM Fluo-4-AM and 0.025% pluronic F127 (Sigma-Aldrich, Taufkirchen, Germany) for 60 minutes at 37° C. Cell plates are washed twice with buffer A. Then, buffer A supplemented with 0.05% BSA and 0.05% gelatine is added and cell plates are incubated in the dark at room temperature for at least 20 minutes before measurement in the FLIPR or Novostar is started.

Fluorescence Assay:

The $Ca^{2+}$-dependent fluorescence is measured both before and after the addition of substances ($\lambda_{ex}$=488 nm, $\lambda_{em}$=540 nm). For quantification of the effect the highest fluorescence intensity (FC, fluorescence counts) over time is given. The FLIPR protocol consists of two substance additions, done within the instrument while continuously monitoring the $Ca^{2+}$-dependent fluorescence at 540 nm. When the Novostar was used, one addition had to be done outside the instrument. Test substances (10 µM) are initially pipetted onto the cells and the intracellular $Ca^{2+}$ rise is compared with the control (hB1R: Lys-Des-Arg9-bradykinin>=50 nM; rB1R: Des-Arg9-bradykinin>=1 µM). This gives the result in % activation referred to the $Ca^{2+}$ signal after addition of Lys-Des-Arg9-bradykinin (>=50 nM), or. Des-Arg9-bradykinin (>=1 µM), respectively. After incubation of test substances for 6-20 minutes the agonists Lys-Des-Arg9-bradykinin (hB1R) and Des-Arg$^9$-bradykinin (rB1R) are applied in the $EC_{80}$ concentration and the increase of $Ca^{2+}$ is likewise determined. Antagonists lead to a suppression of the $Ca^{2+}$ increase. The % inhibition compared to the maximum achievable inhibition is calculated. The compounds show a good activity on both human and rat receptors.

Results of the Pharmacological Studies

The agonistic or antagonistic action of the compounds according to the invention on human and rat bradykinin 1 receptors (B1R) was determined as described above. Antagonists lead to a suppression of the $Ca^2$ increase. % inhibition compared with the maximum achievable inhibition was calculated.

| Example | B1R antagonism, human [10 µM] % inhibition | B1R antagonism, rat [10 µM] % inhibition |
|---|---|---|
| 1 | 107 | 101 |
| 2 | 81 | 74 |
| 3 | 103 | 104 |
| 4 | 67 | 59 |
| 5 | 102 | 104 |
| 6 | 99 | 24 |
| 7 | 102 | 105 |
| 8 | 75 | 29 |
| 9 | 99 | 11 |
| 10 | 101 | 39 |
| 11 | 102 | 75 |
| 12 | 80 | 13 |
| 13 | 104 | 52 |
| 14 | 100 | 82 |
| 15 | 103 | 101 |
| 16 | 94 | 31 |
| 17 | 104 | 101 |
| 18 | 97 | 17 |
| 19 | 102 | 83 |
| 20 | 91 | 60 |
| 21 | 103 | 101 |
| 22 | 103 | 101 |
| 23 | 99 | 54 |
| 24 | 103 | 101 |
| 25 | 103 | 101 |
| 26 | 103 | 45 |
| 27 | 103 | 102 |
| 28 | 102 | 102 |
| 29 | 67 | 33 |
| 30 | 100 | 80 |
| 31 | 103 | 101 |
| 32 | 104 | 101 |
| 33 | 103 | 100 |
| 34 | 104 | 102 |
| 35 | 89 | 102 |
| 36 | 99 | 101 |
| 37 | 46 | 71 |
| 38 | 50 | 73 |
| 39 | 11 | 94 |
| 40 | 49 | 103 |
| 41 | 100 | 102 |
| 42 | 97 | 96 |
| 43 | 100 | 103 |
| 44 | 100 | 102 |
| 45 | 100 | 102 |
| 46 | 100 | 101 |
| 47 | 100 | 99 |
| 48 | 100 | 97 |

-continued

| Example | B1R antagonism, human [10 μM] % inhibition | B1R antagonism, rat [10 μM] % inhibition |
| --- | --- | --- |
| 49 | 100 | 102 |
| 50 | 96 | 102 |
| 51 | 100 | 103 |
| 52 | 100 | 102 |
| 53 | — | 102 |
| 54 | — | 66 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted sulfonamide compound corresponding to formula I:

wherein
n represents 0, 1 or 2;
o represents 1, 2 or 3;
p represents 1 or 2;
q represents 0 or 1;
r represents 0 or 1;
the sum of p+q+r equals 3;
Q represents a single bond, —O— or —CH$_2$—;
$R^1$ represents aryl or heteroaryl or denotes an aryl or heteroaryl bonded via a C$_{1-3}$-alkylene group;
$R^2$ represents H, C$_{1-6}$-alkyl, C$_{3-8}$cycloalkyl, aryl or heteroaryl; or denotes a C$_{3-8}$-cycloalkyl, aryl or heteroaryl bonded via a C$_{1-6}$-alkylene group, C$_{2-6}$-alkenylene group or C$_{2-6}$-alkynylene group; and
$R^3$ represents H, C$_{1-6}$-alkyl, aryl or heteroaryl; or denotes an aryl or heteroaryl bonded via a C$_{1-6}$-alkylene group, C$_{2-6}$-alkenylene group or C$_{2-6}$-alkynylene group; or
$R^2$ and $R^3$ together form a heterocyclic ring, which optionally may be fused with an aryl or heteroaryl ring,
wherein said heterocyclic ring may be saturated or mono- or polyunsaturated, but not aromatic, is 4-, 5-, 6- or 7-membered, and may contain in addition to the N hetero atom to which $R^2$ is bonded, at least one further hetero atom or group selected from the group consisting of N, NR$^{12}$, O, S, S=O and S(=O)$_2$;
wherein $R^{12}$ represents H, C$_{1-6}$-alkyl, —C(=O)—R$^{13}$, C$_{3-8}$-cycloalkyl, aryl, heteroaryl or a C$_{3-8}$-cycloalkyl, aryl or heteroaryl bonded via a C$_{1-3}$-alkylene group, and R$^{13}$ denotes C$_{1-6}$-alkyl, C$_{3-8}$-cycloalkyl, aryl, heteroaryl or a C$_{3-8}$-cycloalkyl, aryl or heteroaryl bonded via a C$_{1-3}$-alkylene group, $R^4$ and $R^5$ each independently represent H, C$_{1-6}$-alkenyl, C$_{2-6}$-alkynyl, C$_{3-8}$-cycloalkyl, 3- to 8-membered heterocycloalkyl, aryl or heteroaryl or a C$_{3-8}$-cycloalkyl, 3- to 8-membered heterocycloalkyl, aryl or heteroaryl bonded via a C$_{1-3}$-alkylene group; or
$R^4$ and $R^5$ together form an unsubstituted or mono- or polysubstituted heterocyclic ring, which optionally may be fused with a saturated or mono- or polyunsaturated or aromatic, unsubstituted or mono- or polysubstituted ring system,
wherein said heterocyclic ring may be saturated or mono- or polyunsaturated but not aromatic, is 4-, 5-, 6- or 7-membered, and may contain in addition to the N hetero atom to which $R^4$ and $R^5$ are bound, at least one hetero atom or group selected from the group consisting of N, NR$^8$, O, S, S=O and S(=O)$_2$, wherein $R^8$ represents a moiety selected from the group consisting of H, C$_{1-6}$-alkyl, C$_{3-8}$-cycloalkyl, aryl, heteroaryl, and aryl, or denotes heteroaryl or C$_{3-8}$-cycloalkyl bonded via a C$_{1-3}$-alkylene group, and
wherein said ring system is 4-, 5-, 6- or 7-membered, and optionally may contain at least one hetero atom or group selected from the group consisting of N, NR$^{17}$, O, S, S=O and S(=O)$_2$, wherein $R^{17}$ represents a moiety selected from the group consisting of H, C$_{1-6}$-alkyl, C$_{3-8}$-cycloalkyl, aryl, heteroaryl and aryl, or denotes heteroaryl or C$_{3-8}$-cycloalkyl bonded via a C$_{1-3}$-alkylene group;
$R^6$ represents H, C$_{1-6}$-alkyl, or aryl, or denotes a C$_{3-8}$cycloalkyl bonded via a C$_{1-3}$-alkylene group, an aryl bonded via a C$_{1-3}$-alkylene group or a heteroaryl bonded via a C$_{1-3}$-alkylene group, and
$R^7$ represents C$_{1-6}$-alkyl, C$_{2-6}$-alkenyl or C$_{2-6}$-alkynyl, C$_{3-8}$cycloalkyl, aryl or heteroaryl; or denotes a C$_{3-8}$-cycloalkyl, aryl or heteroaryl bonded via a C$_{1-6}$-alkylene group; or
$R^6$ and $R^7$ together with the —N—C(=O) group form a ring of the type wherein d represents 0 or 1 and $R^{14}$ and $R^{15}$ together represent an annellated unsubstituted or substituted aryl or heteroaryl group;
wherein said C$_{1-6}$-alkyl, C$_{1-6}$-alkylene, C$_{2-6}$-alkenylene, C$_{2-6}$-alkynylene, C$_{3-8}$-cycloalkyl, C$_{3-8}$-heterocycloalkyl, aryl and heteroaryl groups each optionally may be unsubstituted or substituted one or more times by identical or different substituents; and said C$_{1-6}$-alkyl, C$_{1-6}$-alkylene, C$_{2-6}$-alkenylene and C$_{2-6}$-alkynylene groups each may be branched or unbranched;
or a physiologically acceptable salt thereof.

2. A compound according to claim 1, wherein said compound is in the form of an isolated stereoisomer.

3. A compound according to claim 1, wherein said compound is in the form of a mixture of stereoisomers in any mixing ratio.

4. A compound according to claim 3, wherein said mixture is a racemic mixture.

5. A compound according to claim 1, wherein n represents 0 or 1.

6. A compound according to claim 1, wherein $R^1$ represents a phenyl, naphthyl, indolyl, benzofuranyl, benzothiophenyl, benzoxazolyl, benzoxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl, benzyl or 2-phenethyl group, wherein said group optionally may be unsubstituted or substituted one or more times by identical or different substituents selected from the group consisting of —O—$C_{1-3}$-alkyl, $C_{1-6}$-alkyl, F, Cl, Br, I, $CF_3$, $OCF_3$, OH, SH, phenyl, naphthyl, furyl, thienyl and pyridinyl.

7. A compound according to claim 6, wherein $R^1$ represents an unsubstituted or optionally mono- or polysubstituted group selected from the group consisting of phenyl, naphthyl, benzothiophenyl, benzoxadiazolyl, thiophenyl, pyridinyl, imidazothiazolyl or dibenzofuranyl.

8. A compound according to claim 1, wherein p, q and r each represent 1.

9. A compound according to claim 1, wherein
Q represents a single bond, $CH_2$ or —O—;
n represents 0 or 1; and
o represents 1.

10. A compound according to claim 1, wherein $R^4$ and $R^5$ each independently represent H or substituted or unsubstituted $C_1$-$C_6$-alkyl, or the group —$NR^4R^5$ represents a heterocylic ring corresponding to formula IIa:

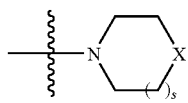

IIa wherein
X represents O, S, $NR^8$ or C(halogen)$_2$; wherein $R^8$ represents H; $C_{1-6}$-alkyl; aryl, or heteroaryl, or denotes an aryl or heteroaryl group bonded via a $C_{1-3}$-alkylene group;
s represents 0, 1 or 2, with the proviso that s is not 0 if X is $NR^8$; and
said $C_{1-6}$-alkyl, $C_{1-3}$-alkylene, aryl and heteroaryl groups each optionally may be unsubstituted or substituted one or more times by identical or different substituents.

11. A compound according to claim 10, wherein X represents $NR^8$; wherein:
$R^8$ represents H; $C_{1-6}$-alkyl, phenyl, naphthyl, or a 5- to 6-membered heteroaryl containing 1 or 2 N atoms, or denotes a phenyl, naphthyl or 5- to 6-membered heteroaryl containing 1 or 2 N atoms bonded via a $C_{1-3}$-alkylene group; and
s represents 1.

12. A compound according to claim 1, wherein $R^6$ represents H, $C_{1-6}$-alkyl, or aryl, or denotes aryl bonded via a $C_{1-3}$-alkylene group; wherein said $C_{1-6}$-alkyl, $C_{1-3}$-alkylene and aryl groups each may be unsubstituted or substituted once or more times by identical or different substituents.

13. A compound according to claim 1, wherein $R^7$ represents $C_{1-6}$-alkyl; $C_{4-7}$-cycloalkyl; aryl; a 5- to 6-membered heteroaryl containing 1 to 3 hetero atoms selected from the group consisting of N, O and S; or a $C_{4-6}$-cycloalkyl, aryl, or 5- to 6-membered heteroaryl containing 1 to 3 hetero atoms selected from the group consisting of N, O and S bonded via a $C_{1-3}$-alkylene group;

wherein said $C_{1-6}$-alkyl, $C_{4-7}$-cycloalkyl, aryl and heteroaryl each may be unsubstituted or substituted one or more times by identical or different substituents.

14. A compound according to claim 13, wherein $R^7$ represents $C_{1-6}$-alkyl; cyclopentyl; cyclohexyl; phenyl; naphthyl; pyridinyl; or a cyclopentyl, cyclohexyl, phenyl, naphthyl or pyridinyl bonded via a $C_{1-3}$-alkylene group.

15. A compound according to claim 1, wherein $R^2$ represents H, $C_{1-6}$alkyl, $C_{3-8}$-cycloalkyl or aryl; or denotes a $C_{3-6}$-cycloalkyl or aryl bonded via a $C_{1-6}$-alkylene group, $C_{2-6}$-alkenylene group or $C_{2-6}$-alkynylene group; wherein said $C_{1-6}$-alkyl, $C_{3-6}$-cycloalkyl, $C_{2-6}$-alkylene, $C_{2-6}$-alkenylene, $C_{2-6}$-alkynylene, and aryl each may be unsubstituted or substituted one or more times by identical or different substituents selected from the group consisting of $C_{1-6}$-alkyl, $C_{1-6}$-alkyl-O—, F, Cl, Br, I, $CF_3$, $OCF_3$, OH and SH.

16. A compound according to claim 1, wherein $R^3$ represents H, $C_{1-6}$-alkyl or aryl; or denotes an aryl bonded via a $C_{1-6}$-alkylene group, $C_{2-6}$-alkenylene group or $C_{2-6}$-alkynylene group, wherein said $C_{1-6}$-alkyl, $C_{2-6}$-alkylene, $C_{2-6}$-alkenylene, $C_{2-6}$-alkynylene, and aryl each may be unsubstituted or substituted one or more times by identical or different substituents selected from the group consisting of $C_{1-6}$-alkyl, $C_{1-6}$-alkyl-O—, F, Cl, Br, I, $CF_3$, $OCF_3$, OH and SH.

17. A compound according to claim 1, corresponding to formula Ia:

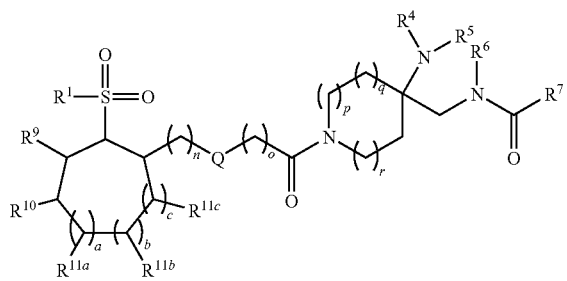

Ia wherein
a, b and c each independently represent 0 or 1;
$R^9$, $R^{10}$, $R^{11a}$, $R^{11b}$ and $R^{11c}$ each independently represent H or two vicinal radicals from $R^9$, $R^{10}$, $R^{11a}$, $R^{11b}$ and $R^{11c}$ form a 5- or 6-membered annellated aryl or heteroaryl ring, which optionally may be unsubstituted or substituted one or more times by identical or different substituents; and
$R^1$, $R^4$, $R^5$, $R^6$ and $R^7$ and Q, n, o, p, q and r each have the meanings given in claim 1.

18. A compound according to claim 17, corresponding to formula Ib:

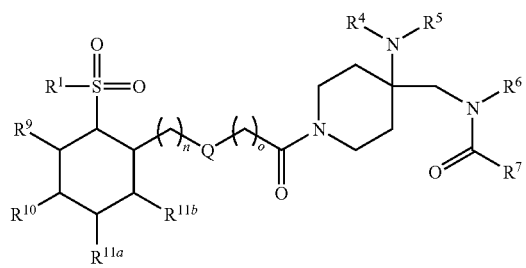

Ib wherein

R⁹, R¹⁰, R¹¹ᵃ and R¹¹ᵇ each independently represent H or two vicinal radicals from R⁹, R¹⁰, R¹¹ᵃ, R¹¹ᵇ and R¹¹ᶜ form a 5- or 6-membered aromatic or heteroaromatic ring, which may be unsubstituted or substituted one or more times with substituents independently selected from the group consisting of methyl, methoxy, CF₃, F, Cl and Br; and R¹, R⁴, R⁵, R⁶ and R⁷ and Q, n and o each have the meanings given in claim 17.

19. A compound according to claim 1, selected from the group consisting of (1) N-((1-(2-(2-(4-methoxy-N,2,6-trimethylphenylsulfonamido)ethoxy)acetyl)-4-(4-methylpiperazin-1-yl)piperidin-4-yl)methyl)isonicotinamide;

(2) N-((1-(3-(1-(4-chloro-2,5-dimethylphenylsulfonyl)piperidin-2-yl)propanoyl)-4-(4-methylpiperazin-1-yl)piperidin-4-yl)methyl)acetamide;

(3) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)-2-phenylacetamide;

(4) N-((4-(4-methylpiperazin-1-yl)-1-(2-(1-(3-(trifluoromethyl)phenylsulfonyl)-piperidin-2-yl)acetyl)piperidin-4-yl)methyl)-2-phenylacetamide;

(5) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)-benzamide;

(6) N-((1-(3-(1-(4-chloro-2,5-dimethylphenylsulfonyl)piperidin-2-yl)propanoyl)-4-(4-methylpiperazin-1-yl)piperidin-4-yl)methyl)benzamide;

(7) N-((1-(2-((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)-acetamide;

(8) N-((4-(4-methylpiperazin-1-yl)-1-(3-(naphthalene-2-sulfonamido)-3-phenylpropanoyl)piperidin-4-yl)methyl)-2-phenylacetamide;

(9) N-((1-(3-(1-(4-chloro-2,5-dimethylphenylsulfonyl)piperidin-2-yl)propan-oyl)-4-(4-methylpiperazin-1-yl)piperidin-4-yl)methyl)picolinamide,

(10) N-((1-(3-(1-(4-chloro-2,5-dimethylphenylsulfonyl)piperidin-2-yl)-propanoyl)-4-(4-methylpiperazin-1-yl)piperidin-4-yl)methyl)-2-phenylacetamide;

(11) N-((1-(3-(1-(4-chloro-2,5-dimethylphenylsulfonyl)piperidin-2-yl)propan-oyl)-4-(4-(pyridin-4-yl)piperazin-1-yl)piperidin-4-yl)methyl)acetamide,

(12) N-((4-(4-methylpiperazin-1-yl)-1-(2-(1-(3-(trifluoromethyl)phenylsulfonyl)-piperidin-2-yl)acetyl)piperidin-4-yl)methyl)acetamide;

(13) N-((1-(2-((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)-2-phenylacetamide;

(14) N-((1-(3-(naphthalene-2-sulfonamido)-3-phenylpropanoyl)-4-(4-(pyridin-4-yl)piperazin-1-yl)piperidin-4-yl)methyl)acetamide;

(15) N-((1-(2-(2-(4-methoxy-N,2,6-trimethylphenylsulfonamido)ethoxy)acetyl)-4-(4-methylpiperazin-1-yl)piperidin-4-yl)methyl)-2-phenylacetamide;

(16) N-((4-(4-methylpiperazin-1-yl)-1-(3-(naphthalene-2-sulfonamido)-3-phenylpropanoyl)piperidin-4-yl)methyl)benzamide;

(17) N-((1-(2-((1-(3,4-dichlorophenylsulfonyl)-1,2,3,4-tetrahydroquinolin-2-yl)-methoxy)acetyl)-4-(4-(pyridin-4-yl)piperazin-1-yl)piperidin-4-yl)methyl)-acetamide;

(18) N-((4-(4-methylpiperazin-1-yl)-1-(2-(1-(3-(trifluoromethyl)phenylsulfonyl)-piperidin-2-yl)acetyl)piperidin-4-yl)methyl)picolinamide;

(19) N-((4-(4-methylpiperazin-1-yl)-1-(3-(naphthalene-2-sulfonamido)-3-phenylpropanoyl)piperidin-4-yl)methyl)picolinamide;

(20) N-((1-(2-((1-(3,4-dichlorophenylsulfonyl)-1,2,3,4-tetrahydroquinolin-2-yl)-methoxy)acetyl)-4-(4-methylpiperazin-1-yl)piperidin-4-yl)methyl)-picolinamide;

(21) N-((1-(2-((1-(4-methoxy-2,6-dimethylphenylsulfonyl)piperidin-2-yl)-methoxy)acetyl)-4-(4-methylpiperazin-1-yl)piperidin-4-yl)methyl)-picolinamide;

(22) N-((1-(2-((1-(4-methoxy-2,6-dimethylphenylsulfonyl)piperidin-2-yl)-methoxy)acetyl)-4-(4-(pyridin-4-yl)piperazin-1-yl)piperidin-4-yl)methyl)-acetamide;

(23) N-((1-(2-((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)benzamide;

(24) N-((1-(2-(2-(4-methoxy-N,2,6-trimethylphenylsulfonamido)ethoxy)acetyl)-4-(4-methylpiperazin-1-yl)piperidin-4-yl)methyl)benzamide;

(25) N-((1-(2-(2-(4-methoxy-N,2,6-trimethylphenylsulfonamido)ethoxy)acetyl)-4-(4-methylpiperazin-1-yl)piperidin-4-yl)methyl)picolinamide;

(26) N-((1-(3-(1-(4-chloro-2,5-dimethylphenylsulfonyl)piperidin-2-yl)propan-oyl)-4-(4-methylpiperazin-1-yl)piperidin-4-yl)methyl)isonicotinamide,

(27) N-((1-(2-((1-(4-methoxy-2,6-dimethylphenylsulfonyl)piperidin-2-yl)-methoxy)acetyl)-4-(4-methylpiperazin-1-yl)piperidin-4-yl)methyl)-acetamide;

(28) N-((1-(2-((1-(4-methoxy-2,6-dimethylphenylsulfonyl)piperidin-2-yl)methoxy)acetyl)-4-(4-methylpiperazin-1-yl)piperidin-4-yl)methyl)-isonicotinamide;

(29) N-((4-(4-methylpiperazin-1-yl)-1-(2-(1-(3-(trifluoromethyl)phenylsulfonyl)-piperidin-2-yl)acetyl)piperidin-4-yl)methyl)isonicotinamide;

(30) N-((1-(2-((1-(3,4-dichlorophenylsulfonyl)-1,2,3,4-tetrahydroquinolin-2-yl)methoxy)acetyl)-4-(4-methylpiperazin-1-yl)piperidin-4-yl)methyl)-isonicotinamide;

(31) N-((1-(2-(2-(4-methoxy-N,2,6-trimethylphenylsulfonamido)ethoxy)acetyl)-4-(4-methylpiperazin-1-yl)piperidin-4-yl)methyl)acetamide;

(32) N-((1-(2-(2-(4-methoxy-N,2,6-trimethylphenylsulfonamido)ethoxy)acetyl)-4-(4-methylpiperazin-1-yl)piperidin-4-yl)methyl)nicotinamide;

(33) N-((1-(3-(1-(4-chloro-2,5-dimethylphenylsulfonyl)piperidin-2-yl)propan-oyl)-4-(4-methylpiperazin-1-yl)piperidin-4-yl)methyl)nicotinamide;

(34) N-((1-(2-(1-(4-methoxy-2,6-dimethylphenylsulfonyl)piperidin-2-yl)-meth-oxy)acetyl)-4-(4-methylpiperazin-1-yl)piperidin-4-yl)methyl)-nicotinamide;

(35) N-((4-(4-methylpiperazin-1-yl)-1-(3-(naphthalene-2-sulfonamido)-3-phenylpropanoyl)piperidin-4-yl)methyl)acetamide;

(36) N-((4-(4-(pyridin-4-yl)piperazin-1-yl)-1-(2-(1-(3-(trifluoromethyl)phenyl-sulfonyl)piperidin-2-yl)acetyl)piperidin-4-yl)methyl)acetamide,

(37) N-((4-(4-methylpiperazin-1-yl)-1-(3-(naphthalene-2-sulfonamido)-3-phenylpropanoyl)piperidin-4-yl)methyl)isonicotinamide;

(38) N-((4-(4-methylpiperazin-1-yl)-1-(3-(naphthalene-2-sulfonamido)-3-phenylpropanoyl)piperidin-4-yl)methyl)nicotinamide;

(39) N-((4-(4-methylpiperazin-1-yl)-1-(2-(1-(3-(trifluoromethyl)phenylsulfonyl)-piperidin-2-yl)acetyl)piperidin-4-yl)methyl)nicotinamide;

(40) N-((1-(2-((1-(3,4-dichlorophenylsulfonyl)-1,2,3,4-tetrahydroquinolin-2-yl)-methoxy)acetyl)-4-(4-methylpiperazin-1-yl)piperidin-4-yl)methyl)-nicotinamide;

(41) N-((1-(2-(2-(4-methoxy-N,2,6-trimethylphenylsulfonamido)ethoxy)acetyl)-4-(4-(pyridin-4-yl)piperazin-1-yl)piperidin-4-yl)methyl)acetamide;

(42) N-Cyclopropyl-N-(2-(2-(4-(4-cyclopropylpiperazin-1-yl)-4-((1-oxoisoindolin-2-yl)methyl)piperidin-1-yl)-2-oxoethoxy)ethyl)-4-methoxy-2,6-dimethylbenzenesulfonamide,

(43) N-((1-(2-(2-(2-Chloro-N-cyclopropyl-6-methylphenylsulfonamido)ethoxy)-acetyl)-4-(4-cyclopropylpiperazin-1-yl)piperidin-4-yl)methyl)-isonicotinamide;

(44) N-((1-(2-(2-(N-Cyclopropyl-4-methoxy-2,6-dimethylphenylsulfonamido)-ethoxy)acetyl)-4-(4-cyclopropylpiperazin-1-yl)piperidin-4-yl)methyl)-isonicotinamide;

(45) (S)—N-((4-(4-Cyclopropylpiperazin-1-yl)-1-(2-((1-(4-methoxy-2,6-dimethyl-phenylsulfonyflindolin-2-yl)methoxy)acetyl)piperidin-4-yl)methyl)-isonicotinamide,

(46) N-((1-(2-(2-(N-Cyclopropyl-4-methoxy-2,6-dimethylphenylsulfonamido)-ethoxy)acetyl)-4-(4-(pyridin-4-yl)piperazin-1-yl)piperidin-4-yl)methyl)-acetamide;

(47) N-((1-(2-(2-(N-Cyclopropyl-2-(trifluoromethyl)phenylsulfonamido)-ethoxy)acetyl)-4-(4-cyclopropylpiperazin-1-yl)piperidin-4-yl)methyl)-isonicotinamide;

(48) N-((1-(2-(2-(4-Methoxy-N,2,6-trimethylphenylsulfonamido)ethoxy)acetyl)-4-(4-methylpiperazin-1-yl)piperidin-4-yl)methyl)isonicotinamide hydrochloride;

(49) N-((1-(2-((4-(4-Methoxy-2,6-dimethylphenylsulfonyl)-3,4-dihydro-2H-benzo[b][1,4]oxazin-3-yl)methoxy)acetyl)-4-(4-methylpiperazin-1-yl)piperidin-4-yl)methyl)isonicotinamide

(50) N-((1-(2-((4-(2-Chloro-6-methylphenylsulfonyl)-3,4-dihydro-2H-benzo[b][1,4]oxazin-3-yl)methoxy)acetyl)-4-(4-methylpiperazin-1-yl)piperidin-4-yl)methyl)isonicotinamide;

(51) N-((1-(2-(2-(4-Methoxy-N,2,3,6-tetramethylphenylsulfonamido)ethoxy)-acetyl)-4-(4-methylpiperazin-1-yl)piperidin-4-yl)methyl)isonicotinamide;

(52) N-((1-(3-((1-(4-Methoxy-2,6-dimethylphenylsulfonyl)piperidin-2-yl)-methoxy)propanoyl)-4-(4-methylpiperazin-1-yl)piperidin-4-yl)methyl)-isonicotinamide

(53) N-((1-(2-(2-(1-(4-Methoxy-2,6-dimethylphenylsulfonyl)piperidin-2-yl)eth-oxy)acetyl)-4-(4-methylpiperazin-1-yl)piperidin-4-yl)methyl)isonicotinamide, and

(54) N-((1-(4-(N-Methyl-3-(trifluoromethyl)phenylsulfonamido)butanoyl)-4-(4-methylpiperazin-1-yl)piperidin-4-yl)methyl)isonicotinamide or a physiologically acceptable salt thereof.

20. A pharmaceutical composition comprising a compound according to claim 1 and at least one pharmaceutically acceptable additive or auxiliary substance, or a further active compound.

21. A method of treating or inhibiting a disorder or disease state selected from the group consisting of pain, diabetes, asthma, allergies, chronic obstructive pulmonary disease, ulcerative colitis, Crohn's disease, multiple sclerosis, atopic dermatitis, psoriasis, rheumatoid arthritis, osteoarthritis, septic shock, reperfusion syndrome and obesity or for inhibiting angiogenesis in a subject, said method comprising administering to said subject a pharmacologically effective amount of a compound according to claim 1.

22. A method according to claim 21, wherein said disorder or disease state is pain selected from the group consisting of acute pain, neuropathic pain, chronic pain, and inflammatory pain.

* * * * *